US010633667B2

(12) United States Patent
Guo et al.

(10) Patent No.: US 10,633,667 B2
(45) Date of Patent: *Apr. 28, 2020

(54) RECOMBINANT NDV ANTIGEN AND USES THEREOF

(75) Inventors: Xuan Guo, Suwanee, GA (US); Karolyn Marie Troupe, Athens, GA (US); Bradley J. Feilmeier, Watkinsville, GA (US); Joyce A. Pritchard, Gainesville, GA (US); Julio Sergio Cruz-Coy, Gainesville, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 799 days.

This patent is subject to a terminal disclaimer.

(21) Appl. No.: 12/979,677

(22) Filed: Dec. 28, 2010

(65) Prior Publication Data

US 2011/0162115 A1 Jun. 30, 2011

Related U.S. Application Data

(60) Provisional application No. 61/290,297, filed on Dec. 28, 2009.

(51) Int. Cl.
| | | |
|---|---|---|
| *C12N 9/24* | (2006.01) | |
| *C12N 15/86* | (2006.01) | |
| *C12N 7/00* | (2006.01) | |
| *C07K 14/005* | (2006.01) | |
| *A61K 39/00* | (2006.01) | |
| *A61K 38/00* | (2006.01) | |
| *C12N 15/82* | (2006.01) | |
| *A61K 39/17* | (2006.01) | |
| *A61K 39/12* | (2006.01) | |

(52) U.S. Cl.
CPC .......... *C12N 15/8258* (2013.01); *A61K 39/12* (2013.01); *A61K 39/17* (2013.01); *C07K 14/005* (2013.01); *A61K 39/00* (2013.01); *A61K 2039/517* (2013.01); *A61K 2039/545* (2013.01); *A61K 2039/552* (2013.01); *A61K 2039/55566* (2013.01); *C12N 2760/18122* (2013.01); *C12N 2760/18134* (2013.01)

(58) Field of Classification Search
USPC ........................................................ 435/201
See application file for complete search history.

(56) References Cited

U.S. PATENT DOCUMENTS

| | | | |
|---|---|---|---|
| 7,951,384 B2 * | 5/2011 | Morrison et al. ......... | 424/214.1 |
| 2003/0115640 A1 | 6/2003 | Stomp | |
| 2010/0189731 A1 | 7/2010 | Guo | |

FOREIGN PATENT DOCUMENTS

| | | | | |
|---|---|---|---|---|
| WO | WO02/36617 | 5/2002 | | |
| WO | WO2004/098533 | 11/2004 | | |
| WO | WO2009/009876 | 1/2009 | | |
| WO | WO 2009101160 A1 * | 8/2009 | ......... | C07K 14/4756 |
| WO | WO2009/114188 | 9/2009 | | |

OTHER PUBLICATIONS

Fukanoki, S. et al. "Safety and efficacy of water-in-oil-in-water emulsion vaccines containing Newcastle disease virus haemagglutinin-neuraminidase glycoprotein" Avian Pathology (2001) 30, 509-516.*
Wang, Z. et al. "Expression and characterization of soluble human parainfluenza virus type 1 hemagglutinin neuraminidase glycoprotein" Journal of Virological methods 2001 (98)53-61.*
Gomez, E. et al. "Expression of Hemagglutinin-Neuraminidase glycoprotein of Newcastle Disease virus in agrofiltrated Nicotiana benthamiana plants" Journal of Biotechnology 2009 (144) 337-340.*
Miller "Antigenic differences among Newcastls disease virus strains of different genotyoes used invaccine formulation affect viral shedding after a virulent challenge" Vaccine 2007 25 7238-7246.*
Takimoto "Crystallization of Newcastle Disease Virus Hemagglutinin-Neuraminidase Glycoprotein" Virology 2000 270 208-214.*
Mayfield SP et al. Expression of human antibodies in eukaryotic micro-algae. 2005. Vaccine. 23. 1828-1832.*
Raju TS. Glycosylation variations within expression systems. 2003. Bioprocess International. p. 44-53.*
Lee Y et al. Protection of chickens from Newcastle disease with a recombinant baculovirus subunit vaccine expressing the fusion and hemagglutinin-neuraminidase proteins. 2008. Journal of Veterinary Science. 9(3). 301-308.*
Mathieu-Rivet et al, "Protein N-glycosylation in eukaryotic microalgae and its impact on the production of nuclear expressed biopharmaceuticals," Frontiers in Plant Science, Jul. 2014, vol. 5, Article 359.
Peeters BPH et al., "generatiaon of a recombinant chimeric Newcastle disease virus vaccine that allows serological differentiation between vaccinated and infected animals", Vaccine, vol. 19, p. 1616-1627, 2001.
Doreen Manuela Floss et al., "Production of vaccines and therapeutic antibodies for veterinary applications in transgenic plants: an overview", Transgenic Research, vol. 16, p. 315-332, 2007.
Quo Xuan et al., "Lemna (duckweed_ expressed hemagglutinin from avian influenza H5N1 protects chickens against H5N1 high pathogenicity avina influenza virus challenge", Internet Citation, p. 1-2, 2009.
Fuhrmann Markus, "production of antigens in chlamydomonas reinhardtti: green microalgae as a novel source of recombinant proteins", Methods in Molecular Medicine, vol. 94, p. 191-195, 2004.

(Continued)

*Primary Examiner* — Paul J Holland
(74) *Attorney, Agent, or Firm* — Judy Jarecki-Black; Richard Seeger

(57) ABSTRACT

The present invention encompasses NDV vaccines. The vaccine may be a subunit vaccine based on HN of NDV. The NDV HN may be expressed in plants or algae including microalgae. The invention also encompasses recombinant vectors encoding and expressing NDV antigens, epitopes or immunogens which can be used to protect animals against NDV. It encompasses also a vaccination regime compatible with the DIVA strategy, including a prime-boost scheme using viral vector or inactivated vaccines and subunit vaccines.

12 Claims, 26 Drawing Sheets

Specification includes a Sequence Listing.

(56) References Cited

OTHER PUBLICATIONS

Siripornadulsil Surasak et al., "Microalgal vaccines", Advances in Experimental Medicine and Biology, p. 122-128, 2007 D'Aoust Marc-Andre et al., "influenza virus0like particles produced by transient expression in Nicotiana benthamiana induce a protective immune response against a lethal viral challenge in mice", Plant Biotechnology Journal, vol. 6 No. 9, p. 930-940, 2008.
D'Aoust Marc-Andre et al., "influenza virus0like particles produced by transient expression in Nicotiana benthamiana induce a protective immune response against a lethal viral challenge in mice", Plant Biotechnology Journal, vol. 6 No. 9, p. 930-940, 2008.
Lamb et al., 2007, Paramyxoviridae: The viruses and Their Replication, p. 1449-1496.
Mayo, 2002, "A summary of taxonomic changes recently approved by ICTV", Arch Virol 147:1655-63.
Alexander, 1988, Newcastle disease, p. 11-20.
Giddings et al., "Transgenic plants as factories for biopharmaceuticals", Nature Biotech. 2000, 18, 1151-1155.
Berinstein A., et al., 2005, "Mucosal and systemic immunization elicited by Newcastle disease virus (NDV) transgenic plants as antigens", Vaccine 23: 5583-6689.
Chargelegue et al., "Transgenic plants for vaccine production : expectations and limitations Trends in Plant", Science 2001, 6, 495-496.
Schilberg et al., "Opportunities for recombinant antigen and antibody expression in transgenic plants—technology assessment", Vaccine 2005, 23, 1764-1769.
Arntzen et al., "plant-derived vaccines and antibodies : potential and limitations", Vaccine 2005, 23, 1753-1756.
Koprowski, "Vaccines and sera through plant biotechnology", Vaccine 2005, 23, 1757-1763.

\* cited by examiner

Figure 1

| SEQ ID NO: | Type | Description |
|---|---|---|
| 1 | DNA | NDV HN codon-optimized DNA |
| 2 | DNA | NDV HN wild type DNA (EF520717) (gamefowl/US(CA)/212676/2002 strain) |
| 3 | Protein | NDV HN protein (ABS84265) (gamefowl/US(CA)/212676/2002 strain) |
| 4 | DNA | NDV HN DNA (M21409) (Texas GB strain) |
| 5 | Protein | NDV HN protein (P12553) (Texas GB strain) |
| 6 | DNA | NDV HN DNA (M24709) (LaSota strain) |
| 7 | Protein | NDV HN protein (AAA46659) (LaSota strain) |
| 8 | DNA | NDV HN DNA (AY288999) (MEX/96 strain) |
| 9 | Protein | NDV HN protein (AAQ54638) (MEX/96 strain) |
| 10 | Protein | NDV HN Linear Epitope Region 1 |
| 11 | Protein | NDV HN Linear Epitope Region 2 |
| 12 | DNA | NDV HN signal sequence |
| 13 | Protein | NDV HN signal peptide (from SEQ ID NO:3, ABS84265) |
| 14 | DNA | NDV HN DNA encoding mature protein (without signal sequence, 79bp -1716bp of SEQ ID NO:1) (codon-optimized) |
| 15 | Protein | NDV HN mature protein (without signal peptide, 27aa-571aa of SEQ ID NO:3) (EF520717) (gamefowl/US(CA)/212676/2002 strain) |
| 16 | DNA | NDV HN DNA (FJ608369) (NDV strain chicken YZCQ/Liaoning/08) |
| 17 | Protein | NDV HN protein(ACM67348) (NDV strain chicken YZCQ/Liaoning/08) |
| 18 | DNA | NDV HN DNA (NDV strain ZJ1) |
| 19 | Protein | NDV HN protein (AAL18936) (NDV strain ZJ1) |
| 20 | Protein | NDV HN mature protein (without signal peptide, 47aa-571aa of SEQ ID NO:17, ACM67348) |
| 21 | Protein | NDV HN signal peptide (from SEQ ID NO:17, ACM67348) |
| 22 | DNA | NDV HN codon-optimized DNA encoding ACM67348 |
| 23 | DNA | NDV HN codon-optimized DNA encoding mature protein (without signal sequence, 139 bp -1713 bp of SEQ ID NO:22, NDV strain chicken YZCQ/Liaoning/08) |
| 24 | Protein | ER retention sequence (KDEL) |
| 25 | DNA | alpha amylase signal sequence |
| 26 | protein | alpha amylase signal peptide |
| 27 | DNA | NDV HN signal sequence, codon-optimized (duckweed-preferred codon optimization) (1-138 bp of SEQ ID NO:22) |
| 28 | protein | NDV HN Linear Epitope Region 3 |

Figure 2

HN Seqeunces of LaSota, CA/02 and TX/GB strains of NDV. Glycosylation sites are underlined.

```
NDV HN CA/02  (ABS84265)(SEQ ID NO:3)
   1 MDRVVSRVVL ENEEREAKNT WRLVFRVAVL SLIVMTLAIS VAALVYSMEA STPNDLAGIS
  61 TVISRAEDRV TSLLNSNQDV VDRVYKQVAL ESPLALLNTE SIIMNAITSL SYQINGAANS
 121 SGCGAPVHDP DYIGGVGKEL IVDDTSDATS FYPSAYQEHL NFIPAPTTGS GCTRIPSFDM
 181 SATHYCYTHN VILSGCRDHS HSHQYLALGV LRTSATGRVF FSTLRSINLD DTQNRKSCSV
 241 SATPLGCDML CSKVTETEEE DYKSVTPTSM VHGRLGFDGQ YHEKDLDVTV LFKDWVANYP
 301 GVGGGSLIDD RVWFPVYGGL KPNSPSDTAQ EGKYVIYKRY NNTCPDEQDY QVRMAKSSYK
 361 PGRFGGKRVQ QAILSIKVST SLGEDPVLTV PPNTVTLMGA EGRILTVGTS HFLYQRGSSY
 421 FSPALLYPMT VRNKTATLHS PYTFNAFTRP GSVPCQASAR CPNSCITGVY TDPYPVVFHR
 481 NHTLRGVFGT MLDNEQARLN PVSAIFDYTS RSRITRVSST STKAAYTTST CFKVVKTNKV
 541 YCLSIAEISN TLFGEFRIVP LLVEILKDDR V

NDV HN TX/GB  (P12553)(SEQ ID NO:5)
   1 MDRAVSQVAL ENDEREAKNT WRLIFRIAIL LLTVVTLATS VASLVYSMGA STPSDLVGIP
  61 TRISRAEEKI TSALGSNQDV VDRIYKQVAL ESPLALLNTE TTIMNAITSL SYQINGAANN
 121 SGWGAPIHDP DFIGGIGKEL IVDDASDVTS FYPSAFQEHH NFIPAPTTGS GCIRIPSFDM
 181 SATHYCYTHN IISSGCRDHS HSYQYLALGV LRTSATGRIF FSTLRSINLD DTQNRKSCSV
 241 SATPLGCDML CSKVTETEEE DYNSAVPTLM VHGRLGFDGQ YHEKDLDVTT LFEDWVANYP
 301 GVGGGSFIDS RVWFSVYGGL KPNSPSDTVQ EEKYVIYKRY NDTCPDEQDY QIRMAKSSYK
 361 PGRFGGKRIQ QAILSIKVST SLGEDPVLTV PPNTVTLMGA EGRILTVGTS HFLYQRGSSY
 421 FSPALLYPMT VSNKTATLHS PYTFNAFTRP GSIPCQASAR CPNSCVTGVY TDPYPLIFYR
 481 NHTLRGVFGT MLDGEQARLN PASAVFDSTS RSRITRVSSS STKAAYTTST CFKVVKTNKT
 541 YCLSIAEISN TLFGEFRIVP LLVEILKNDG VREARSG

NDV HN LaSota  (AAA46659)(SEQ ID NO:7)

MDRAVSQVAL ENDEREAKNT WRLIFRIAIL FLTVVTLAIS VASLLYSMGA STPSDLVGIP  60
TRISRAEEKI TSTLGSNQDV VDRIYKQVAL ESPLALLKTE TTIMNAITSL SYQINGAANN 120
SGWGAPIHDP DYIGGIGKEL IVDDASDVTS FYPSAFQEHL NFIPAPTTGS GCTRIPSFDM 180
SATHYCYTHN VILSGCRDHS HSYQYLALGV LRTSATGRVF FSTLRSINLD DTQNRKSCSV 240
SATPLGCDML CSKVTETEEE DYNSAVPTRM AHGRLGFDGQ YHEKDLDVTT LFGDWVANYP 300
GVGGGSFIDG RVWFSVYGGL KPNSPSDTVQ EGKYVIYKRY NDTCPDEQDY QIRMAKSSYK 360
PGRFGGKRIQ QAILSIKVST SLGEDPVLTV PPNTVTLMGA EGRILTVGTS HFLYQRGSSY 420
FSPALLYPMT VSNKTATLHS PYTFNAFTRP GSIPCQASAR CPNPCVTGVY TDPYPLIFYR 480
NHTLRGVFGT MLDGVQARLN PTSAVFDSTS RSRITRVSSS STKAAYTTST CFKVVKTNKT 540
YCLSIAEISN TLFGEFRIVP LLVEILKDDG VREARSG                          577
```

Figure 3
Figure 3A
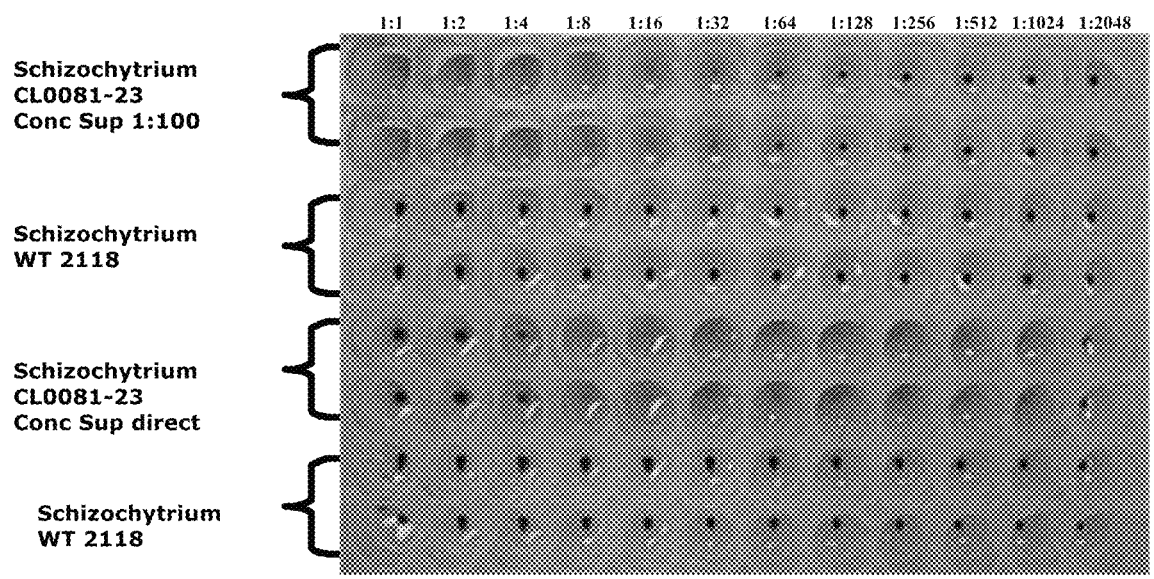
Figure 3B
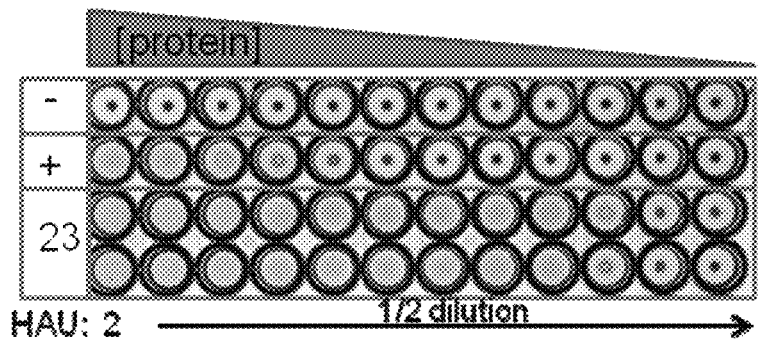

Figure 4

Secretion of HN protein by transgenic *Schizochytrium* - immunoblot analysis

Figure 5
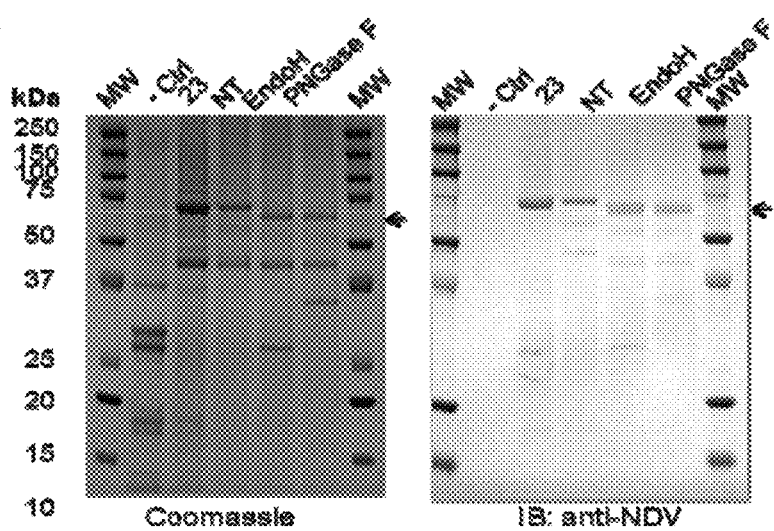
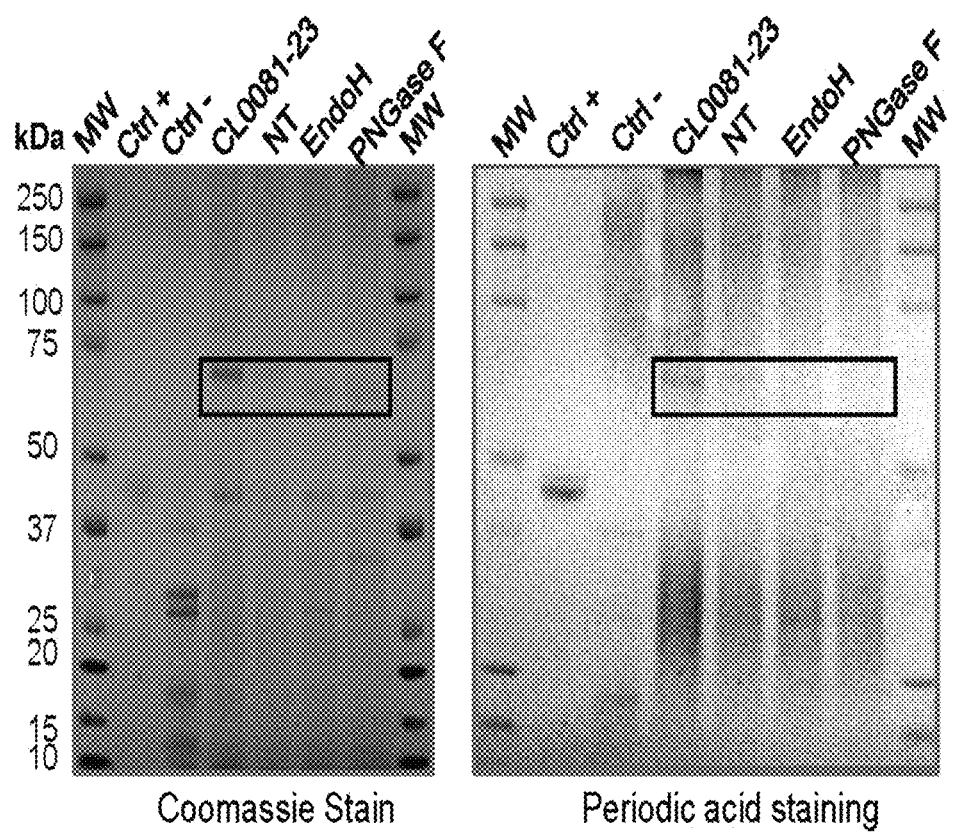

Figure 6.1A

```
                                      1                                                50
NDV HN ABS84265 (CA2002)    (1)  MDRVVSRVVLENEEREAKNTWRLVFRVAVLSLIVMTLAISVAALVYSMEA
NDV HN MEX96   (AAQ54638)   (1)  MDRVVSRVVLENEEREAKNTWRLVFRIAVLSLIVMTLAISVAALVYSMEA
NDV HN LaSota  (AAA46659)   (1)  MDRAVSQVALENDEREAKNTWRLIFRIALLFLTVVTLAISVASLVYSMGA
NDV HN Texas   (P12553)     (1)  MDRAVSQVALENDEREAKNTWRLIFRIALLLTVVTLATSVAALVYSMGA
NDV HN Liaoning (ACM67348)  (1)  MGRAVNRVALENEEREAKNTWRLVFRIAVLLLMVMTLASSAAALAYSAGA
NDV HN ZJ1     (AAL18936)   (1)  MDRAVNRVVLENEEREAKNTWRLVFRIAVLLLMVMTLASSAAALAYSTGA 51                                               100
NDV HN ABS84265 (CA2002)    (51) STPNDLAGISTVISRAEDRVTSLLNSKQDVVDRVYKQVALESPLALLNTE
NDV HN MEX96   (AAQ54638)   (51) STPNDLAGISTVISRAEDRVTSLLNSKQDVVDRVYKQVALESPLALLNTE
NDV HN LaSota  (AAA46659)   (51) STPSDLVGIPTRISRAEEKITSTLGSKQDVVDRIYKQVALESPLALLKTE
NDV HN Texas   (P12553)     (51) STPSDLVGIPTRISRAEEKITSALGSKQDVVDRIYKQVALESPLALLNTE
NDV HN Liaoning (ACM67348)  (51) STPHDLAGISTVISKTEDRVTSLLSSSQDVIDRIYKQVALESPLALLNTE
NDV HN ZJ1     (AAL18936)   (51) STPHDLAGISTVISKTEDRVTSLLSLSQDVIDRIYKQVALESPLALLNTE 101                                              150
NDV HN ABS84265 (CA2002)    (101) SIIMNAITSLSYQINGAARSSGQGAPVHDPDYIGGVGKELIVDDTSDATS
NDV HN MEX96   (AAQ54638)   (101) SIIMNAITSLSYQINGAANSSGQGAPVHDPDYIGGVGKELIVDDTSDATS
NDV HN LaSota  (AAA46659)   (101) TIMNAITSLSYQINGAANNSGWGAPIHDPDYIGGIGKELIVDDASDVTS
NDV HN Texas   (P12553)     (101) TIMNAITSLSYQINGAANNSGWGAPIHDPDYIGGIGKELIVDDASDVTS
NDV HN Liaoning (ACM67348)  (101) SIIMNAITSLSYQINGAANNSGQGAPVHDPDYIGGIGKELIVDDISDVTS
NDV HN ZJ1     (AAL18936)   (101) SIIMNAITSLSYQINGAANNSGQGAPVHDPDYIGGIGKELIVDDISDVTS 151                                              200
NDV HN ABS84265 (CA2002)    (151) FYPSAVQEHLNFIPAPTTGSGCTRIPSFDMSATHYCYTHNVISGCRDHS
NDV HN MEX96   (AAQ54638)   (151) FYPSAVQEHLNFIPAPTTGSGCTRIPSFDMSATHYCYTHNVISGCRDHS
NDV HN LaSota  (AAA46659)   (151) FYPSAVQEHLNFIPAPTTGSGCTRIPSFDMSATHYCYTHNVISGCRDHS
NDV HN Texas   (P12553)     (151) FYPSAVQEHHNFIPAPTTGSGCIRIPSFDMSATHYCYTHNISSGCRDHS
NDV HN Liaoning (ACM67348)  (151) FYPSAVQEHLNFIPAPTTGSGCTRIPSFDMSTTHYCYTHNVISGCRDHS
NDV HN ZJ1     (AAL18936)   (151) FYPSAVQEHLNFIPAPTTGSGCTRIPSFDMSTTHYCYTHNVISGCRDHS 201                                              250
NDV HN ABS84265 (CA2002)    (201) HSHQYLALGVLRTSATGRVFFSTLRSINLDDTQNRKSCSVSATSLGCDML
NDV HN MEX96   (AAQ54638)   (201) HSHQYLALGVLRTSATGRVFFSTLRSINLDDTQNRKSCSVSATSLGCDML
NDV HN LaSota  (AAA46659)   (201) HSKQYLALGVLRTSATGRVFFSTLRSINLDDTQNRKSCSVSATSLGCDML
NDV HN Texas   (P12553)     (201) HSKQYLALGVLRTSATGRIFFSTLRSINLDDTQNRKSCSVSATSLGCDML
NDV HN Liaoning (ACM67348)  (201) HSHQYLALGVLRTSATGRVFFSTLRSINLDDTQNRKSCSVSATSLGCDML
NDV HN ZJ1     (AAL18936)   (201) HSHQYLALGVLRTSATGRVFFSTLRSTNLDDTQNRKSCSVSATSLGCDML 251                                              300
NDV HN ABS84265 (CA2002)    (251) CSKVTETEEEDYKSVTPTSMVHGRLGFDGQYHEKDLDVTVLFKDWVANYP
NDV HN MEX96   (AAQ54638)   (251) CSKVTETEEEDYKSVTPTSMVHGRLGFDGQYHEKDLDVTVLFKDWVANYP
NDV HN LaSota  (AAA46659)   (251) CSKVTETEEEDYNSAVPTRMAHGRLGFDGQYHEKDLDVTTLFGDWVANYP
NDV HN Texas   (P12553)     (251) CSKVTETEEEDYNSAVPTLMVHGRLGFDGQYHEKDLDVTTLFEDWVANYP
NDV HN Liaoning (ACM67348)  (251) CSKVTGTEEEDYKSVAPTMVHGRLGFDGQYHEKDLDTTVLFKDWVANYP
NDV HN ZJ1     (AAL18936)   (251) CSKVTETEEEDYKSVAPTSMVHGRLGFDGQYHEKDLDTTVLFKDWVANYP 301                                              350
NDV HN ABS84265 (CA2002)    (301) GVGGGSLIDDRVWFPVYGGLKPNSPSDTAQEGKYVIYKRYNNTCPDEQDY
NDV HN MEX96   (AAQ54638)   (301) GVGGGSLIDDRVWFPVYGGLKPNSPSDTAQEGKYVIYKRYNNTCPDEQDY
NDV HN LaSota  (AAA46659)   (301) SVGGGSIDGRVWFSVYGGLKPNSPSDTVQEGKYVIYKRYNDTCPDEQDY
NDV HN Texas   (P12553)     (301) GVGGGSIDSRVWFSVYGGLKPNSPSDTVQEEKYVIYKRYNDTCPDEQDY
NDV HN Liaoning (ACM67348)  (301) GVGGGSIDNRVWFPVYGGLKPNSPSDTAQEGKYVIYKRHNNTCPDKQDY
NDV HN ZJ1     (AAL18936)   (301) GAGGGSIDDRVWFPVYGGLKPNSPSDTAQEGKYVIYKRHNNTCPDKQDY 351                                              400
NDV HN ABS84265 (CA2002)    (351) QVRMAKSSYKPGRFGGKRVQQAILSIKVSTSLGEDPVLTVPPNTVTLMGA
NDV HN MEX96   (AAQ54638)   (351) QVRMAKSSYKPGRFGGKRVQQAILSIKVSTSLGEDPVLTVPPNTVTLMGA
NDV HN LaSota  (AAA46659)   (351) QIRMAKSSYKPGRFGGKRIQQAILSIKVSTSLGEDPVLTVPPNTVTLMGA
NDV HN Texas   (P12553)     (351) QIRMAKSSYKPGRFGGKRIQQAILSIKVSTSLGEDPVLTVPPNTVTLMGA
NDV HN Liaoning (ACM67348)  (351) QIRMAKSSYKPGRFGGKRVQQAILSIKVSTSLGKDPVLTIPPNTITLMGA
NDV HN ZJ1     (AAL18936)   (351) QIRMAKSSYKPGRFGGKRVQQAILSIKVSTSLGKDPVLTIPPNTITLMGA
```

Figure 6.1B

```
                                       401                                                     450
NDV HN ABS84265 (CA2002)    (401) EGRILTVGTSHFLYQRGSSYFSPALLYPMTVRNKTATLHSPYTFNAFTRP
NDV HN MEX96   (AAQ54638)   (401) EGRILTVGTSHFLYQRGSSYFSPALLYPMTVRNKTATLHSPYTFNAFTRP
NDV HN LaSota  (AAA46659)   (401) EGRILTVGTSHFLYQRGSSYFSPALLYPMTVSNKTATLHSPYTFNAFTRP
NDV HN Texas   (P12553)     (401) EGRILTVGTSHFLYQRGSSYFSPALLYPMTVSNKTATLHSPYTFNAFTRP
NDV HN Liaoning(ACM67348)   (401) EGRILTVGTSHFLYQRGSSYFSPALLYPMTVNNKTATLHSPYTFNAFTRP
NDV HN ZJ1     (AAL18936)   (401) EGRILTVGTSHFLYQRGSSYFSPALLYPMTVNNKTATLHSPYTFNAFTRP 451                                                     500
NDV HN ABS84265 (CA2002)    (451) GSVPCQASARCPNSCITGVYTDPYPVYFRNHTLRGVFGTMLDNEQARLN
NDV HN MEX96   (AAQ54638)   (451) GSVPCQASARCPNSCITGVYTDPYPVYFRNHTLRGVFGTMLDNEQARLN
NDV HN LaSota  (AAA46659)   (451) GSIPCQASARCPNPCVTGVYTDPYPLIFRNHTLRGVFGTMLDGVQARLN
NDV HN Texas   (P12553)     (451) GSIPCQASARCPNSCVTGVYTDPYPLIFRNHTLRGVFGTMLDGEQARLN
NDV HN Liaoning(ACM67348)   (451) GSAPCQASARCPNSCITGVYTDPYPLIFRNHTLRGVFGTMLDDEQARLN
NDV HN ZJ1     (AAL18936)   (451) GSVPCQASARCPNSCITGVYTDPYPLIFRNHTLRGVFGTMLDDEQARLN 501                                                     550
NDV HN ABS84265 (CA2002)    (501) PYSAVFDYSRSRSITRVSSSSTKAAYTTSTCFKVVKTNKVYCLSIAEISN
NDV HN MEX96   (AAQ54638)   (501) PYSAVFDYSRSRSITRVSSISTKAAYTTSTCFKVVKTNKVYCLSIAEISN
NDV HN LaSota  (AAA46659)   (501) PTSAVFDSSRSRSITRVSSSSTKAAYTTSTCFKVVKTNKTYCLSIAEISN
NDV HN Texas   (P12553)     (501) PASAVFDSSRSRSITRVSSSSTKAAYTTSTCFKVVKTNKTYCLSIAEISN
NDV HN Liaoning(ACM67348)   (501) PYSAVFDNISRSRSVTRVSSSSTKAAYTTSTCFKVVKTNKAYCLSIAEISN
NDV HN ZJ1     (AAL18936)   (501) PYSAVFDNISRSRSVTRVSSSSTKAAYTTSTCFKVVKTNKTYCLSIAEISN 551                      577
NDV HN ABS84265 (CA2002)    (551) TLFGEFRIVPLLVEILKDDRV------
NDV HN MEX96   (AAQ54638)   (551) TLFGEFRIVPLLVEILKDDRV------
NDV HN LaSota  (AAA46659)   (551) TLFGEFRIVPLLVEILKDGVREARSG
NDV HN Texas   (P12553)     (551) TLFGEFRIVPLLVEILKNDGVREARSG
NDV HN Liaoning(ACM67348)   (551) TLFGEFRIVPLLVEILKDDRV------
NDV HN ZJ1     (AAL18936)   (551) TLFGEFRIVPLLVEILKDDRV------
```

NDV HN ABS84265 (CA2002): SEQ ID NO:3
NDV HN MEX96 (AAQ54638): SEQ ID NO:9
NDV HN LaSota (AAA46659): SEQ ID NO:7
NDV HN Texas (P12553): SEQ ID NO:5
NDV HN Liaoning (ACM67348): SEQ ID NO:17
NDV HN ZJ1 (AAL18936): SEQ ID NO:19

Sequence identity percentage:

| SEQ ID NO: | 9 | 3 | 7 | 5 | 17 | 19 |
|---|---|---|---|---|---|---|
| 9 | 100 | 99 | 89 | 88 | 92 | 92 |
| 3 |  | 100 | 89 | 88 | 92 | 92 |
| 7 |  |  | 100 | 97 | 88 | 87 |
| 5 |  |  |  | 100 | 87 | 87 |
| 17 |  |  |  |  | 100 | 97 |
| 19 |  |  |  |  |  | 100 |

Vector NTI 11.0 (PC) software package (Invitrogen, 1600 Faraday Ave., Carlsbad, CA).

Figure 6.2

```
                         1                                                50
SEQ ID NO:20    (1)   --------------------SAGASTPHDLAGISTVISRTEDKVTSLLSS
SEQ ID NO:15    (1)   VAVLSLIVMTLAISVAALVYSMEASTPNDLAGISTVISRAEDRVTSLLNS 51                                               100
SEQ ID NO:20    (31)  SQDVIDRIYKQVALESPLALLNTESMIMNAITSLSYQINGAANNSGCGAP
SEQ ID NO:15    (51)  NQDVVDRVYKQVALESPLALLNTESIIMNAITSLSYQINGAANSSGCGAP 101                                              150
SEQ ID NO:20    (81)  VHDPDYIGGIGKELIVDDISDVTSFYPSAYQEHLNFIPAPTTGSGCTRIP
SEQ ID NO:15    (101) VHDPDYIGGVGKELIVDDTSDATSFYPSAYQEHLNFIPAPTTGSGCTRIP 151                                              200
SEQ ID NO:20    (131) SFDMSTTHYCYTHNVILSGCRDHSHSQYLALGVLRTSATGRVFFSTLRS
SEQ ID NO:15    (151) SFDMSATHYCYTHNVILSGCRDHSHSQYLALGVLRTSATGRVFFSTLRS 201                                              250
SEQ ID NO:20    (181) INLDDTQNRKSCSVSATPLGCDMLCSKVTGTEEEDYKSVAPTPMVHGRLG
SEQ ID NO:15    (201) INLDDTQNRKSCSVSATPLGCDMLCSKVTETEEEDYKSVTPTSMVHGRLG 251                                              300
SEQ ID NO:20    (231) FDGQYHEKDLDTTVLFKDWVANYPGVGGGSFIDNRVWFPVYGGLKPNSPS
SEQ ID NO:15    (251) FDGQYHEKDLDVTVLFKDWVANYPGVGGGSLIDDRVWFPVYGGLKPNSPS 301                                              350
SEQ ID NO:20    (281) DTAQEGKYVIYKRINNTCPDKQDYQIRMAKSSYKPGRFGGKRVQQAILSI
SEQ ID NO:15    (301) DTAQEGKYVIYKRINNTCPDEQDYQVRMAKSSYKPGRFGGKRVQQAILSI 351                                              400
SEQ ID NO:20    (331) KVSTSLGKDPVLTIPPNTITLMGAEGRILTVGTSHFLYQRGSSYFSPALL
SEQ ID NO:15    (351) KVSTSLGEDPVLTVPPNTVTLMGAEGRILTVGTSHFLYQRGSSYFSPALL 401                                              450
SEQ ID NO:20    (381) YPMTVNNKTATLHSPYTFNAFTRPGSAPCQASARCPNSCITGVYTDPYPI
SEQ ID NO:15    (401) YPMTVRNKTATLHSPYTFNAFTRPGSVPCQASARCPNSCITGVYTDPYPV 451                                              500
SEQ ID NO:20    (431) IFHRNHTLRGVFGTMLDDEQARLNPVSAVFDNISRSRITRVSSISTKAAY
SEQ ID NO:15    (451) VFHRNHTLRGVFGTMLDNEQARLNPVSAIFDYTSRSRITRVSSISTKAAY 501                                              546
SEQ ID NO:20    (481) TTSTCFKVVKTNKAYCLSIAEISNTLFGEFRIVPLLVEILKDDRV-
SEQ ID NO:15    (501) TTSTCFKVVKTNKVYCLSIAEISNTLFGEFRIVPLLVEILKDDRV-
```

The protein identity percentage between SEQ ID NO:15 and SEQ ID NO:20 is 93%.

Figure 7.1A

```
                                  1                                                50
NDV HN  (FJ608369)     (1)  --------------------------------------------------
NDV HN  (ZJ1 strain)   (1)  --------------------------------------------------
NDV HN LaSota (M24709) (1)  ACGGGTAGAACGGTAAGAGAGGCCGCCCCTCAATTGCGAGCCAGGCTTCA
NDV HN  texas (M21409) (1)  --------------------------------------------------
NDV HN  CA02 (EF520717)(1)  --------------------------------------------------
NDV HN  MEX (AY288999 )(1)  --------------------------------------------------

51                                              100
NDV HN  (FJ608369)     (1)  ---------------------------------------------ATGGACGG
NDV HN  (ZJ1 strain)   (1)  ---------------------------------------------ATGGACGG
NDV HN LaSota (M24709)(51)  CAACCTCCGTTCTACCGCTTCACCGACAACAGTCCTCAATCATGGACGG
NDV HN  texas (M21409) (1)  -----------------------------GTCCTCAGTCATGGACGG
NDV HN  CA02 (EF520717)(1)  ---------------------------------------------ATGGATCGT
NDV HN  MEX (AY288999 )(1)  ---------------------------------------------ATGGATCGT 101                                             150
NDV HN  (FJ608369)    (10)  GCGGTTAACAGAGTCGCGGTGGAGAATGAGGAAAGAGAAGCAAAGAACAC
NDV HN  (ZJ1 strain)  (10)  GCGGTTAACAGAGTCGCGGTGGAGAATGAGGAAAGAGAAGCAAAGAACAC
NDV HN LaSota (M24709)(101) GCCGTTAGCCAAGTGGCGTTAGAGAATGATGAAAGAGAGGCAAAAAATAC
NDV HN  texas (M21409)(20)  GCAGTTAGCCAAGTGGCGTTAGAGAATGATGAAAGAGAGGCAAAAAATAC
NDV HN  CA02 (EF520717)(10) GTAGTTAGCAGAGTCGGACTAGAAAACGAAGAAAGAGAAGCAAAGAATAC
NDV HN  MEX (AY288999)(10)  GTAGTTAGCAGAGTCGGACTAGAGAACGAAGAAAGAGAAGCAAAGAATAC 151                                             200
NDV HN  (FJ608369)    (60)  ATGGCGCTGGTTTTCCGGATGGCAGTCTACTTTAATGGTAATGACTC
NDV HN  (ZJ1 strain)  (60)  ATGGCGCTGGTTTTCCGGATGGCAGTCTACTTTAATGGTAATGACTC
NDV HN LaSota (M24709)(151) ATGGCGCTTGATATTCCGGATTGCAATCTACTCTTAACAGTAGTGACCT
NDV HN  texas (M21409)(70)  ATGGCGCTTGATATTCCGGATTGCAATCTACTCTTAACAGTAGTGACCT
NDV HN  CA02 (EF520717)(60) ATGGCGCTGGTTTTCCGGGTGGCAGTCCTACCTCTAATAGTAATGACAT
NDV HN  MEX (AY288999)(60)  TTGGCGCCTGGTTTTCCGGATGGCAGTCCTACCTCTAATAGTAATGACAT 201                                             250
NDV HN  (FJ608369)    (110) TAGCTATCTCCGCAGCTGCCCTGGCATAGAGTGCGGGGGCCAGTACGCCG
NDV HN  (ZJ1 strain)  (110) TGGCTATCTCCGCAGCTGCCCTGGCATAGAGTACGGGGGCCAGTACGCCG
NDV HN LaSota (M24709)(201) TGGCTACATCTGTAGCCTCCCCTTTATATAGCATGGGGCTAGCACACCT
NDV HN  texas (M21409)(120) TAGCTACATCTGTAGCCTCCCTTGTATATAGCATGGGGCTAGCACACCT
NDV HN  CA02 (EF520717)(110)TAGCTATCTCTGTAGCCGCCCCTGGTATAGAGCATGAAGCTAGCACGCCG
NDV HN  MEX (AY288999)(110) TAGCTATCTCTGTAGCCGCCCCTGGTATAGAGCATGGAGGCTAGCACACCG 251                                             300
NDV HN  (FJ608369)    (160) CACGAGCTCGCAGGCATAACGACTGTGATGTCTAAGACAGAAGATAAGGT
NDV HN  (ZJ1 strain)  (160) CACGATCTCGTAGGCATATCGACTGTGATGTCAAGACAGAAGATAAGGT
NDV HN LaSota (M24709)(251) AGCGATCTTGTAGGCATACCGACTAGGATTTCAAGGGCAGAAGAAAAGAT
NDV HN  texas (M21409)(170) AGCGATCTTGTAGGCATACCGACCAGGATTTCAAGGGCAGAAGAAAAGAT
NDV HN  CA02 (EF520717)(160)AACGACCTTGCGGGTATATCGACGGTGATGTCAAGGCAGAGATAGGGT
NDV HN  MEX (AY288999)(160) AACGACCTTGCGGGCATATCGACGGTGATGTCAAGGCAGAGATAGGGT 301                                             350
NDV HN  (FJ608369)    (210) TACGTCTTTACTCAGTTGAGTCAAGATGTAATAGATAGCATATACAAGC
NDV HN  (ZJ1 strain)  (210) TACATCTTTACTCAGTTTGAGTCAAGATGTAATAGATAAGATATACAAGC
NDV HN LaSota (M24709)(301) TACATCTACACTTGGTTCAATCAAGATGTAGTAGATAGATATATAAGC
NDV HN  texas (M21409)(220) TACATCTGCACTTGGTTCAATCAAGATGTAGTAGATAGATATATAAGC
NDV HN  CA02 (EF520717)(210)TACATCTTTACTCAATTCAAATCAAGATGTGGTAGATAGGGTATATAAAC
NDV HN  MEX (AY288999)(210) TACATCTTTACTCAATTCAAATCAAGATGTGGTAGATAGGGTATATAAAC 351                                             400
NDV HN  (FJ608369)    (260) AGGTGGCTCTTGAATCGCCAGTGGCGCTACTAAACACTGAATCATGATT
NDV HN  (ZJ1 strain)  (260) AGGTGGCTCTTGAATCGCCGGTGGCGCTACTAAACACTGAATCATAATT
NDV HN LaSota (M24709)(351) AAGTGGCGCTTGAGTCTCGTTGGCATTGTTAAAAACTGAGACCACAATT
NDV HN  texas (M21409)(270) AAGTGGCGCTTGAGTCTCGTTGGCATTGTTAAAAACTGAGACTACAATT
NDV HN  CA02 (EF520717)(260)AGGTGGCGCTTGAGTCGCCGCTGGCGTTGTTGAATACTGAGCTATAATT
NDV HN  MEX (AY288999)(260) AGGTGGCGCTTGAGTCGCCGCTGGCGTTGTTGAATACTGAGCTATAATT
```

Figure 7.1B

```
                              401                                                450
NDV HN (FJ608369)       (310) ATGAAGCAATAACCTCTCTTTCTTATCAAATTAACGGGGCTGCAACAA
NDV HN (ZJ1 strain)     (310) ATGAAGCAATAACCTCTCTTTCTTATCAAATTAACGGGGCTGCAACAA
NDV HN LaSota (M24709)  (401) ATGAACGCAATAACATCTCTCTTATCAGATTAAGGGAGCTGCAAACAA
NDV HN texas (M21409)   (320) ATGAACGCAATAACATCTCTCTTATCAGATTAAGGAGCTGCAACAA
NDV HN CA02 (EF520717)  (310) ATGAAGGCAATAACTTCTCTTTCCTATCAAATTAAGGGGCTGCAAATAG
NDV HN MEX (AY288999 )  (310) ATGAAGGCAATAACTTCTCTTTCCTATCAAATTAAGGGGCTGCAAATAG 451                                                500
NDV HN (FJ608369)       (360) GAGCGGATGTGGGGCGCCTGTTCATGACCCAGATTATATGGGGGGATAG
NDV HN (ZJ1 strain)     (360) GAGCGGATGTGGGGCGCCTGTTCATGACCCAGATTATATGGGGGGATAG
NDV HN LaSota (M24709)  (451) CAGCGGGTGGGGGGCACCTATCCATGACCCAGATTATATAGGGGGGATAG
NDV HN texas (M21409)   (370) CAGCGGGTGGGGGCACCTATCCATGACCCAGATTTATGGGGGGATAG
NDV HN CA02 (EF520717)  (360) GAGTGGGTGTGGGGCACCTGTTCATGACCCGGATTATATTGGGGGGGTAG
NDV HN MEX (AY288999 )  (360) GAGTGGGTGTGGGGCACCTGTTCATGACCCGGATTATATTGGGGGGTAG 501                                                550
NDV HN (FJ608369)       (410) GCAAAGAACTCATAGTGGACGACATCAGTGATGTCACATCATTTTATCC
NDV HN (ZJ1 strain)     (410) GCAAAGAACTCATAGTGGACGACATCAGTGATGTCACATCATTTTATCC
NDV HN LaSota (M24709)  (501) GCAAAGAACTCATTGTAGATGATGCTAGTGATGTCACATCATTCTATCCC
NDV HN texas (M21409)   (420) GCAAAGAACTCATTGTAGATGATGCTAGTGATGTCACATCATTCTATCCC
NDV HN CA02 (EF520717)  (410) GTAAAGAGCTCATAGTAGATGACACGAGTGATGCCACTTCATTCTATCCG
NDV HN MEX (AY288999 )  (410) GTAAAGAGCTCATAGTAGATGACACAAGTGATGCCACTTCATTCTATCC 551                                                600
NDV HN (FJ608369)       (460) TCTGCATATCAAGAACAGTGAAATTTCATCCCGGCGCCTACTACAGGATC
NDV HN (ZJ1 strain)     (460) TCTGCATATCAAGAACAGTGAAATTTCATCCCGGCGCCTACTACAGGATC
NDV HN LaSota (M24709)  (551) TCTGCATTTCAAGAACATCTGAATTTTATCCCGGCGCCTACTACAGGATC
NDV HN texas (M21409)   (470) TCTGCATTTCAAGAACATGATAAGTTTATCCCGGCGCCTACTACAGGATC
NDV HN CA02 (EF520717)  (460) TCAGCATATCAAGAACAGCTGAACTTTATCCCGGCGCCCACCACAGGTTC
NDV HN MEX (AY288999 )  (460) TCAGCATATCAAGAACAGCTGAACTTTATCCCGGCGCCCACCACAGGATC 601                                                650
NDV HN (FJ608369)       (510) CGGTTGCAGTCGGATACCGTCATTTGACATGAGCACCACCCATTATTGTT
NDV HN (ZJ1 strain)     (510) CGGTTGCAGTCGGATACCGTCATTTGACATGAGCACCACCCATTATTGTT
NDV HN LaSota (M24709)  (601) AGGTTGCAGTCGAATACCGTCATTGACATGAGTGCTACCCATTACTGCT
NDV HN texas (M21409)   (520) AGGTTGCATTCGGATACCTTCATTGACATGAGTGCTACCCATTACTGCT
NDV HN CA02 (EF520717)  (510) AGGCTGCAGTCGGATACCGTCATTCGACATGAGCGCTACCCACTATTGTT
NDV HN MEX (AY288999 )  (510) AGGCTGCAGTCGGATACCGTCATTCGACATGAGCGCTACCCACTATTGTT 651                                                700
NDV HN (FJ608369)       (560) ATACTCAGAATGTGATACTATCCGGTTGCAGAGATCACTCACAGTCAGAT
NDV HN (ZJ1 strain)     (560) ATACTCAGAATGTGATACTATCCGGTTGCAGAGATCACTCACAGTCAGAT
NDV HN LaSota (M24709)  (651) ACACCCATAATGTAATATGTCTGGATGCAGAGATCACTCACATTCATAT
NDV HN texas (M21409)   (570) ACACTCATAATATAATACGTCTGGATGCAGAGATCACTCACAGTCATAT
NDV HN CA02 (EF520717)  (560) ATACTCAGAATGTGATATATCTGGCTGCAGAGATCACTCACAGTCAGAT
NDV HN MEX (AY288999 )  (560) ATACTCAGAATGTGATATATCTGGCTGCAGAGATCACTCACAGTCAGAT 701                                                750
NDV HN (FJ608369)       (610) CAATACTTAGCACTTGGTGTGCTTCGGACATCTGCAACAGGGAGGTATT
NDV HN (ZJ1 strain)     (610) CAATACTTAGCACTTGGTGTGCTTCGGACATCTGCAACAGGGAGGTATT
NDV HN LaSota (M24709)  (701) CAGTATTAGCACTTGGTGTGCTCCGGACATCTGCAACAGGGAGGGTATT
NDV HN texas (M21409)   (620) CAGTATTAGCACTTGGTGTGCTCCGGACTTCTGCAACAGGGAGGATATT
NDV HN CA02 (EF520717)  (610) CAGTATTGGCACTAGGTGTGCTTCGGACATCTGCAACAGGGAGGGTATT
NDV HN MEX (AY288999 )  (610) CAGTATTGGCACTAGGTGTGCTTCGGACATCTGCAACAGGGAGGGTATT 751                                                800
NDV HN (FJ608369)       (660) CTTTTCTACTCTGCGCTCCATCAATTTAGATGACACCCAAAATCGGAAGT
NDV HN (ZJ1 strain)     (660) CTTTTCTACTCTGCGCTCCACCAATTTAGATGACACCCAAAATCGGAAGT
NDV HN LaSota (M24709)  (751) CTTTTCTACTCTGCGTTCCATCAACCTGGACGACACCCAAAATCGGAAGT
NDV HN texas (M21409)   (670) CTTTTCTACTCTGCGTTCCATCAATCTGGATGACACCCAGAATCGGAAGT
NDV HN CA02 (EF520717)  (660) CTTTTCTACTCTGCGTTCCATCAATTTAGATGACACCCAAAATCGGAAGT
NDV HN MEX (AY288999 )  (660) CTTTTCTACTCTGCGTTCCATCAATTTAGATGACACCCAAAATCGGAAGT
```

Figure 7.1C

|  |  | 801 | 850 |
| --- | --- | --- | --- |
| NDV HN (FJ608369) | (710) | CCTGCAGTGTGAGTGCAACCGCTTTAGGTTGTGATATGCTGTGCTCTAAG |
| NDV HN (ZJ1 strain) | (710) | CCTGCAGTGTGAGTGCAACCGCTTTAGGTTGTGATATGCTGTGCTCTAAG |
| NDV HN LaSota (M24709) | (801) | CTTGCAGTGTGAGTGCAACTGCCCTGGGTTGTGATATGCTGTGCTCGAAA |
| NDV HN texas (M21409) | (720) | CTTGCAGTGTGAGTGCAACTGCCTTAGGTTGTGATATGCTGTGCTCGAAA |
| NDV HN CA02 (EF520717) | (710) | CTTGCAGTGTGAGTGCAACTGCTTTAGGTTGTGATATGCTGTGCTCTAAA |
| NDV HN MEX (AY288999) | (710) | CTTGCAGTGTGAGTGCAACTTCTTTAGGTTGTGATATGCTGTGCTCTAAA |

851 900
NDV HN (FJ608369) (760) GTCACAGGGACTGAAGAGGAGGATTACAAGTCAGTTGCCCCGACACCAAT
NDV HN (ZJ1 strain) (760) GTCACAGAGACTGAAGAGGAGGATTACAAGTCAGTTGCCCCGACATCAAT
NDV HN LaSota (M24709) (851) GTCACGGAGACAGAGGAAGAAGATTATAACTCAGCTGTCCCTACGCGGAT
NDV HN texas (M21409) (770) GTCACGGAGACAGAGGAAGAAGATTATAACTCAGCTGTCCCTACGCTGAT
NDV HN CA02 (EF520717) (760) GTCACAGAGACTGAGGAGGAGGATTATAAGTCAGTTACCCCGACATCAAT
NDV HN MEX (AY288999) (760) GTCACAGAGACTGAGGAGGAGGATTATAAGTCAGTTACCCCGACATCAAT 901 950
NDV HN (FJ608369) (810) GGTGCACGGAAGGCTAGGGTTTGACGGTCAATACCATGAGAAGGACTTAG
NDV HN (ZJ1 strain) (810) GGTGCACGGAAGGCTAGGGTTTGACGGTCAATACCATGAGAAGGACTTAG
NDV HN LaSota (M24709) (901) GGCACATGGGAGGTTAGGGTTCGACGGCCAATACCACGAAAAGGACCTAG
NDV HN texas (M21409) (820) GGTACATGGGAGGTTAGGGTTCGACGGCCAATACCACGAAAAGGACCTAG
NDV HN CA02 (EF520717) (810) GGTGCATGGAAGGTTAGGGTTTGACGGTCAGTACCATGAGAAGGACTTAG
NDV HN MEX (AY288999) (810) GGTGCATGGAAGGTTAGGGTTTGACGGTCAGTACCATGAGAAGGACTTAG 951 1000
NDV HN (FJ608369) (860) ACACCACGGTCTTATTTAAGGATTGGGTGGCAAATTACCCAGGAGTGGGA
NDV HN (ZJ1 strain) (860) ACACCACGGTCTTATTTAAGGATTGGGTGGCAAATTACCCAGGAGCGGGA
NDV HN LaSota (M24709) (951) ATGTCACAACATTATTCGGGGACTGGGTGGCCAACTACCCAGGAGTAGGG
NDV HN texas (M21409) (870) ACGTCACAACATTATTTGAGGACTGGGTGGCCAACTACCCAGGAGTAGGG
NDV HN CA02 (EF520717) (860) ACGTCACAGTCTTATTTAAGGATTGGGTTGCAAATTACCCGGGAGTGGGA
NDV HN MEX (AY288999) (860) ACGTCACAGTCTTATTTAAGGATTGGGTTGCAAATTACCCGGGAGTGGGA 1001 1050
NDV HN (FJ608369) (910) GGAGGTCTTTTATTGACAACCGTGTATGGTTCCAGTTTAGGAGGGCT
NDV HN (ZJ1 strain) (910) GGAGGTCTTTTATTGACGACCGTGTATGGTTCCAGTTTAGGAGGGCT
NDV HN LaSota (M24709) (1001) GGTGAACTTTTATTGACGGCCGCGTATGGTTCTCAGTCTAGGGAGGGCT
NDV HN texas (M21409) (920) GGTGGATCTTTATTGACAGCCGCGTATGGTTCTCAGTCTAGGGAGGGCT
NDV HN CA02 (EF520717) (910) GGAGGTTCTCTTATTGACGACCGTGTATGGTTCCAGTTTATGAGGGCT
NDV HN MEX (AY288999) (910) GGAGGGTCTCTTATTGACGACCGTGTATGGTTCCAGTTTAGGCGGGCT 1051 1100
NDV HN (FJ608369) (960) CAAACCCAATTCACCGAGTGACACTGCACAAGAAGGGAAATATGTAATAT
NDV HN (ZJ1 strain) (960) CAAACCCAATTCACCCAGTGACACTGCACAAGAAGGGAAATATGTAATAT
NDV HN LaSota (M24709) (1051) GAAACCCAATTCACCGAGTGACACTGTACAGGAAGGGAAATATGTGATAT
NDV HN texas (M21409) (970) GAAACCCAATTCACCGAGTGACACTGTACAGGAAGAGAAATATGTAATAT
NDV HN CA02 (EF520717) (960) AAAACCCAATTCACCCTAGCGACACTGCACAAGAAGGGAAATATGTAATAT
NDV HN MEX (AY288999) (960) AAAACCCAATTCGCCTAGCGACACTGCACAAGAAGGGAAATATGTAATAT 1101 1150
NDV HN (FJ608369) (1010) ATAAGCGCCATAACAACACATGCCCGGATAAACAAGATTACCAATTCGG
NDV HN (ZJ1 strain) (1010) AGAAGCGGCATAACAACACATGCCCTGATGAACAAGATTACCAAATTCGG
NDV HN LaSota (M24709) (1101) ACAAGCGATACAATGACACATGCCCAGATGAGCAAGACTACCAGATTCGA
NDV HN texas (M21409) (1020) ACAAGCGATACAATGACACATGCCCAGATGAGCAAGACTACCAGATCCGA
NDV HN CA02 (EF520717) (1010) ACAAGCGCTATAATAACACATGCCCCGATGAACAAGATTACCAAGTTCGG
NDV HN MEX (AY288999) (1010) ACAAGCGCTATAATAACACATGCCCCGATGAACAAGATTACCAAGTTCGG 1151 1200
NDV HN (FJ608369) (1060) ATGGCTAAGTCTTCATATAAACCCGGCGATTGGTGGAAAGCGCTACA
NDV HN (ZJ1 strain) (1060) ATGGCTAAGTCTTCATATAAACCCGGCGATTGGTGGAAAGCGCTACA
NDV HN LaSota (M24709) (1151) ATGGCCAGTCTTCGTATAAGCCTGGACGGTTTGGTGGGAAACGCATCCA
NDV HN texas (M21409) (1070) ATGGCCAAGTCTTCGTATAAGCCCGGACGGTTTGGTGGAAAACGCATACA
NDV HN CA02 (EF520717) (1060) ATGGCTAAATCCTCGTATAAGCCGGACGGTTTGGTGGAAGCGCGTACA
NDV HN MEX (AY288999) (1060) ATGGCGAAGTCCTCGTATAAGCCGGACGGTTTGGTGGAAGCGCGTACA

Figure 7.1D

```
                                    1201                                              1250
NDV HN (FJ608369)      (1110)  GCAAGCGATCCTATCCATCAAAGTGTCAACATCCTTGGGTAAGGACCCGG
NDV HN (ZJ1 strain)    (1110)  GCAAGCGATCCTATCCATCAAAGTGTCAACATCCTTGGGTAAGGACCCGG
NDV HN LaSota (M24709) (1201)  GCAGGCTATCTTATCTATCAAGGTGTCAACATCCTTAGGGGAAGACCCGG
NDV HN texas (M21409)  (1120)  GCAGGCTATCTTATCTATCAAGGTGTCAACATCTTTGGGGGAAGACCCAG
NDV HN CA02 (EF520717) (1110)  GCAAGCGATCCTATCTATCAAAGTATCAACATCTTTGGGCGAGGACCCGG
NDV HN MEX (AY288999)  (1110)  GCAAGCGATCCTATCTATCAAAGTATCAACATCTTTGGGCGAGGACCCGG 1251                                              1300
NDV HN (FJ608369)      (1160)  TGCTGACTATTCCACCTAAAACAATCACACTCATGGGAGCCGAAGGCAGA
NDV HN (ZJ1 strain)    (1160)  TGCTGACTATTCCACCTAAAACAATCACACTCATGGGAGCCGAAGGCAGA
NDV HN LaSota (M24709) (1251)  TACTGACTGTACCGCCCAACACAGTCACACTCATGGGGGCCGAAGGCAGA
NDV HN texas (M21409)  (1170)  TACTGACTGTACCGCCCAACACAGTCACACTCATGGGGGCCGAAGGCAGA
NDV HN CA02 (EF520717) (1160)  TGCTGACTGTACCGCCAAAACAGTTACACTCATGGGGGCCGAGGGCAGA
NDV HN MEX (AY288999)  (1160)  TGCTGACTGTACCGCCAAAACAGTTACACTCATGGGGGCCGAAGGCAGA 1301                                              1350
NDV HN (FJ608369)      (1210)  ATCCTCACAGTAGGGACATCTCACTTCTTGTAGCAACGAGGGTCTTCATA
NDV HN (ZJ1 strain)    (1210)  ATCCTCACAGTAGGGACATCTCACTTCTTGTAGCAACGAGGGTCTTCATA
NDV HN LaSota (M24709) (1301)  ATTCTCACAGTAGGGACATCTCATTTCTTGTATCAACGAGGGTCATCATA
NDV HN texas (M21409)  (1220)  ATTCTCACAGTAGGGACATCTCATTTCTTGTATCAGCGAGGGTCATCATA
NDV HN CA02 (EF520717) (1210)  ATCCTCACAGTAGGAACATCTCATTTCTTGTAGCAGCGAGGGTCTTCATA
NDV HN MEX (AY288999)  (1210)  ATCCTCACAGTAGGAACATCTCATTTCTTGTAGCAGCGAGGGTCTTCATA 1351                                              1400
NDV HN (FJ608369)      (1260)  TTTGTCCCCGCCTTATTATATCCCATGACAGTAAATAACAAAACGGCTA
NDV HN (ZJ1 strain)    (1260)  TTTGTCCCCGCCTTATTATATCCCATGACAGTAAATAACAAAACGGCTA
NDV HN LaSota (M24709) (1351)  CTTGTCTCCCGCGTTATTATATCCTATGACAGTCAGCAACAAAACAGCCA
NDV HN texas (M21409)  (1270)  CTTGTCTCCCGCGTTATTATATCCTATGACAGTCAGCAACAAAACAGCCA
NDV HN CA02 (EF520717) (1260)  CTTTTCCCCCGCCTTACTATACCCTATGACAGTGCGCAACAAAACAGCCA
NDV HN MEX (AY288999)  (1260)  CTTTTCCCCGCCTTACTATACCCTATGACAGTGCGCAACAAAACAGCCA 1401                                              1450
NDV HN (FJ608369)      (1310)  CACTCCATAGTCCTTATACGTTTAATGCTTTCACTCGGCCAGGTAGTGCC
NDV HN (ZJ1 strain)    (1310)  CACTCCATAGTCCTTATACGTTTAATGCTTTCACTCGGCCAGGTAGTGTC
NDV HN LaSota (M24709) (1401)  CCCTTCATAGTCCTTATACATTCAATGCCTTCACTCGGCCAGGTAGTATC
NDV HN texas (M21409)  (1320)  CCCTTCATAGTCCCTATACATTCAATGCCTTCACTCGGCCAGGTAGTATC
NDV HN CA02 (EF520717) (1310)  CCCTTCATAGTCCTTATACATTTAATGCGTTCACTCGGCCGGGTAGTGTC
NDV HN MEX (AY288999)  (1310)  CCCTTCATAGTCCTTATACATTTAATGCGTTCACTCGGCCAGGTAGTGTC 1451                                              1500
NDV HN (FJ608369)      (1360)  CCTTGCCAGGCATCAGCAAGATGCCCGAACTCATGCATCACTGGAGTCTA
NDV HN (ZJ1 strain)    (1360)  CCTTGCCAGGCATCAGCAAGATGCCCGAACTCATGCATCACTGGGGTCTA
NDV HN LaSota (M24709) (1451)  CCTTGCCAGGCTTCAGCAAGATGCCCGAACCCGTGGTTACTGGAGTCTA
NDV HN texas (M21409)  (1370)  CCTTGCCAGGCTTCAGCAAGATGCCCGAACTCGTGGTTACTGGAGTCTA
NDV HN CA02 (EF520717) (1360)  CCTTGCCAGGCATCAGCAAGGTGCCCTAACTCATGTATCACTGGAGTCTA
NDV HN MEX (AY288999)  (1360)  CCTTGCCAGGCATCAGCAAGGTGCCCTAACTCATGTATCACTGGAGTCTA 1501                                              1550
NDV HN (FJ608369)      (1410)  TACTGATCCATATCCCTTAATCTTCCATAGGAAACATACTCTACGAGGGG
NDV HN (ZJ1 strain)    (1410)  TACTGATCCATATCCCTTAATCTTCCATAGGAAACATACTCTACGAGGGG
NDV HN LaSota (M24709) (1501)  TACAGATCCATATCCCTAATCTTCTATAGAAACCACACCTTGCGAGGGG
NDV HN texas (M21409)  (1420)  TACAGATCCATATCCCTAATCTTCTATAGAAACCACACCTTGCGAGGGG
NDV HN CA02 (EF520717) (1410)  TACTGATCCGTACCCTGTAGTCTTCCATAGGAAACACACCTTGCGAGGGG
NDV HN MEX (AY288999)  (1410)  TACTGATCCGTACCCTGTAGTCTTCCATAGGAAACACACCTTGCGAGGGG 1551                                              1600
NDV HN (FJ608369)      (1460)  TCTTCGGGACGATGCTTGATAATGAACAAGCGAGACTTAACCCGGTATCT
NDV HN (ZJ1 strain)    (1460)  TCTTCGGGACGATGCTTGATGATGAACAAGCGAGACTTAACCCGGTATCT
NDV HN LaSota (M24709) (1551)  TATTCGGGACAATGCTTGATGGTGTACAACAAGACTTAACCCTACGTCT
NDV HN texas (M21409)  (1470)  TATTCGGGACAATGCTTGATGGTGAACAAGAAGACTTAATCCTTCGTCT
NDV HN CA02 (EF520717) (1460)  TGTTCGGGACAATGCTTGATAATGAACAAGCAAGCTCAATCCGGTATCT
NDV HN MEX (AY288999)  (1460)  TGTTCGGGACAATGCTTGATAATGAACAAGCAAGCTCAATCCGGTATCT
```

Figure 7.1E

```
                                      1601                                             1650
NDV HN (FJ608369)      (1510)  GCAGTATTCGACAAACATATCCGCAGTCGTGTCACCCGGGTGAGTTCAAG
NDV HN (ZJ1 strain)    (1510)  GCAGTATTCGACAAACATATCCCGCAGTCGTGTCACCCGGGTGAGTTCAAG
NDV HN LaSota (M24709) (1601)  GCAGTATTCGATAGCAGATCCCGCAGTCGGATAACTCGAGTGAGTTCAAG
NDV HN texas (M21409)  (1520)  GCAGTATTCGATAGCAGATCCCGCAGTCGCATAACCCGAGTGAGTTCAAG
NDV HN CA02 (EF520717) (1510)  GCAATATTTGACTACACATCCCGCAGTCGCATAACCCGGGTAAGTTCGAC
NDV HN MEX (AY288999 ) (1510)  GCAATATTTGACTACACATCCCGCAGTCGCATAACCCGGGTAAGTTCGAT 1651                                             1700
NDV HN (FJ608369)      (1560)  CAGCACCAAGGCAGCATACACAACATCGACATGTTTTAAAGTGGTCAAGA
NDV HN (ZJ1 strain)    (1560)  CAGCACCAAGGCAGCATACACCACATCGACATGTTTAAAGTGGTCAAGA
NDV HN LaSota (M24709) (1651)  CAGCACCAAAGCAGCATACACAACATCAACTTGTTTTAAAGTGGTCAAGA
NDV HN texas (M21409)  (1570)  CAGCACCAAAGCAGCATACACAACATCAACTTGTTTTAAAGTGGTCAAGA
NDV HN CA02 (EF520717) (1560)  CAGCACCAAGGCAGCATACACCACATCGACATGTTTAAAGTGGTCAAGA
NDV HN MEX (AY288999 ) (1560)  CAGCACCAAGGCAGCATACACCACATCGACATGTTTTAAAGTGGTCAAGA 1701                                             1750
NDV HN (FJ608369)      (1610)  CCAATAAAGCTTATTGTCTCAGTATTGCAGAAATATCGAATACCCTATTC
NDV HN (ZJ1 strain)    (1610)  CCAATAAAACTTATTGTCTCAGTATTGCAGAAATATCGAATACCCTATTC
NDV HN LaSota (M24709) (1701)  CCAATAAGAGCTATTGTCTCAGCATTGCTGAAATATCTAATACCCTCTTC
NDV HN texas (M21409)  (1620)  CCAATAAGAGCTATTGTCTCAGCATTGCTGAAATATCTAATACCCTCTTC
NDV HN CA02 (EF520717) (1610)  CTAATAAAGTGTATTGTCTAGCATTGCAGAAATATCCAATACCCTATTT
NDV HN MEX (AY288999 ) (1610)  CCAATAAAGTGTATTGTCTAGCATTGCAGAAATATCCAATACCCTATTT 1751                                             1800
NDV HN (FJ608369)      (1660)  GGGGAATTTAGGATCGTCCCCTTATTAGTAGAGATCCTCAAGGATGATAG
NDV HN (ZJ1 strain)    (1660)  GGGGAATTTAGGATCGTCCCCTTATTAGTAGAGATCCTCAAGGATGATAG
NDV HN LaSota (M24709) (1751)  GGAGAATTCAGAATCGTCCCGTTACTAGTAGAGATCCTCAAAGATGACGG
NDV HN texas (M21409)  (1670)  GGAGAATTCAGAATCGTCCCGTTACTAGTAGAGATCCTCAAAAATGATGG
NDV HN CA02 (EF520717) (1660)  GGGGAATTCAGGATCGTCCCTTTACTGGTCGAGATTCTCAAAGATGATAG
NDV HN MEX (AY288999 ) (1660)  GGGGAATTCAGGATCGTCCCTTTACTGGTCGAGATTCTCAAGGATGATAG 1801                                             1850
NDV HN (FJ608369)      (1710)  AGTT---------------------------------------------
NDV HN (ZJ1 strain)    (1710)  AGTTTAA------------------------------------------
NDV HN LaSota (M24709) (1801)  GGTTAGAGAAGCCAGGTCTGGCTAGTTGAGTCAATTATAAAGGAGTTGGA
NDV HN texas (M21409)  (1720)  GGTTAGAGAAGCCAGGTCTGGTTAGTTGAGTCAACTATGAAAGAGCTGGA
NDV HN CA02 (EF520717) (1710)  GGTTTAA------------------------------------------
NDV HN MEX (AY288999 ) (1710)  GGTTTAA------------------------------------------

1851                                             1900
NDV HN (FJ608369)      (1714)  --------------------------------------------------
NDV HN (ZJ1 strain)    (1717)  --------------------------------------------------
NDV HN LaSota (M24709) (1851)  AAGATGGCATTGTATCACCTATCTTCTGCGACATCAAGAATCAAACCGAA
NDV HN texas (M21409)  (1770)  AAGATGGCATTGTATCACCTATCTTCCGCGACACCAAGAATCAAACTGAA
NDV HN CA02 (EF520717) (1717)  --------------------------------------------------
NDV HN MEX (AY288999 ) (1717)  --------------------------------------------------

1901                                             1950
NDV HN (FJ608369)      (1714)  --------------------------------------------------
NDV HN (ZJ1 strain)    (1717)  --------------------------------------------------
NDV HN LaSota (M24709) (1901)  TGCCGGCGCGTGCTCGAATTCCATGTTGCCAGTTGACCACAATCAGCCAG
NDV HN texas (M21409)  (1820)  TGCCGGTGCGAGCTCGAATTCCATGTCGCCAGTTGACCACAATCAGCCAG
NDV HN CA02 (EF520717) (1717)  --------------------------------------------------
NDV HN MEX (AY288999 ) (1717)  --------------------------------------------------

1951                                             2000
NDV HN (FJ608369)      (1714)  --------------------------------------------------
NDV HN (ZJ1 strain)    (1717)  --------------------------------------------------
NDV HN LaSota (M24709) (1951)  TGCTCATGCGATCAGATTAAGCCTTGTCAATAGTCTCTTGATTAAGAAAA
NDV HN texas (M21409)  (1870)  TGCTCATGCGATCAGATCAAGTCTTGTCAATAGTCCCTCGATTAAG----
NDV HN CA02 (EF520717) (1717)  --------------------------------------------------
NDV HN MEX (AY288999 ) (1717)  --------------------------------------------------
```

Figure 7.1F

```
                              2001
    NDV HN (FJ608369)   (1714) --
    NDV HN (ZJ1 strain) (1717) --
    NDV HN LaSota (M24709) (2001) AA
    NDV HN texas (M21409)  (1916) --
    NDV HN CA02 (EF520717) (1717) --
    NDV HN MEX (AY288999 ) (1717) --
```

NDV HN CA02 (EF520717):      SEQ ID NO:2
NDV HN MEX (AY288999):       SEQ ID NO:8
NDV HN LaSota (M24709):      SEQ ID NO:6
NDV HN texas (M21409):       SEQ ID NO:4
NDV HN (FJ608369):           SEQ ID NO:16
NDV HN (ZJ1 strain):         SEQ ID NO:18

Sequence identity percentage:

| SEQ ID NO: | 2   | 4     | 6     | 8     | 16    | 18    |
|------------|-----|-------|-------|-------|-------|-------|
| 2          | 100 | 83.9% | 83.5% | 98.9% | 87.2% | 87.9% |
| 4          |     | 100   | 83.8% | 84.2% | 82.8% | 82.9% |
| 6          |     |       | 100   | 96.3% | 82.1% | 82.2% |
| 8          |     |       |       | 100   | 87.5% | 88.2% |
| 16         |     |       |       |       | 100   | 98.4% |
| 18         |     |       |       |       |       | 100   |

Vector NTI 11.0 (PC) software package (Invitrogen, 1600 Faraday Ave., Carlsbad, CA).

Figure 7.2A

Alignment of SEQ ID NO:1 and SEQ ID NO:2

```
                            1                                                  50
SEQ ID NO:1     (1)    ATGGACCGTGTCGTCTCCCGCGTGGTCCTCGAGAACGAGGAGCGTGAGGC
SEQ ID NO:2     (1)    ATGGATCGTGTAGTTAGCAGAGTCGTACTAGAAAACGAAGAAAGAGAAGC
                           51                                                 100
SEQ ID NO:1    (51)    CAAGAACACCTGGCGCCTTGTCTTTCGTGTCGCCGTCCTCTCCCTTATTG
SEQ ID NO:2    (51)    AAAGAATACATGGCGCCTGGTTTTCCGGTCGCAGTCCTATCTCTAATAG
                          101                                                 150
SEQ ID NO:1   (101)    TCATGACCCTCGCCATCTCCGTCGCCGCCCTCGTCTACAGCATGGAGGCT
SEQ ID NO:2   (101)    TAATGACATTAGCTATCTCTGTAGCCGCCCTGGTATACAGCATGGAGGCT
                          151                                                 200
SEQ ID NO:1   (151)    AGCACCCCCAACGATCTCGCCGGAATCTCGACTGTTATCTCCCGCGCCGA
SEQ ID NO:2   (151)    AGCACGCCGAACGACCTTGCGGGTATATCGACGGTGATCTCCAGGGCAGA
                          201                                                 250
SEQ ID NO:1   (201)    GGACCGCGTCACCTCCCTCCTCAACTCCAACCAGGATGTCGTTGATCGCG
SEQ ID NO:2   (201)    GGATAGGTTACATCTTTACTCAATTCAAATCAAGATGTGGTAGATAGGG
                          251                                                 300
SEQ ID NO:1   (251)    TCTACAAGCAGGTCGCCCTCGAGTCCCTCTCGCCCTCCTTAACACCGAG
SEQ ID NO:2   (251)    TATATAAACAGGTGGCCCTTGAGTCCCCGCTGGCGTTGTTGAATACTGAG
                          301                                                 350
SEQ ID NO:1   (301)    AGCATCATTATGAACGCCATTACCTCCCTCAGCTACCAGATTAACGGCGC
SEQ ID NO:2   (301)    TCTATAATTATGAATGCAATAACTTCTCTTTCCTATCAAATTAATGGGGC
                          351                                                 400
SEQ ID NO:1   (351)    CGCCAACTCGTCCGGCTGCGGCGCCCCGTCCATGACCCTGATTACATCG
SEQ ID NO:2   (351)    TGCAAATAGTAGTGGGTGTGGGCACCTGTTCATGACCCGGATTATATTG
                          401                                                 450
SEQ ID NO:1   (401)    GCGGCGTCGGCAAGCAGCTCATCGTCGACGACACTAGCGATGCCACGTCC
SEQ ID NO:2   (401)    GGGGGTAGGTAAAGAGCTCATAGTAGATGACACGAGTGATGCCACTTCA
                          451                                                 500
SEQ ID NO:1   (451)    TTCTACCCTAGCGCCTACCAGGAGCACCTCAACTTCATCCCTGCCGTCCAC
SEQ ID NO:2   (451)    TTCTATCCTTCAGCATATCAAGAACACCTGAACTTTATCCCGGCGCCCAC
                          501                                                 550
SEQ ID NO:1   (501)    TACCGGCTCCGGCTGCACCCGCATTCCAGCTTCGACATGTCCGCCACTC
SEQ ID NO:2   (501)    CACAGGTTCAGGCTGCACTCGGATACCCTCATTCGACATGAGCGCTACCC
                          551                                                 600
SEQ ID NO:1   (551)    ACTACTGCTACACCCATAACGTCATCCTTTCGGGTTGCCGCGACCACTCC
SEQ ID NO:2   (551)    ACTATTGTTATACTCACAATGTGATATTATCTGGCTGCAGAGATCACTCA
                          601                                                 650
SEQ ID NO:1   (601)    CACAGCCACCAGTACCTCGCCCTCGGAGTTCTTCGTACGTCCGCCACCGG
SEQ ID NO:2   (601)    CACTCACATCAGTATTTGGCACTAGGTGTGCTTCGACATCTGCAACAGG
                          651                                                 700
SEQ ID NO:1   (651)    CCGCGTCTTTTTTTCCACCCTCCGCAGCATCAACCTCGACGATACCCAGA
SEQ ID NO:2   (651)    GAGGTATTCTTTTCTACTCTGCGTTCCATCAATTTAGATGACACCCAAA
                          701                                                 750
SEQ ID NO:1   (701)    ACCGCAAGAGCTGCTCGGTCTCCGCCACCCCGCTCGGCTGCGACATGCTC
SEQ ID NO:2   (701)    ATCGGAAGTCTTGCAGTGTGAGTGCAACTCCTTTAGGTTGTGATATGCTG
                          751                                                 800
SEQ ID NO:1   (751)    TGCTCCAAGGTCACCGAGACGGAGGAGGAGGATTACAAGTCCGTTACCCC
SEQ ID NO:2   (751)    TGCTCTAAAGTCACAGAGACTGAGGAGGAGGATTATAAGTCAGTTACCCC
                          801                                                 850
SEQ ID NO:1   (801)    CACTTCGATGGTCCACGGCCGCCTTGGCTTCGACGGCCAGTACCACGAGA
SEQ ID NO:2   (801)    CACATCAATGGTGCATGGAAAGGTTAGGGTTTGACGGTCAGTACCATGAGA
                          851                                                 900
SEQ ID NO:1   (851)    AGGACCTCGACGTCACCGTTCTCTTTAAGGACTGGGTTGCCAACTACCCC
SEQ ID NO:2   (851)    AGGACTTAGACGTCACAGTCTTATTTAAGGATTGGGTTGCAAATTACCCG
                          901                                                 950
SEQ ID NO:1   (901)    GGCGTCGCCGGCGGCTCCCTCATCGATGACCGCGTCTGGTTTCCTGTCTA
SEQ ID NO:2   (901)    GGAGTGGGAGGAGGTCTCTTATTGACGACCGTGTATGGTTCCCAGTTTA
                          951                                                1000
SEQ ID NO:1   (951)    CGGTGGTCTCAAGCCTAACAGCCCCTCCGATACCGCCCAGGAGGGTAAGT
SEQ ID NO:2   (951)    TGGAGGGCTAAAACCCAATTCACCTAGCGACACTGCACAAGAAGGGAAAT
```

Figure 7.2B

```
                        1001                                              1050
SEQ ID NO:1  (1001)  ACGTGATCTACAAGCGCTACAACAACACCTGCCCTGACGAGCAGGATTAC
SEQ ID NO:2  (1001)  ATGTAATATACAAGCGCTATAATAACACATGCCCCGATGAACAAGATTAC
                        1051                                              1100
SEQ ID NO:1  (1051)  CAGGTCCGCATGGCCAAGTCCTCGTACAAGCCCGGTCGTTTCGGCGGCAA
SEQ ID NO:2  (1051)  CAAGTTCGGATGGCTAAATCCTCGTATAAGCCTGGACGGTTTGGTGGGAA
                        1101                                              1150
SEQ ID NO:1  (1101)  GCGCGTCCAGCAGGCCATTCTCTCGATCAAGGTCTCGACCAGCCTCGGAG
SEQ ID NO:2  (1101)  GCGCGTACAGCAAGCCATCCTATCTATCAAAGTATCAACATCTTTGGGCG
                        1151                                              1200
SEQ ID NO:1  (1151)  AGGACCCCGTGCTCACCGTTCCCCCTAACACCGTCACCCTTATGGGCGCC
SEQ ID NO:2  (1151)  AGGACCCGGTGCTGACTGTACCGCCAAATACAGTTACACTCATGGGGGCC
                        1201                                              1250
SEQ ID NO:1  (1201)  GAGGGCCGCATCCTCACCGTCGGTACCTCCCACTTCCTCTACCAGCGCGG
SEQ ID NO:2  (1201)  GAGGGCAGAATCCTCACAGTAGGAACATCTCATTTCTTGTACCAGCGAGG
                        1251                                              1300
SEQ ID NO:1  (1251)  CTCGAGCTACTTTTCCCCTGCCCTTCTTTACCCATGACTGTTCGCAACA
SEQ ID NO:2  (1251)  GTCTTCATACTTTTCTCCCGCCTTACTATACCCTATGACAGTGCGCAACA
                        1301                                              1350
SEQ ID NO:1  (1301)  AGACTGCTACCCTCCACAGCCCCTACACCTTTAACGCCTTCACGCGCCCC
SEQ ID NO:2  (1301)  AAACAGCCACTCTTCATAGTCCTTATACATTTAATGCGTTCACTCGGCCG
                        1351                                              1400
SEQ ID NO:1  (1351)  GGAAGCGTCCCCTGCCAGGCGAGCGCCCGCTGCCCTAACTCCTGCATTAC
SEQ ID NO:2  (1351)  GGTAGTGTCCCTTGCCAGGCATCAGCAAGGTGCCCTAACTCATGTATCAC
                        1401                                              1450
SEQ ID NO:1  (1401)  CGGCGTCTACACCGACCCTTACCCTGTCGTCTTTCACCGCAACCATACCC
SEQ ID NO:2  (1401)  TGGAGTCTATACTGATCCGTACCCTGTAGTCTTCCATAGGAATCACACCT
                        1451                                              1500
SEQ ID NO:1  (1451)  TTCGCGGCGTCTTCGGTACTATGCTTGATAACGAGCAGGCCCGCCTCAAC
SEQ ID NO:2  (1451)  TGCGAGGGTGTTCGGACAATGCTTGATAATGAACAAGCAAGGCTCAAT
                        1501                                              1550
SEQ ID NO:1  (1501)  CCCGTCTCCGCCATTTTCGACTACACTTCCCGCTCCCGTATCACCCGCGT
SEQ ID NO:2  (1501)  CCCGTATCTGCAATATTTGACTACACATCTCGCAGTCGCATAACCCGGGT
                        1551                                              1600
SEQ ID NO:1  (1551)  CTCCTCCACCTCCACCAAGGCCGCCTACACCACCTCCACCTGCTTTAAGG
SEQ ID NO:2  (1551)  AAGTTCGACCAGCACCAAGGCAGCATACACGACATCGACATGTTTAAAG
                        1601                                              1650
SEQ ID NO:1  (1601)  TTGTCAAGACTAACAAGGTCTACTGCCTCTCCATCGCCAGATTAGCAAC
SEQ ID NO:2  (1601)  TTGTCAAGACTAATAAAGTGTATTGTCTTAGCATTGCAGAAATATCCAAT
                        1651                                              1700
SEQ ID NO:1  (1651)  ACCCTCTTCGGAGAGTTCCGCATTGTCCCCCTGCTCGTCGAGATCCTCAA
SEQ ID NO:2  (1651)  ACTCTATTTGGGGAATTCAGGATCGTTCCTTTACTGGTCGAGATTCTCAA
                        1701       1716
SEQ ID NO:1  (1701)  GGACGATCGCGTTTAA
SEQ ID NO:2  (1701)  AGATGATAGGGTTTAA
```

Sequence identity percentage between SEQ ID NOs:1 and 2: 72.4%

Figure 7.2C

Alignment of SEQ ID NO:16 and SEQ ID NO:22

```
                        1                                                  50
SEQ ID NO:16     (1)    ATGGGACGCGGGTTAACAGAGTCGCGCTGGAGAATGAGGAAAGAGAAGC
SEQ ID NO:22     (1)    ATGGGCCGGCCGTCAACCGCGTGGCGTTGGAGAACGAGGAGCGGAGGC
                        51                                                 100
SEQ ID NO:16    (51)    AAAGAACACATGGCGCCTGGTTTTCCGATCGCAGTCTTACTTTTAATGG
SEQ ID NO:22    (51)    CAAGAACACCTGGAGGCTCGTGTTCCGCATCGCCGTGCTCCTGCTCATGG
                        101                                                150
SEQ ID NO:16   (101)    TAATGACTCTAGCTATCTCCGCAGCTGCCCTGGCATACAGTGCGGGGGCC
SEQ ID NO:22   (101)    TCATGACCCTGGCGATCTGGCCGCGGCCCTGGCCTACTCCGCCGGTGCG
                        151                                                200
SEQ ID NO:16   (151)    AGTACGCCGCACGACCTCGCAGGCATATCGACTGTGATCTCTAAGACAGA
SEQ ID NO:22   (151)    AGCACCCGCACGACCTGGCCGGGATCAGCACCGTCATCTTGAAGACCGA
                        201                                                250
SEQ ID NO:16   (201)    GGATAAGGTTACGTCTTTACTCAGTTCAGTCAAGATGTGATAAATAAGA
SEQ ID NO:22   (201)    GGACAAGGTGACGTCCCTGCTCAGCTCGTCCAGGACGTTATCGACCGCA
                        251                                                300
SEQ ID NO:16   (251)    TATACAAGCAGGTGGCTCTTGAATCCCCACTGGCGCTACTAAACACTGAA
SEQ ID NO:22   (251)    TCTACAAGCAAGTCGGCTTGGAGAGCCCTTCTGGCCCTGCTCAACACGGAG
                        301                                                350
SEQ ID NO:16   (301)    TCTATGATTATGAATGCAATAACCTCTCTTTCTTATCAAATAACGGGGC
SEQ ID NO:22   (301)    AGCATGATCATGAACGCGATCACCTCCTGAGCTACCAGATCAACGGGGC
                        351                                                400
SEQ ID NO:16   (351)    TGCGAACAATAGCGAATGTGGCGCCTTCATGACCCAGATTATATCG
SEQ ID NO:22   (351)    CGCGAACAATTCCGGGTGCGGCGCCCCCGTGCACGACCCTGACTACATCG
                        401                                                450
SEQ ID NO:16   (401)    GGGGATAGGCAAAGAACTCATAGTGGACGACATCAGTGATGTCACATCA
SEQ ID NO:22   (401)    GCGGGATCGGCAAGGAACTCATCGTTGACGACATCAGCGACGTGACGTCG
                        451                                                500
SEQ ID NO:16   (451)    TTTTATCCTTCTGCATATCAAGAACACTTGAATTTCATCCCGGCGCCTAC
SEQ ID NO:22   (451)    TTCTACCCCTCCGCCTACCAGGAGCACCTCAACTTCATCCCGCCCCGAC
                        501                                                550
SEQ ID NO:16   (501)    TACAGGATCCGGTTGCACTCGGATACCCTCATTGACATGAGCACCACCC
SEQ ID NO:22   (501)    CACGGGGAGCGGCTGCACCCGGATCCCGTCCTTCGACATGTCCACCACGC
                        551                                                600
SEQ ID NO:16   (551)    ATTATTGTTATACTCACAATGTGATACTATCCGGTTGCAGAGATCACTCA
SEQ ID NO:22   (551)    ACTATTGCTACACCCACAACGTGATCCTGTCGGGGTGCCGCGACCACAGC
                        601                                                650
SEQ ID NO:16   (601)    CACTCACATCAATACTTAGCACTTGGTGTGCTTCGGACATCTGCAACAGG
SEQ ID NO:22   (601)    CACTCGCACCAGTACCTGGCGCTGGGCGTCCTCAGGACCTCCGCGACCGG
                        651                                                700
SEQ ID NO:16   (651)    GAGGTATTCTTTTCTACTCTGCGCTCCATCAATTTAGATGACACCCAAA
SEQ ID NO:22   (651)    CCGCGTGTTCTTCTCCACTCTCCGCTCCATCAACCTGGACGATACGCAGA
                        701                                                750
SEQ ID NO:16   (701)    ATCGGAAGTCCTGCAGTGTGAGTGCAACCCCTTTAGGTTGTGATATGCTG
SEQ ID NO:22   (701)    ACCGCAAGTCCTGCAGCGTGTCCGCCACGCCCTCGGCTGCGACATGCTC
                        751                                                800
SEQ ID NO:16   (751)    TGCTCTAAGGTCACAGGGACTGAAGAGGAGGATTACAAGTCAGTTGCCCC
SEQ ID NO:22   (751)    TGCTCCAAGGTGACCGGCACCGAGGAGGAGGACTACAAGTCCGTGGCCCC
                        801                                                850
SEQ ID NO:16   (801)    CACACCAATGGTGCACGGAAGGCTAGGGTTTGACGGTCAATACCATGAGA
SEQ ID NO:22   (801)    CACCCCGATGGTGCACGGGCGGCTCGGCTTCGATGGTCAGTACCACGAGA
                        851                                                900
SEQ ID NO:16   (851)    AGGACTTAGACACCACGTTCTTATTTAAGGATTGGGTGCAAATTACCCA
SEQ ID NO:22   (851)    AGGACCTGGACACGACCGTGCTCTTCAAGGACTGGGTGGCGAACTACCCC
```

Figure 7.2D

```
                    901                                              950
SEQ ID NO:16   (901) GGAGTGGGAGGAGGGTCTTTTATTGACAACCGTGTATGGTTCCCAGTTTA
SEQ ID NO:22   (901) GGTGTGGGGGGCGGTAGCTTCATCGACAACAGAGTCTGGTTCCCCGTGTA
                    951                                             1000
SEQ ID NO:16   (951) CGGAGGGCTCAAACCCAATTCACCCAGTGACACTGCACAAGAAGGAAAAT
SEQ ID NO:22   (951) CGGGGGCCTGAAGCCCAACTCCCCCTCCGACACGGCCAGGAGGGGAAGT
                   1001                                             1050
SEQ ID NO:16  (1001) ATGTAATATATAAGCGCCATAACAACACATGCCCCGATAAACAAGATTAC
SEQ ID NO:22  (1001) ACGTCATCTACAAGCGGCACAACAACACCTGCCCGAACAAGCAGGACTAT
                   1051                                             1100
SEQ ID NO:16  (1051) CAAATTCGGATGGCTAAGTCTTCATATAAACCCGGCGATTTGGTGGAAA
SEQ ID NO:22  (1051) CAGATCCGGATGGCCAAAAGCTCCTACAAGCCCGCCGCTTCGGGGGCAA
                   1101                                             1150
SEQ ID NO:16  (1101) GCGCTACAGCAAGCCATCTTATCCATCAAAGTGTCAACATCCTTGGGTA
SEQ ID NO:22  (1101) GAGAGTCCAGCAGGCGATCCTCTCCATCAAGGTGAGCACGAGCCTCGGCA
                   1151                                             1200
SEQ ID NO:16  (1151) AGGACCCGGTGCTGACTATTCCACCTAATACAATCACACTCATGGGAGCC
SEQ ID NO:22  (1151) AGGACCCGGTCCTGACCATCCCCCGAACACCATCACCCTCATGGGCGCC
                   1201                                             1250
SEQ ID NO:16  (1201) GAAGGCAGAATCCTCACAGTAGGGACATCTCACTTCTTGTACCAACGAGG
SEQ ID NO:22  (1201) GAGGGAGAATCCTCACTGTCGGCACCTCCACTTCCTGTACCAGCGGGG
                   1251                                             1300
SEQ ID NO:16  (1251) GTCTTCATATTTCTCCCCTGCCTTATTATATCCATGACAGTAAATAACA
SEQ ID NO:22  (1251) CAGCTCGTACTTCAGCCCGGCGCTCCTGTACCCGATGACCGTCAACAACA
                   1301                                             1350
SEQ ID NO:16  (1301) AAACGGCTACACTCCATAGTCCTTATACGTTTAATGCTTTCACTCGGCCA
SEQ ID NO:22  (1301) AGACCGCCACGCTGCACTCGCCCTACACCTTCAACGCCTTCACCCGCCCC
                   1351                                             1400
SEQ ID NO:16  (1351) GGTAGTGCCCCTTGCCAGGCATCAGCAAGATGCCCCAACTCATGCATCAC
SEQ ID NO:22  (1351) GGCAGCGCCCCGTGCCAGGCCTCCGCCCGCTGCCCGAACTCGTGCATCAC
                   1401                                             1450
SEQ ID NO:16  (1401) TGGAGTCTATACTGATCCATATCCTTAATCTTCCATAGGAATCATACTC
SEQ ID NO:22  (1401) CGGGGTCTACACCGACCCTTACCCGCTGATCTTCCACCGCAACCACACGC
                   1451                                             1500
SEQ ID NO:16  (1451) TACGAGGGGTCTTCGGGACGATGCTTGATGATGAACAAGCGAGACTTAAC
SEQ ID NO:22  (1451) TCAGGGGGGTGTTCGGGACCATGCTCGACGACGAGCAGGCTCGCCTGAAC
                   1501                                             1550
SEQ ID NO:16  (1501) CCCGTATCTGCAGTATTCGACAACATATCCCGCAGTCGTGTCACCCGGGT
SEQ ID NO:22  (1501) CCCGTCAGCGCCGTCTTCGACAACATCTCCCGCAGCCGCGTCACGACAGT
                   1551                                             1600
SEQ ID NO:16  (1551) GAGTTCAAGCAGCACCAAGGCAGCATACACAACATGACATGTTTTAAAG
SEQ ID NO:22  (1551) CTCCTCGTCCTCGACGAAGGCCGCGTACACCACGTCCACCTGCTTCAAGG
                   1601                                             1650
SEQ ID NO:16  (1601) TTGTCAAGACCAATAAAGCTTATTGTCTTAGTATTGCAGAAATATCCAAT
SEQ ID NO:22  (1601) TGGTTAAGACCAACAAAGCCTACTGCCTCTCCATCGCTGAGATCTCCAAC
                   1651                                             1700
SEQ ID NO:16  (1651) ACCCTATTCGGGGAATTTAGGATCGTTCCCTTATTAGTTGAGATCCTCAA
SEQ ID NO:22  (1651) ACCCTCTTCGGCGAGTTCCGGATCGTGCCCCTCTTGGTGGAGATCCTGAA
                   1701     1713
SEQ ID NO:16  (1701) GGATGATAGAGTT
SEQ ID NO:22  (1701) GGACGACCGCGTG
```

The identity percentage between SEQ ID NO:16 and SEQ ID NO:22 is 73%.

Figure 7.3A
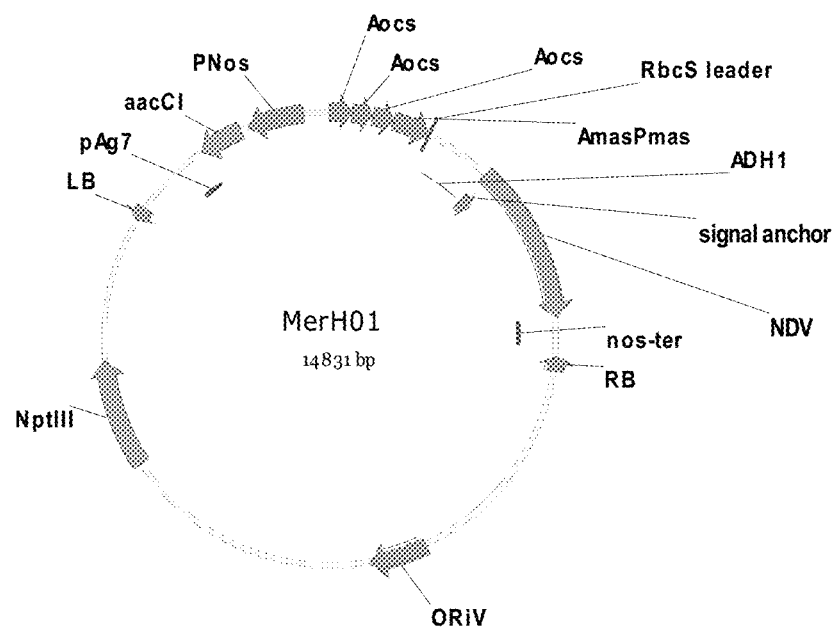
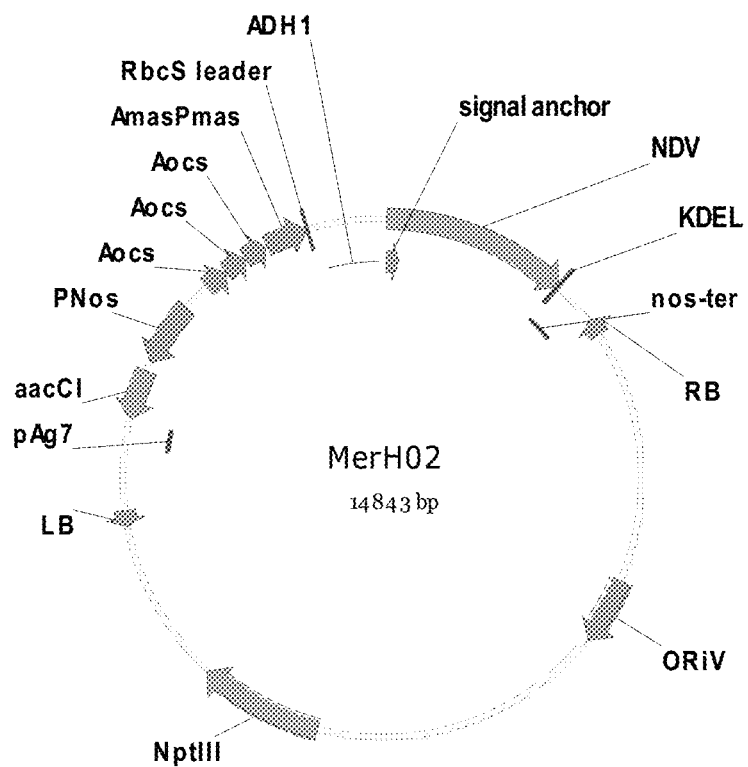

Figure 7.3B
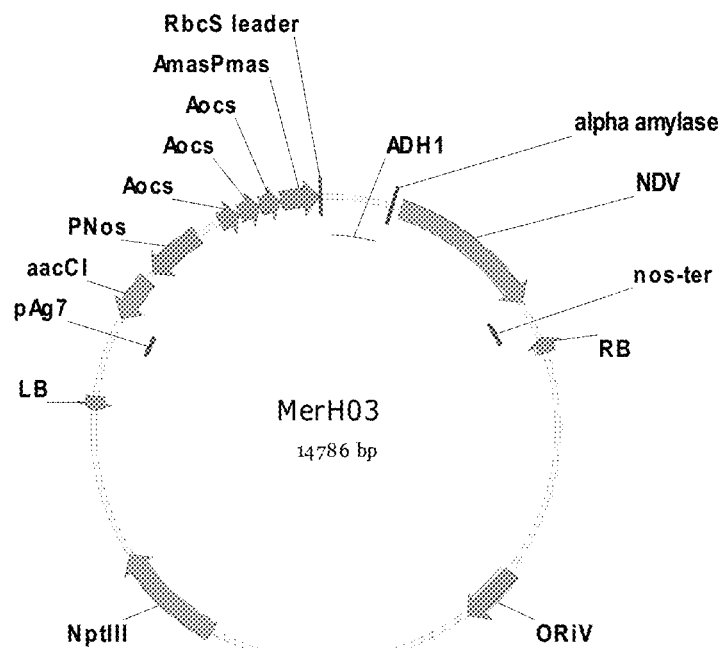
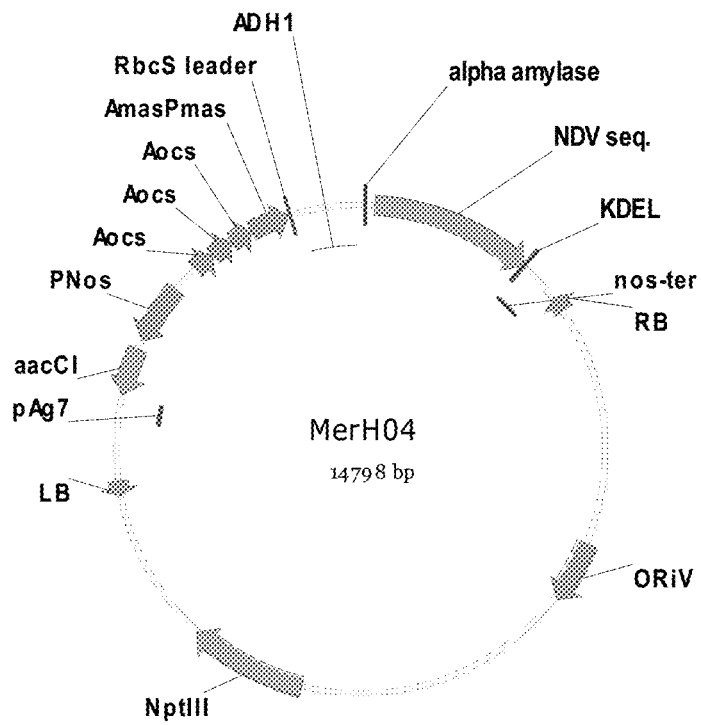

Figure 8

HN Linear Epitope Region (boxed region)

```
NDV HN - TX/GB (P12553)        (330) QEEKYVIYKR YNDTCPDEQD YQIRMAKSSY KPGRFGGKRI QQAILSIKVS
NDV HN LaSota (AAA46659)       (330) QEGKYVIYKR YNDTCPDEQD YQIRMAKSSY KPGRFGGKRI QQAILSIKVS
NDV HN CA/02 (ABS84265)        (330) QEGKYVIYKR YNNTCPDEQD YQVRMAKSSY KPGRFGGKRV QQAILSIKVS
NDV HN MEX/96 (AAQ54638)       (330) QEGKYVIYKR YNNTCPDEQD YQVRMAKSSY KPGRFGGKRV QQAILSIKVS
NDV HN Liaoning/08(ACM67348)   (330) QEGKYVIYKR HNNTCPDKQD YQIRMAKSSY KPGRFGGKRV QQAILSIKVS
NDV HN ZJ1 (AAL18936)          (330) QEGKYVIYKR HNNTCPDEQD YQIRMAKSSY KPGRFGGKRV QQAILSIKVS
```

The alignment shows the amino acids between position 330 and position 379 of below protein sequences:

NDV HN - TX/GB (P12553):        SEQ ID NO:5
NDV HN LaSota (AAA46659):       SEQ ID NO:7
NDV HN CA/02(ABS84265):         SEQ ID NO:3
NDV HN MEX/96 (AAQ54638):       SEQ ID NO:9
NDV HN Liaoning/08(ACM67348):   SEQ ID NO:17
NDV HN ZJ1 (AAL18936)           SEQ ID NO:19

NDV HN Linear Epitope Region 1 (SEQ ID NO:10): PDEQDYQIRMAKSS

NDV HN Linear Epitope Region 2 (SEQ ID NO:11): PDEQDYQVRMAKSS

NDV HN Linear Epitope Region 3 (SEQ ID NO: 28): PDKQDYQIRMAKSS

Figure 9

Location and Presence of Glycosylation Sites in NDV Strains

| Glycosylation Site* | Sequence | Glycosylation Site Presence by Strain | | |
|---|---|---|---|---|
| | | LaSota (SEQ ID NO:7) | CA/02 (SEQ ID NO:3) | TX/GB (SEQ ID NO:5) |
| 119 | NSS/NNS | X** | X | X |
| 341 | NNT/NDT | X | X | X |
| 433 | NKT | X | X | X |
| 481 | NHT | X | X | X |
| 508 | | | | |
| 538 | NKT | X | -*** | X |

*There are six potential sites for glycosylation. The glycosylation site is indicated at the amino acid position of the protein sequence.
** : presence of the glycosylation site
*** : absence of the glycosylation site.

Figure 10

Graphical Feature Map of the NDV HN Protein (SEQ ID NO:3)

```
                                          341 Glycosylation Site
                                                  433 Glycosylation Site
119 Glycosylation Site                    Linear Epitope    481 Glycosylation Site 571 aa
```

Figure 11

Peptide sequence analysis of expressed NDV HN (SEQ ID NO:3) in algae

Species: Newcastle disease virus
Name: Hemagglutinin-neuraminidase
Identified by 32 peptides covering 68% of the protein sequence.

Figure 12

HI titer at D27 against NDV La Sota Strain

[Bar chart showing HI titer Log 2 values:
- Algae WT: ~4.1
- Algae NDV HN 100HAU: ~5.1
- Algae NDV HN 1000HAU: ~8.0
- Algae NDV HN 9333HAU: ~7.1]

| Group | Mortality | Protection (%) |
|---|---|---|
| Algae WT | 12/12 | 0 |
| Algae NDV HN 100 HAU | 8/12 | 33 |
| Algae NDV HN 1000 HAU | 0/12 | 100 |
| Algae NDV HN 9333HAU | 0/12 | 100 |

RECOMBINANT NDV ANTIGEN AND USES THEREOF

CROSS-REFERENCE TO RELATED APPLICATIONS

This application claims benefit of U.S. provisional application Ser. No. 61/290,297 filed Dec. 28, 2009.

FIELD OF THE INVENTION

The present invention encompasses pharmaceutical compositions comprising an NDV antigen, in particular pharmaceutical compositions comprising NDV HN antigen.

BACKGROUND OF THE INVENTION

The virus family Paramyxoviridae includes both human (measles, mumps, paraNDV and respiratory syncytial virus) and animal pathogens (Newcastle disease virus and rinderpest virus) that cause significant impact on public health as well as the global economy (Lamb et al., 2007, Paramyxoviridae: The viruses and Their Replication, p. 1449-1496). Members of this virus family are defined by having a monopartite, negative sense, single-stranded RNA genome. The Paramyxoviridae family consists of two subfamilies namely Paramyxovirinae and Pneumovirinae. Owing to recent reclassification, the subfamily Paramyxovirinae includes five genera, i.e. Morbillivirus, Henipavirus, Rubulavirus, Respirovirus and Avulavirus while Pneumovirinae includes Pneumovirus and Metapneumovirus (Mayo, 2002, Arch Virol 147:1655-63). Avian paramyxoviruses (APMV) are classified in the genus Avulavirus and comprise nine antigenically distinct serotypes that have been defined using hemagglutination inhibition (HI) tests (Alexander, 1988, Newcastle disease, p. x, 378 p). Of the nine serotypes, isolates belonging to the APMV-1 subtype can cause a devastating disease in commercial poultry and are classified as velogenic Newcastle disease virus (NDV). Milder forms of NDV are designated as mesogenic and lentogenic isolates, wherein the latter form is mostly asymptomatic in domestic poultry. The genomic RNA of NDV contains genes encoding six proteins: HN (hemagglutinin-neuraminidase), NP (nucleocapsid protein), P (phosphoprotein), M (matrix protein), F (fusion protein), and L (RNA-dependent RNA polymerse).

Viral vector vaccines represent one of the most rapidly growing areas in vaccine development. Many vaccines in clinical development for major global infectious diseases, HIV, tuberculosis and malaria, are viral vectors. The disadvantage of currently used viral vectors is the existence of maternally derived antibodies or antibodies acquired due to a past infection.

Recently, plants and algae have been investigated as a source for the production of therapeutic agents such as vaccines, antibodies, and biopharmaceuticals. These plant and algae expression systems provide several advantages. For example, deriving vaccines from plant or algae expression products can eliminate the risk of contamination with animal pathogens, provide a heat-stable environment, and would avoid injection-related hazards if administered as an edible agent (Thanavala et al., Expert Rev. Vaccines 2006, 5, 249-260). In addition, plants or algae can be grown on a large scale and can utilize existing cultivation, harvest, and storage facilities. Furthermore, there is a lower cost of production and processing to derive therapeutic agents from plants (Giddings et al., Nature Biotech. 2000, 18, 1151-1155) or algae. The F and HN proteins of NDV were expressed in potato plants for developing edible vaccine against NDV (Berinstein A., et al., 2005, Vaccine 23: 5583-6689). WO2004/098533 discloses the expression of the NDV HN antigen and the Avian Influenza Virus HA antigen in tobacco plants. US patent application publication No. US2010/0189731 discloses the expression of Avian Influenza Virus HA antigen in duckweed plants.

Development of vaccines, antibodies, proteins, and biopharmaceuticals from plants or algae is far from a remedial process, and there are numerous obstacles that are commonly associated with such vaccine production. Limitations to successfully producing plant vaccines include low yield of the bioproduct or expressed antigen (Chargelegue et al., Trends in Plant Science 2001, 6, 495-496), protein instability, inconsistencies in product quality (Schillberg et al., Vaccine 2005, 23, 1764-1769), and insufficient capacity to produce viral-like products of expected size and immunogenicity (Arntzen et al., Vaccine 2005, 23, 1753-1756). In order to address these problems, codon optimization, careful approaches to harvesting and purifying plant or algae products, use of plant parts such as chloroplasts to increase uptake of the material, and improved subcellular targeting are all being considered as potential strategies (Koprowski, Vaccine 2005, 23, 1757-1763).

Considering the potential effect of animal pathogens, such as NDV on public health and the economy, methods of preventing infection and protecting animals are needed. Moreover, there is a need for an effective vaccine against the pathogens and a suitable method for making the vaccine.

SUMMARY OF THE INVENTION

Compositions comprising NDV (Newcastle Disease Virus) antigens and fragments and variants thereof are provided. The NDV antigens and fragments and variants thereof possess immunogenic and protective properties. Preferably, the NDV antigens comprise an NDV HN (hemagglutinin-neuraminidase) antigen or fragment or variant thereof. The NDV antigens may be produced in plants or algae.

The NDV antigens and fragments and variants thereof can be formulated into vaccines and/or pharmaceutical compositions. Such vaccines or compositions can be used to vaccinate an animal and provide protection against at least one form of NDV.

Methods of the invention include methods for making the NDV antigens and fragments and variants thereof in plants or algae. The methods also include methods of use including administering to an animal an effective amount of NDV antigenic polypeptide(s) and fragments and variants thereof to elicit a protective immunogenic response. After production in plants or algae, the NDV antigenic polypeptides and fragments and variants thereof can be partially or substantially purified for use as a vaccine or composition.

Kits comprising at least one NDV antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 provides a table showing the SEQ ID NO assigned to the polynucleotide and protein sequence.

FIG. 2 provides DNA and protein sequences of NDV HN genes and the glycosylation sites.

FIG. 3 shows the HA analysis in 96 well plate format.

FIG. 4 shows the SDS-PAGE and Western blot analysis of the expressed NDV HN gene.

FIGS. 6.1 and 6.2 provide the protein sequence alignments of NDV HN from different strains and mature protein sequence (without signal peptide).

FIG. 7.1 provides the sequence alignment of DNA from different NDV strains. FIG. 7.2 shows the DNA sequence alignment between wildtype and codon-optimized (microalgae-preferred) DNA coding for NDV HN and wildtype and codon-optimized (duckweed-preferred) DNA coding for NDV HN. FIG. 7.3 depicts the plasmid maps for duckweed plant transformation.

FIG. 8 provides the sequence alignment of NDV HN proteins to show the HN linear epitope region.

FIG. 9 provides a table showing the location and presence of glycosylation sites in NDV HN of different strains.

FIG. 10 provides a graphical feature map of the glycosylation sites and the HN linear epitope region of NDV HN CA/02 Protein (SEQ ID NO:3).

FIG. 11 provides peptide sequence analysis of expressed NDV HN (SEQ ID NO:3) in algae.

FIG. 12 provides the HI titer test result and motality test result.

DETAILED DESCRIPTION

Figure 5:
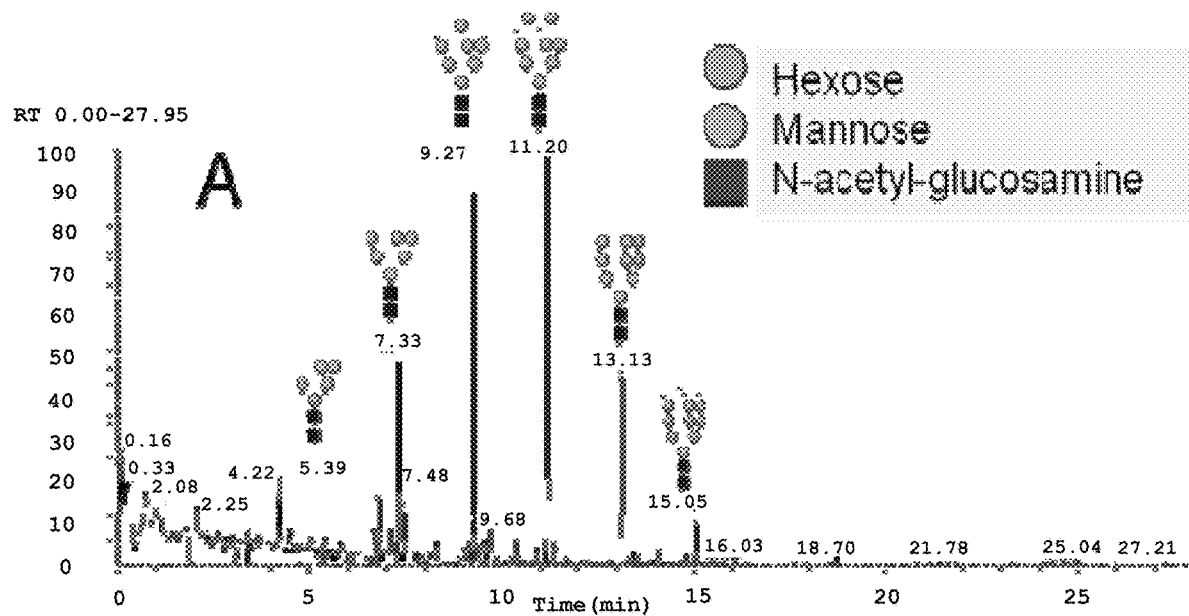
FIG. 5 shows the pictures of coomassie stain, periodic acid staining, immunoblot for glycosylation analysis and glycosylation site analysis.

Compositions comprising an NDV (Newcastle Disease Virus) antigen and fragments and variants thereof that elicit an immunogenic response in an animal are provided. The NDV antigen or fragments or variants thereof may be produced in algae. The NDV antigen or fragments or variants may be formulated into vaccines or pharmaceutical compositions and used to elicit or stimulate a protective response in an animal. In one embodiment the NDV antigen is an NDV hemaglutinin-neuraminidase (HN) polypeptide or active fragment or variant thereof.

It is recognized that the antigenic polypeptides of the invention may be full length polypeptides or active fragments or variants thereof. By "active fragments" or "active variants" is intended that the fragments or variants retain the antigenic nature of the polypeptide. Thus, the present invention encompasses any NDV polypeptide, antigen, epitope or immunogen that elicits an immunogenic response in an animal. The NDV polypeptide, antigen, epitope or immunogen may be any NDV polypeptide, antigen, epitope or immunogen that elicits, induces or stimulates a response in an animal.

A particular antigenic polypeptide of interest is hemagglutinin-neuraminidase (HN). The glycoprotein, hemagglutinin-neuraminidase (HN) has the transmembrane region located in the amino-terminal region making it a type II integral membrane protein that is involved with viral attachment to cells via sialic acid receptors. The HN protein protrudes from the envelope allowing the virus to contain both hemagglutinin and neuraminidase activities (Yusoff K, Tan W S, 2001, Avian Pathol 30:439-455).

However, there are different antigens, any of which can be used in the practice of the invention. It is further recognized that precursors of any of these antigens can be used.

The antigenic polypeptides of the invention are capable of protecting against NDV. That is, they are capable of stimulating an immune response in an animal. By "antigen" or "immunogen" means a substance that induces a specific immune response in a host animal. The antigen may comprise a whole organism, killed, attenuated or live; a portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The term "plants" as used herein includes both dicotyledonous (dicot) plants and monocotyledonous (monocot) plant. Dicot plants include, but are not limited to, legumes such as pea, alfalfa and soybean, carrot, celery, tomato, potato, tobacco, pepper, oilseed rape, beet, cabbage, cauliflower, broccoli, lettuce, peanut, and the like. Monocot plants include, but are not limited to, cereals such as wheat, barley, sorghum and millet, rye, triticale, maize, rice or oats, sugarcane, duckweed, grasses, and the like. The term "plant" also include non-flowering plants including, but not limited to, ferns, horsetails, club mosses, mosses, liverworts, hornworts, algae. The terms "algae" and "alga" as used herein include any strain of algae capable of producing a polypeptide or fragment or variant thereof. The algae may include, for example, red, brown, and green algae, gametophytes, and the like. The algae may be microalgae. The microalgae may be Thraustochytriaceae, for example, *Schizochytrium*, *Thraustochytrium*, *Labyrinthuloides*, and *Japonochytrium*.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Compositions

The present invention relates to an NDV vaccine or composition which may comprise an effective amount of a recombinant NDV polypeptide or antigen and a pharmaceutically or veterinarily acceptable carrier, excipient, or vehicle. The NDV polypeptide, antigen, epitope or immunogen may be any NDV polypeptide, antigen, epitope or immunogen that elicits, induces or stimulates a response in an animal. In one embodiment, the NDV polypeptide, antigen, epitope or immunogen is a hemagglutinin-neuramidase (HN), RNA polymerase, Fusion protein (F), matrix protein, phosphoprotein and a nucleoprotein. In another embodiment, the NDV antigen may be a hemagglutinin-neuramidase (HN).

The invention is based, in part, on Applicants' surprising discovery that a recombinant NDV HN gene expressed in a plant or algal protein expression system was highly immunogenic and protected animals against challenge from homologous and heterologous NDV strains.

The present invention relates to an NDV vaccine or composition which may comprise an effective amount of a recombinant NDV HN polypeptide or antigen and a pharmaceutically or veterinarily acceptable carrier, excipient, or vehicle. In one embodiment, the recombinant NDV HN antigen is expressed in algae. In yet another embodiment, the algae are selected from *Schizochytrium*. In one embodiment, the recombinant NDV HN antigen may be expressed in a *Schizochytrium* protein expression system, as described, for example, in U.S. Pat. No. 7,001,772, US 2008/0022422, US 2006/0275904, US 2006/0286650.

In an embodiment, the subject matter disclosed herein is directed to a composition comprising a recombinant NDV HN polypeptide or antigen produced by a duckweed expression system and plant material from duckweed, including the genus *Lemna*, and a pharmaceutical or veterinarily acceptable carrier, excipient or vehicle. In another embodiment, the subject matter disclosed herein is directed to an optionally aglycosylated protein produced by a duckweed expression system comprising an NDV HN polypeptide or antigen. The recombinant NDV HN polypeptide or antigen may be expressed in a *Lemna minor* protein expression system, such as Biolex's LEX SYSTEM℠.

In one embodiment, the pharmaceutically or veterinarily acceptable carrier, excipient, or vehicle may be a water-in-oil emulsion. In another embodiment, the water-in-oil emulsion may be a water/oil/water (W/O/W) triple emulsion. In yet another embodiment, the pharmaceutically or veterinarily acceptable carrier, excipient, or vehicle may be an oil-in-water emulsion.

In an embodiment, the composition or vaccine comprises a recombinant vector and a pharmaceutical or veterinary acceptable excipient, carrier or vehicle. The recombinant vector is plant or algae expression vector which may comprise a polynucleotide encoding an NDV polypeptide, antigen, epitope or immunogen. In one embodiment, the NDV polypeptide, antigen, epitope or immunogen may be derived from an avian infected with NDV or an avian NDV strain.

In an embodiment, the NDV polypeptide or antigen or fragment or variant thereof comprises an NDV HN polypeptide or fragment or variant thereof. In an aspect of this embodiment, the HN polypeptide or fragment or variant thereof is a recombinant polypeptide produced by an NDV HN gene. In another aspect of this embodiment, the NDV HN gene has at least 70% identity to the sequence as set forth in SEQ ID NO: 1, 2, 4, 6, 8, 12, 14, 16, 18, 22 or 23. In another aspect of this embodiment, the NDV HN polypeptide or fragment or variant thereof has at least 80% identity to the sequence as set forth in SEQ ID NO: 3, 5, 7, 9, 10, 11, 13, 15, 17, 19, 20, 21, or 28. In another aspect of this embodiment, the HN polypeptide or fragment or variant thereof comprises an HN linear epitope region. In another aspect of this embodiment, the epitope region has at least 80% identity to the sequence as set forth in SEQ ID NO: 10, 11, or 28.

In an embodiment, the NDV antigen is partially purified; or, in another embodiment, the NDV antigen is substantially purified. In yet another embodiment, the NDV antigen is present in the microalgae harvested in whole. In yet another embodiment, the NDV antigen is present in the low-speed supernatant.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an NDV polypeptide. A polynucleotide encoding a fragment of an NDV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

Glycosylation of a protein may have multiple effects on the immunogenicity of a protein. In the case of NDV, it appears glycosylation is required for the proper folding of the protein and conformational epitope formation (McGinnes, L. W., and T. G. Morrison. 1995, Virology 212:398-410.). According to McGinnes, et al., glycosylation of the HN protein at glycosylation sites 433 and 481 (see FIGS. 8-10) are required for protein binding activity and conformational epitope formation. Proper glycosylation of the HN protein may be required for the protein function and the immune response of the host to the composition of the invention.

Conformational epitopes and a primary linear epitope of the HN protein are described in Gotoh, B T, et al., 1988, Virology 163:174-82, Iorio, R. M., J. B. et al., 1986, J Gen Virol 67:1393-403, Iorio, R M, et al., 1989, Virus Res 13:245-61. It appears that variations in the linear epitope may be the cause of vaccine evasion by emerging strains (Cho, S H, et al., 2008, J Clin Microbiol 46:1541-4). FIG. 8 provides an alignment of the HN proteins from four NDV strains to show the level of variation in the linear epitope region.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding an NDV antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

In one aspect, the present invention provides NDV HN polypeptides. In another aspect, the present invention provides an NDV HN polypeptide having a sequence as set forth in SEQ ID NO: 3, 5, 7, 9, 10, 11, 13, 15, 17, 19, 20, 21, or 28 and variant or fragment thereof.

Moreover, homologs of NDV HN polypeptides are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by specification. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type NDV polypeptide can differ from the wild-type NDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type NDV polypeptide or polynucleotide sequences, and will exhibit a similar function.

In another aspect, the present invention provides a polypeptide having at least 70%, at least 75%, at least 80%, at least 85%, at least 90%, at least 95%, 96%, 97%, 98% or 99% sequence identity to an NDV HN polypeptide having a sequence as set forth in SEQ ID NO: 3, 5, 7, 9, 10, 11, 13, 15, 17, 19, 20, 21, or 28. In yet another aspect, the present invention provides an NDV HN polypeptide comprising an immunogenic fragment having a sequence as set forth in SEQ ID NO:10, SEQ ID NO:11, or SEQ ID NO:28, and wherein the polypeptide has at least 70%, at least 75%, at least 80%, at least 85%, at least 90%, at least 95%, 96%, 97%, 98% or 99% sequence identity to a polypeptide having a sequence as set forth in SEQ ID NO: 3, 5, 7, 9, 15, 17, 19, or 20.

In yet another aspect, the present invention provides fragments and variants of the NDV HN polypeptides identified above (SEQ ID NO: 3, 5, 7, 9, 10, 11, 13, 15, 17, 19, 20, 21, or 28) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 3, 5, 7, 9, 10, 11, 13, 15, 17, 19, 20, 21, or 28.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the NDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

An immunogenic fragment of an NDV HN polypeptide includes at least 8, 10, 13, 14, 15, or 20 consecutive amino acids, at least 21 amino acids, at least 23 amino acids, at least 25 amino acids, or at least 30 amino acids of an NDV HN polypeptide having a sequence as set forth in SEQ ID NO: 3, 5, 7, 9, 10, 11, 13, 15, 17, 19, 20, 21, or 28, or variants thereof. In another embodiment, a fragment of an NDV HN polypeptide includes a specific antigenic epitope found on a full-length NDV HN polypeptide. An immunogenic fragment may comprise a fragment containing the NDV HN linear epitope region. In one embodiment, the immunogenic fragment comprises the polypeptide having a sequence as set forth in SEQ ID NO:10, SEQ ID NO:11, or SEQ ID NO:28.

In another aspect, the present invention provides a polynucleotide encoding an NDV HN polypeptide, such as a polynucleotide encoding an NDV HN polypeptide having a sequence as set forth in SEQ ID NO: 3, 5, 7, 9, 10, 11, 13, 15, 17, 19, 20, 21, or 28. In yet another aspect, the present invention provides a polynucleotide encoding an NDV HN polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3, 5, 7, 9, 10, 11, 13, 15, 17, 19, 20, 21, or 28, or a conservative variant, an allelic variant, a homolog or an immunogenic fragment comprising at least eight or at east ten consecutive amino acids of one of these polypeptides, or a combination of these polypeptides. In yet another aspect, the present invention provides a polynucleotide encoding an NDV HN polypeptide comprising an immunogenic fragment having a sequence as set forth in SEQ ID NO:10, SEQ ID NO:11, or SEQ ID NO:28, and wherein the polypeptide has at least 70%, at least 75%, at least 80%, at least 85%, at least 90%, at least 95%, 96%, 97%, 98% or 99% sequence identity to a polypeptide having a sequence as set forth in SEQ ID NO: 3, 5, 7, 9, 15, 17, 19, or 20.

In another aspect, the present invention provides a polynucleotide having a nucleotide sequence as set forth in SEQ ID NO: 1, 2, 4, 6, 8, 12, 14, 16, 18, 22, or 23, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 2, 4, 6, 8, 12, 14, 16, 18, 22, or 23, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV polypeptides, the DNA sequence of the NDV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV HN polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server).

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymine (T) in the DNA sequence is considered equal to uracil (U) in the RNA sequence. Thus, RNA sequences are within the scope of the invention and can be derived from DNA sequences, by thymine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

Hybridization reactions can be performed under conditions of different stringency. Conditions that increase stringency of a hybridization reaction are well known. See for example, "Molecular Cloning: A Laboratory Manual", second edition (Sambrook et al., 1989).

The invention further encompasses the NDV polynucleotides contained in a vector molecule or an expression vector and operably linked to a promoter element.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an NDV polypeptide, antigen, epitope or immunogen are advantageously present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. an NDV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to compositions comprising vectors, such as expression vectors. The compositions can comprise one or more vectors, e.g., expression vectors, such as in vivo expression vectors, comprising and expressing one or more NDV polypeptides, antigens, epitopes or immunogens. In one embodiment, the vector comprises a polynucleotide coding for and/or expressing an NDV polypeptide, antigen, epitope or immunogen, in a pharmaceutically or veterinarily acceptable carrier, excipient or vehicle.

According to another embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) of GenBank accession number HUMTPA14. In another specific, non-limiting example, the plasmid utilized as a vector for the insertion of a polynucleotide sequence can contain the signal peptide sequence of equine IGF1 from amino acid M(24) to amino acid A(48) of GenBank accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises a polynucleotide encoding an NDV polypeptide, antigen, epitope or immunogen operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

The plasmids may comprise other expression control elements. It is particularly advantageous to incorporate stabilizing sequence(s), e.g., intron sequence(s), for example, maize alcohol dehydrogenase intron (maize ADHI intron), the first intron of the hCMV-IE (WO1989/01036), the intron II of the rabbit β-globin gene (van Ooyen et al., 1979). In another embodiment, the plasmids may comprise 3' UTR. The 3' UTR may be, but not limited to, *Agrobacterium* nopaline synthase (Nos) 3' UTR. The plasmids may further comprise the OrfC terminator (also known as the PFA3 terminator).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant NDV HN antigen is expressed in a transgenic plant. In another embodiment, the recombinant NDV HN antigen is expressed in transgenic algae. In yet another embodiment, the transgenic algae are *Schizochytrium*. Details of the algae protein expression system may be found, for example, in U.S. Pat. No. 7,001,772, US 2008/0022422. The NDV HN polypeptide or antigen in the embodiments may be any polypeptide disclosed herein, or a polypeptide encoded by any polynucleotide disclosed herein.

Methods for Expressing NDV polypeptides in Microalgae or Duckweed

In some embodiments of the invention, NDV HN polypeptides, or fragments or variants thereof, are expressed in microalgae or duckweed. These methods comprise the use of expression cassettes that are introduced into algae or plants using any suitable transformation method known in the art. Polynucleotides within these expression cassettes can be modified for enhanced expression of the antigenic NDV HN polypeptide, or fragment or variant thereof, in microalgae or duckweed, as follows.

Cassettes for Microalgae or duckweed Expression of Antigenic NDV Polypeptides

Transgenic microalgae or duckweed expressing an NDV HN polypeptide, or fragment or variant thereof are obtained by transformation of microalgae or duckweed with an expression cassette comprising a polynucleotide encoding the NDV HN polypeptide, or fragment or variant thereof. In this manner, a polynucleotide encoding the NDV HN polypeptide, or fragment or variant thereof, is constructed within an expression cassette and introduced into microalgae or duckweed by any suitable transformation method known in the art.

In some embodiments, the microalgae or duckweed that are transformed with an expression cassette comprising a polynucleotide encoding the NDV HN polypeptide, or fragment or variant thereof, have also been transformed with an expression cassette that provides for expression of another heterologous polypeptide of interest, for example, another NDV polypeptide, fragment, or variant thereof. The expression cassette providing for expression of another heterologous polypeptide of interest can be provided on the same polynucleotide (for example, on the same transformation vector) for introduction into microalgae or duckweed, or on a different polynucleotide (for example, on different transformation vectors) for introduction into the microalgae or duckweed at the same time or at different times, by the same or by different methods of introduction, for example, by the same or different transformation methods.

The expression cassettes for use in transformation of microalgae or duckweed comprise expression control elements that at least comprise a transcriptional initiation region (e.g., a promoter) operably linked to the polynucleotide of interest, i.e., a polynucleotide encoding an NDV HN polypeptide, fragment, or variant thereof "Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame. Such an expression cassette is provided with a plurality of restriction sites for insertion of the polynucleotide or polynucleotides of interest (e.g., one polynucleotide of interest, two polynucleotides of interest, etc.) to be under the transcriptional regulation of the promoter and other expression control elements. In particular embodiments of the invention, the polynucleotide to be transferred contains two or more expression cassettes, each of which contains at least one polynucleotide of interest.

By "expression control element" is intended a regulatory region of DNA, usually comprising a TATA box, capable of directing RNA polymerase II, or in some embodiments, RNA polymerase III, to initiate RNA synthesis at the appropriate transcription initiation site for a particular coding sequence. An expression control element may additionally comprise other recognition sequences generally positioned upstream or 5' to the TATA box, which influence (e.g., enhance) the transcription initiation rate. Furthermore, an expression control element may additionally comprise sequences generally positioned downstream or 3' to the TATA box, which influence (e.g., enhance) the transcription initiation rate.

The transcriptional initiation region (e.g., a promoter) may be native or homologous or foreign or heterologous to the microalgal host or duckweed plant, or could be the natural sequence or a synthetic sequence. By foreign, it is intended that the transcriptional initiation region is not found in the wild-type microalgal host or duckweed plant into which the transcriptional initiation region is introduced. By "functional promoter" is intended the promoter, when operably linked to a sequence encoding an NDV HN polypeptide, or fragment or variant thereof, is capable of driving expression (i.e., transcription and translation) of the encoded polypeptide, fragment, or variant. The promoters can be selected based on the desired outcome. Thus the expression cassettes of the invention can comprise constitutive, inducible, tissue-preferred, or other promoters for expression in microalgae or duckweed.

Any suitable promoter known in the art can be employed in the expression cassettes according to the present invention, including bacterial, yeast, fungal, insect, mammalian, algae, and plant promoters. For example, plant or algae promoters, including microalgae promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. U.S. Pat. No. 7,001,772 disclosed nucleic acid and amino acid sequences for an acetolactate synthase, an acetolactate synthase promoter and terminator region, an α-tubulin promoter, a promoter from a *Thraustochytriales* polyketide synthase (PKS) system, and a fatty acid desaturase promoter, each from a *Thraustochytriales* microorganism. U.S. patent application publications US2006/0275904 and US2006/0286650 disclose the sequences for promoters and terminators for each of *Schizochytrium* actin, elongation factor 1 alpha and glyceraldehyde 3-phosphate dehydrogenase as well as their use in vectors for expressing genes in *Schizochytrium* host cells. The microalgae RubP carboxylase small subunit promoter is known in the art (Silverthorne et al. (1990) *Plant Mol. Biol.* 15:49). Other promoters from viruses that infect plants or algae are also suitable including, but not limited to, promoters isolated from *Dasheen mosaic* virus, *Chlorella* virus (e.g., the *Chlorella* virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Expression control elements, including promoters, can be chosen to give a desired level of regulation. For example, in some instances, it may be advantageous to use a promoter that confers constitutive expression (e.g., the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646). In the present invention, the expression cassette can contain activating nucleotide sequences inserted upstream of the promoter sequence to enhance the expression of the antigenic NDV polypeptide of interest, or fragment or variant thereof. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646).

The expression cassette thus includes in the 5'-3' direction of transcription, an expression control element comprising a transcriptional and translational initiation region, a polynucleotide of encoding an NDV HN polypeptide (or fragment or variant thereof), and a transcriptional and translational termination region functional in plants or algae. Any suitable termination sequence known in the art may be used in accordance with the present invention. The termination region may be native with the transcriptional initiation region, may be native with the coding sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence.

Generally, the expression cassette will comprise a selectable marker gene for the selection of transformed microalgae cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al.

(1987) EMBO J. 6:2513; DeBlock et al. (1989) Plant Physiol. 91:691; Fromm et al. (1990) Bio Technology 8:833; Gordon-Kamm et al. (1990) Plant Cell 2:603. For example, resistance to glyphosate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) has been obtained by using bacterial genes encoding phosphinothricin acetyltransferase, a nitrilase, or a 2,4-dichlorophenoxyacetate monooxygenase, which detoxify the respective herbicides.

For purpose of the present invention, selectable marker genes include, but are not limited to, genes encoding neomycin phosphotransferase II (Fraley et al. (1986) CRC Critical Reviews in Plant Science 4:1); cyanamide hydratase (Maier-Greiner et al. (1991) Proc. Natl. Acad. Sci. USA 88:4250); acetolactate synthase (ALS, Li, et al. (1992) Plant Physiol. 100:662-668); aspartate kinase; dihydrodipicolinate synthase (Perl et al. (1993) BioTechnology 11:715); bar gene (Toki et al. (1992) Plant Physiol. 100:1503; Meagher et al. (1996) Crop Sci. 36:1367); tryptophan decarboxylase (Goddijn et al. (1993) Plant Mol. Biol. 22:907); neomycin phosphotransferase (NEO; Southern et al. (1982) J. Mol. Appl. Gen. 1:327); hygromycin phosphotransferase (HPT or HYG; Shimizu et al. (1986) Mol. Cell. Biol. 6:1074); dihydrofolate reductase (DHFR; Kwok et al. (1986) Proc. Natl. Acad. Sci. USA 83:4552); phosphinothricin acetyltransferase (DeBlock et al. (1987) EMBO J. 6:2513); 2,2-dichloropropionic acid dehalogenase (Buchanan-Wollatron et al. (1989) J. Cell. Biochem. 13D:330); acetohydroxyacid synthase (U.S. Pat. No. 4,761,373; Haughn et al. (1988) Mol. Gen. Genet. 221:266); 5-enolpyruvyl-shikimate-phosphate synthase (aroA; Comai et al. (1985) Nature 317:741); haloarylnitrilase (WO 87/04181); acetyl-coenzyme A carboxylase (Parker et al. (1990) Plant Physiol. 92:1220); dihydropteroate synthase (sulI; Guerineau et al. (1990) Plant Mol. Biol. 15:127); and 32 kDa photosystem II polypeptide (psbA; Hirschberg et al. (1983) Science 222:1346 (1983).

Also included are genes encoding resistance to: gentamycin (e.g., aacC1, Wohlleben et al. (1989) Mol. Gen. Genet. 217:202-208); chloramphenicol (Herrera-Estrella et al. (1983) EMBO J. 2:987); methotrexate (Herrera-Estrella et al. (1983) Nature 303:209; Meijer et al. (1991) Plant Mol. Biol. 16:807); hygromycin (Waldron et al. (1985) Plant Mol. Biol. 5:103; Zhijian et al. (1995) Plant Science 108:219; Meijer et al. (1991) Plant Mol. Bio. 16:807); streptomycin (Jones et al. (1987) Mol. Gen. Genet. 210:86); spectinomycin (Bretagne-Sagnard et al. (1996) Transgenic Res. 5:131); bleomycin (Hille et al. (1986) Plant Mol. Biol. 7:171); sulfonamide (Guerineau et al. (1990) Plant Mol. Bio. 15:127); bromoxynil (Stalker et al. (1988) Science 242:419); 2,4-D (Streber et al. (1989) BioTechnology 7:811); phosphinothricin (DeBlock et al. (1987) EMBO J. 6:2513); spectinomycin (Bretagne-Sagnard and Chupeau, Transgenic Research 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) Curr. Opin. Biotech. 3:506; Chistopherson et al. (1992) PNAS USA 89:6314; Yao et al. (1992) Cell 71:63; Reznikoff (1992) Mol. Microbiol. 6:2419; Barkley et al. (1980) The Operon 177-220; Hu et al. (1987) Cell 48:555; Brown et al. (1987) Cell 49:603; Figge et al. (1988) Cell 52:713; Deuschle et al. (1989) PNAS USA 86:5400; Fuerst et al. (1989) PNAS USA 86:2549; Deuschle et al. (1990) Science 248:480; Labow et al. (1990) Mol. Cell. Biol. 10:3343; Zambretti et al. (1992) PNAS USA 89:3952; Baim et al. (1991) PNAS USA 88:5072; Wyborski et al. (1991) Nuc. Acids Res. 19:4647; Hillenand-Wissman (1989) Topics in Mol. And Struc. Biol. 10:143; Degenkolb et al. (1991) Antimicrob. Agents Chemother. 35:1591; Kleinschnidt et al. (1988) Biochemistry 27:1094; Gatz et al. (1992) Plant J. 2:397; Gossen et al. (1992) PNAS USA 89:5547; Oliva et al. (1992) Antimicrob. Agents Chemother. 36:913; Hlavka et al. (1985) Handbook of Experimental Pharmacology 78; and Gill et al. (1988) Nature 334:721.

The above list of selectable marker genes is not meant to be limiting. Any selectable marker gene can be used in the present invention.

Modification of Nucleotide Sequences for Enhanced Expression in a Microalgal Host or Duckweed Plant Where the NDV HN polypeptide or fragment or variant thereof is expressed within microalgae or duckweed, the expressed polynucleotide sequence encoding the NDV HN polypeptide or fragment or variant thereof can be modified to enhance its expression in microalgae. One such modification is the synthesis of the polynucleotide using plant- or algae-preferred codons, particularly microalgae-preferred codons. Methods are available in the art for synthesizing nucleotide sequences with plant- or algae-preferred codons. See, e.g., U.S. Pat. Nos. 5,380,831 and 5,436,391; EP 0 359 472; EP 0 385 962; WO 91/16432; Perlak et al. (1991) PNAS USA 15:3324; Iannacome et al. (1997) Plant Mol. Biol. 34:485; and Murray et al. (1989) Nucleic Acids. Res. 17:477. Synthesis can be accomplished using any method known to one of skill in the art. The preferred codons may be determined from the codons of highest frequency in the proteins expressed in microalgae. For example, the frequency of codon usage for microalgae is found in Table A.

TABLE A

Schizochytrium sp. ATCC_20888 [gbpln]: 3 CDS's (6473 codons)
fields: [triplet] [frequency: per thousand] ([number])

| | | | | | | | |
|---|---|---|---|---|---|---|---|
| UUU | 12.2 (79) | UCU | 7.0 (45) | UAU | 1.1 (7) | UGU | 0.8 (5) |
| UUC | 19.9 (129) | UCC | 23.8 (154) | UAC | 21.5 (139) | UGC | 15.3 (99) |
| UUA | 0.0 (0) | UCA | 0.5 (3) | UAA | 0.5 (3) | UGA | 0.0 (0) |
| UUG | 0.6 (4) | UCG | 18.8 (122) | UAG | 0.0 (0) | UGG | 8.3 (54) |
| CUU | 12.7 (82) | CCU | 11.7 (76) | CAU | 2.3 (15) | CGU | 7.1 (46) |
| CUC | 61.2 (396) | CCC | 23.8 (154) | CAC | 12.8 (83) | CGC | 42.9 (278) |
| CUA | 0.0 (0) | CCA | 1.5 (10) | CAA | 2.3 (15) | CGA | 0.3 (2) |
| CUG | 7.4 (48) | CCG | 16.2 (105) | CAG | 27.7 (179) | CGG | 0.8 (5) |
| AUU | 13.9 (90) | ACU | 9.1 (59) | AAU | 1.9 (12) | AGU | 1.5 (10) |

TABLE A-continued

*Schizochytrium* sp. ATCC_20888 [gbpln]: 3 CDS's (6473 codons)
fields: [triplet] [frequency: per thousand] ([number])

| | | | | | | | |
|---|---|---|---|---|---|---|---|
| AUC | 33.5 (217) | ACC | 29.2 (189) | AAC | 32.4 (210) | AGC | 15.6 (101) |
| AUA | 0.0 (0) | ACA | 1.5 (10) | AAA | 2.2 (14) | AGA | 0.2 (1) |
| AUG | 27.8 (180) | ACG | 9.6 (62) | AAG | 54.5 (353) | AGG | 0.0 (0) |
| GUU | 8.3 (54) | GCU | 24.4 (158) | GAU | 13.4 (87) | GGU | 13.0 (84) |
| GUC | 53.0 (343) | GCC | 86.0 (557) | GAC | 45.0 (291) | GGC | 54.5 (353) |
| GUA | 0.2 (1) | GCA | 4.0 (26) | GAA | 7.3 (47) | GGA | 3.9 (25) |
| GUG | 14.4 (93) | GCG | 15.9 (103) | GAG | 62.3 (403) | GGG | 0.5 (3) |

For purposes of the present invention, "microalgae-preferred codons" refers to codons that have a frequency of codon usage in microalgae of greater than 17%. The term "microalgae-preferred codons" as used herein refers to codons that have a frequency of codon usage in the family Thraustochytriaceae of greater than 17%. "*Schizochytrium*-preferred codons" as used herein refers to codons that have a frequency of codon usage in *Schizochytrium* of greater than 17% where the frequency of codon usage in *Schizochytrium* is obtained from the Codon Usage Database (GenBank Release 160.0, Jun. 15, 2007).

The frequency of codon usage for *Lemna minor* is found in Table B, the frequency of codon usage for *Schizochytrium* is found in Table C.

For purposes of the present invention, "duckweed-preferred codons" refers to codons that have a frequency of codon usage in duckweed of greater than 17%. "*Lemna*-preferred codons" as used herein refers to codons that have a frequency of codon usage in the genus *Lemna* of greater than 17%. "*Lemna* minor-preferred codons" as used herein refers to codons that have a frequency of codon usage in *Lemna minor* of greater than 17% where the frequency of codon usage in *Lemna minor* is obtained from the Codon Usage Database (GenBank Release 160.0, Jun. 15, 2007).

It is further recognized that all or any part of the polynucleotide encoding the antigenic NDV polypeptide of interest, or fragment or variant thereof, may be optimized or synthetic. In other words, fully optimized or partially optimized sequences may also be used. For example, 40%, 45%,

TABLE B

*Lemna minor* [gbpln]: 4 CDS's (1597 codons)
fields: [triplet] [frequency: per thousand] ([number])

| | | | | | | | |
|---|---|---|---|---|---|---|---|
| UUU | 17.5 (28) | UCU | 13.8 (22) | UAU | 8.8 (14) | UGU | 5.0 (8) |
| UUC | 36.3 (58) | UCC | 17.5 (28) | UAC | 15.7 (25) | UGC | 14.4 (23) |
| UUA | 5.6 (9) | UCA | 14.4 (23) | UAA | 0.0 (0) | UGA | 1.9 (3) |
| UUG | 13.8 (22) | UCG | 13.8 (22) | UAG | 0.6 (1) | UGG | 16.3 (26) |
| CUU | 15.7 (25) | CCU | 11.9 (19) | CAU | 6.9 (11) | CGU | 4.4 (7) |
| CUC | 25.7 (41) | CCC | 15.7 (25) | CAC | 16.9 (27) | CGC | 18.2 (29) |
| CUA | 5.0 (8) | CCA | 11.3 (18) | CAA | 10.0 (16) | CGA | 6.3 (10) |
| CUG | 21.3 (34) | CCG | 14.4 (23) | CAG | 22.5 (36) | CGG | 10.6 (17) |
| AUU | 18.8 (30) | ACU | 9.4 (15) | AAU | 13.8 (22) | AGU | 10.0 (16) |
| AUC | 19.4 (31) | ACC | 17.5 (28) | AAC | 21.9 (35) | AGC | 15.0 (24) |
| AUA | 1.9 (3) | ACA | 5.0 (8) | AAA | 15.7 (25) | AGA | 20.7 (33) |
| AUG | 20.7 (33) | ACG | 10.0 (16) | AAG | 35.7 (57) | AGG | 17.5 (28) |
| GUU | 15.0 (24) | GCU | 25.0 (40) | GAU | 20.0 (32) | GGU | 8.1 (13) |
| GUC | 25.0 (40) | GCC | 22.5 (36) | GAC | 26.3 (42) | GGC | 21.9 (35) |
| GUA | 6.3 (10) | GCA | 14.4 (23) | GAA | 26.3 (42) | GGA | 16.9 (27) |
| GUG | 30.7 (49) | GCG | 18.2 (29) | GAG | 40.1 (64) | GGG | 18.2 (29) |

TABLE C

*Schizochytrium* sp. ATCC_20888 [gbpln]: 3 CDS's (6473 codons)
fields: [triplet] [frequency: per thousand] ([number])

| | | | | | | | |
|---|---|---|---|---|---|---|---|
| UUU | 12.2 (79) | UCU | 7.0 (45) | UAU | 1.1 (7) | UGU | 0.8 (5) |
| UUC | 19.9 (129) | UCC | 23.8 (154) | UAC | 21.5 (139) | UGC | 15.3 (99) |
| UUA | 0.0 (0) | UCA | 0.5 (3) | UAA | 0.5 (3) | UGA | 0.0 (0) |
| UUG | 0.6 (4) | UCG | 18.8 (122) | UAG | 0.0 (0) | UGG | 8.3 (54) |
| CUU | 12.7 (82) | CCU | 11.7 (76) | CAU | 2.3 (15) | CGU | 7.1 (46) |
| CUC | 61.2 (396) | CCC | 23.8 (154) | CAC | 12.8 (83) | CGC | 42.9 (278) |
| CUA | 0.0 (0) | CCA | 1.5 (10) | CAA | 2.3 (15) | CGA | 0.3 (2) |
| CUG | 7.4 (48) | CCG | 16.2 (105) | CAG | 27.7 (179) | CGG | 0.8 (5) |
| AUU | 13.9 (90) | ACU | 9.1 (59) | AAU | 1.9 (12) | AGU | 1.5 (10) |
| AUC | 33.5 (217) | ACC | 29.2 (189) | AAC | 32.4 (210) | AGC | 15.6 (101) |
| AUA | 0.0 (0) | ACA | 1.5 (10) | AAA | 2.2 (14) | AGA | 0.2 (1) |
| AUG | 27.8 (180) | ACG | 9.6 (62) | AAG | 54.5 (353) | AGG | 0.0 (0) |
| GUU | 8.3 (54) | GCU | 24.4 (158) | GAU | 13.4 (87) | GGU | 13.0 (84) |
| GUC | 53.0 (343) | GCC | 86.0 (557) | GAC | 45.0 (291) | GGC | 54.5 (353) |
| GUA | 0.2 (1) | GCA | 4.0 (26) | GAA | 7.3 (47) | GGA | 3.9 (25) |
| GUG | 14.4 (93) | GCG | 15.9 (103) | GAG | 62.3 (403) | GGG | 0.5 (3) |

50%, 55%, 60%, 65%, 70%, 75%, 80%, 85%, 87%, 90%, 91%, 92%, 93%, 94%, 95%, 96%, 97%, 98%, 99%, or 100% of the codons may be microalgae-preferred or duckweed-preferred codons. In one embodiment, between 90% and 96% of the codons are microalgae-preferred or duckweed-preferred codons. In one embodiment, the NDV polypeptide is an NDV HN polypeptide, for example, the NDV HN polypeptide as set forth in SEQ ID NO:3 or 15, and the expression cassette comprises an optimized coding sequence for this NDV HN polypeptide, wherein the coding sequence comprises microalgae-preferred codons, for example, Thraustochytriaceae-preferred or *Schizochytrium*-preferred codons. In one such embodiment, the expression cassette comprises SEQ ID NO:1 or 14, which contains *Schizochytrium*-preferred codons encoding the HN polypeptide set forth in SEQ ID NO:3 or 15. In another such embodiment, the expression cassette comprises SEQ ID NO:22 or 23, which contains *Schizochytrium*-preferred codons encoding the HN polypeptide set forth in SEQ ID NO: 17, or 20.

Other modifications can also be made to the polynucleotide encoding the antigenic NDV polypeptide of interest, or fragment or variant thereof, to enhance its expression in microalgae. These modifications include, but are not limited to, elimination of sequences encoding spurious polyadenylation signals, exon-intron splice site signals, transposon-like repeats, and other such well characterized sequences that may be deleterious to gene expression. When possible, the polynucleotide encoding the heterologous polypeptide of interest may be modified to avoid predicted hairpin secondary mRNA structures.

There are known differences between the optimal translation initiation context nucleotide sequences for translation initiation codons in animals and plants. "Translation initiation context nucleotide sequence" as used herein refers to the identity of the three nucleotides directly 5' of the translation initiation codon. "Translation initiation codon" refers to the codon that initiates the translation of the mRNA transcribed from the nucleotide sequence of interest. The composition of these translation initiation context nucleotide sequences can influence the efficiency of translation initiation. See, for example, Lukaszewicz et al. (2000) *Plant Science* 154:89-98; and Joshi et al. (1997); *Plant Mol. Biol.* 35:993-1001. In the present invention, the translation initiation context nucleotide sequence for the translation initiation codon of the polynucleotide encoding the antigenic NDV polypeptide of interest, or fragment or variant thereof, may be modified to enhance expression in microalgae. In one embodiment, the nucleotide sequence is modified such that the three nucleotides directly upstream of the translation initiation codon are "ACC." In a second embodiment, these nucleotides are "ACA."

Expression of an antigenic NDV polypeptide in microalgae or duckweed can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *PNAS USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353: 90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA*, 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) *Virology* 81:382). See also, Della-Cioppa et al. (1987) *Plant Physiology* 84:965. Leader sequence comprising plant intron sequence, including intron sequence from the maize alcohol dehydrogenase 1 (ADH1) gene, the castor bean catalase gene, or the *Arabidopsis* tryptophan pathway gene PAT1 has also been shown to increase translational efficiency in plants (Callis et al. (1987) *Genes Dev.* 1:1183-1200; Mascarenhas et al. (1990) *Plant Mol. Biol.* 15:913-920).

In some embodiments of the present invention, nucleotide sequence corresponding to nucleotides 1222-1775 of the maize alcohol dehydrogenase 1 gene (ADH1; GenBank Accession Number X04049) is inserted upstream of the polynucleotide encoding the NDV HN polypeptide, or fragment or variant thereof, to enhance the efficiency of its translation. In another embodiment, the expression cassette contains the leader from the *Lemna gibba* ribulose-bisphosphate carboxylase small subunit 5B gene (RbcS leader; see Buzby et al. (1990) *Plant Cell* 2:805-814).

It is recognized that any of the expression-enhancing nucleotide sequence modifications described above can be used in the present invention, including any single modification or any possible combination of modifications. The phrase "modified for enhanced expression" in microalgae or duckweed, as used herein, refers to a polynucleotide sequence that contains any one or any combination of these modifications.

Signal Peptide.

The NDV polypeptide of interest can be normally or advantageously expressed as a secreted protein. Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide may be cleaved from the precursor polypeptide to produce a "mature" polypeptide lacking the signal peptide. The signal peptide may not be cleaved and the entire polypeptide including the signal peptide is secreted from the cell. In an embodiment of the present invention, an NDV HN polypeptide, or fragment or variant thereof, is expressed in microalgae or duckweed from a polynucleotide sequence that is operably linked with a nucleotide sequence encoding a signal peptide that directs secretion of the NDV HN polypeptide, or fragment or variant thereof, into the culture medium. Plant or algae signal peptides that target protein translocation to the endoplasmic reticulum (for secretion outside of the cell) are known in the art. See, for example, U.S. Pat. No. 6,020,169. In the present invention, any plant or algae signal peptide can be used to target the expressed polypeptide to the ER.

In some embodiments, the signal peptide is the *Arabidopsis thaliana* basic endochitinase signal peptide (amino acids 14-34 of NCBI Protein Accession No. BAA82823), the extensin signal peptide (Stiefel et al. (1990) *Plant Cell* 2:785-793), the rice α-amylase signal peptide (amino acids 1-31 of NCBI Protein Accession No. AAA33885; see also GenBank M24286). In another embodiment, the signal peptide corresponds to the signal peptide of a secreted microalgae protein.

In one embodiment, the signal peptide of the present invention is the NDV HN signal peptide as set forth in SEQ ID NO:13 (encoded by a polynucleotide having the sequence as set forth in SEQ ID NO:12), or SEQ ID NO:21

(encoded by a polynucleotide having the sequence as set forth in SEQ ID NO:27). The NDV HN signal peptide of viral origin showed surprising result in the expression of the NDV protein in microalgae, where it directed the translocation of the polypeptide chain across the membrane and into the endoplasmic reticulum for secretion from the cell.

Alternatively, a mammalian signal peptide can be used to target the recombinantly produced antigenic NDV polypeptide for secretion from microalgae. It has been demonstrated that plant cells recognize mammalian signal peptides that target the endoplasmic reticulum, and that these signal peptides can direct the secretion of polypeptides not only through the plasma membrane but also through the plant cell wall. See U.S. Pat. Nos. 5,202,422 and 5,639,947.

In one embodiment, the nucleotide sequence encoding the signal peptide is modified for enhanced expression in microalgae, utilizing any modification or combination of modifications disclosed above for the polynucleotide sequence of interest.

The secreted NDV HN polypeptide, or fragment or variant thereof, can be harvested from the culture medium by any conventional means known in the art, including, but not limited to, chromatography, electrophoresis, dialysis, solvent-solvent extraction, and the like. In so doing, partially or substantially purified antigenic NDV polypeptide, or fragment or variant thereof, can be obtained from the culture medium.

Transformed Microalgae or Duckweed

The present invention provides transformed microalgae or duckweed plant expressing an NDV HN polypeptide, or fragment or variant thereof. The term "microalgae" refers to members of the family Thraustochytriaceae. This family currently is divided into four genera: *Schizochytrium, Thraustochytrium, Labyrinthuloides*, and *Japonochytrium*. Exemplary *Schizochytrium* include, but not limited to, *Schizochytrium aggregatum, Schizochytrium limacinum, Schizochytrium* sp. (S31) (ATCC 20888), *Schizochytrium* sp. (S8) (ATCC 20889), *Schizochytrium* sp. (LC-RM) (ATCC 18915), *Schizochytrium* sp. (SR21) (ATCC 28209) and deposited *Schizochytrium limacinum* strain IFO 32693 (Honda et Yokochi).

The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda,* and *Wl. neotropica*) and genus *Landoltia* (*L. punctata*). *Lemna* species can be classified using the taxonomic scheme described by Landolt (1986) *Biosystematic Investigation on the Family of Duckweeds: The family of Lemnaceae—A Monograph Study* (Geobatanischen Institut ETH, Stiftung Rubel, Zurich).

As used herein, "plant" includes whole plants, plant organs (e.g., fronds (leaves), stems, roots, etc.), seeds, plant cells, and progeny of same. Parts of transgenic plants are to be understood within the scope of the invention to comprise, e.g., plant cells, plant protoplasts, plant cell tissue cultures from which plants can be regenerated, tissues, plant calli, embryos as well as flowers, ovules, stems, fruits, leaves, roots, root tips, nodules, and the like originating in transgenic plants or their progeny previously transformed with a polynucleotide of interest and therefore consisting at least in part of transgenic cells.

The transformed microalgae or duckweed plants of the invention can be obtained by introducing an expression construct comprising a polynucleotide encoding an NDV HN polypeptide, or fragment or variant thereof, into the microalgae or duckweed plant of interest.

The term "introducing" in the context of a polynucleotide, for example, an expression construct comprising a polynucleotide encoding an antigenic NDV polypeptide, or fragment or variant thereof, is intended to mean presenting to the microalgae or duckweed plants the polynucleotide in such a manner that the polynucleotide gains access to the interior of a cell of the microalgae or duckweed. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the microalgae or duckweed host cell of interest in a single transformation event, in separate transformation events, or, for example, as part of a breeding protocol. The compositions and methods of the invention do not depend on a particular method for introducing one or more polynucleotides into microalgae, only that the polynucleotide(s) gains access to the interior of at least one cell of the microalgae or duckweed plants. Methods for introducing polynucleotides into plants or algae are known in the art including, but not limited to, transient transformation methods, stable transformation methods, and virus-mediated methods.

"Transient transformation" in the context of a polynucleotide such as a polynucleotide encoding an NDV HN polypeptide, or fragment or variant thereof, is intended to mean that a polynucleotide is introduced into the microalgae or duckweed and does not integrate into the genome of the microalgae or duckweed.

By "stably introducing" or "stably introduced" in the context of a polynucleotide (such as a polynucleotide encoding an NDV HN polypeptide, or fragment or variant thereof) introduced into microalgae or duckweed is intended the introduced polynucleotide is stably incorporated into the microalgae or duckweed genome, and thus the microalgae or duckweed plant is stably transformed with the polynucleotide.

"Stable transformation" or "stably transformed" is intended to mean that a polynucleotide, for example, a polynucleotide encoding an NDV HN polypeptide, or fragment or variant thereof, introduced into microalgae or duckweed plant integrates into the genome of the microalgae or plant and is capable of being inherited by the progeny thereof, more particularly, by the progeny of multiple successive generations. In some embodiments, successive generations include progeny produced vegetatively (i.e., asexual reproduction), for example, with clonal propagation. In other embodiments, successive generations include progeny produced via sexual reproduction.

An expression construct comprising a polynucleotide encoding an NDV HN polypeptide, or fragment or variant thereof, can be introduced into microalgae or plant of interest using any transformation protocol known to those of skill in art. Suitable methods of introducing nucleotide sequences into microalgae or plant cells or nodules include microinjection (Crossway et al. (1986) *Biotechniques* 4:320-334), electroporation (Riggs et al. (1986) *PNAS USA* 83:5602-5606), *Agrobacterium*-mediated transformation (U.S. Pat. Nos. 5,563,055 and 5,981,840), direct gene transfer (Paszkowski et al. (1984) *EMBO J.* 3:2717-2722), ballistic particle acceleration (see, e.g., U.S. Pat. Nos. 4,945,050; 5,879,918; 5,886,244; and 5,932,782); and Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926). The cells that have been transformed may be grown into plants or algae in accordance with conventional ways.

As noted above, stably transformed microalgae or plants can be obtained by any gene transfer method known in the art, such as one of the gene transfer methods disclosed in U.S. Pat. No. 6,040,498 or U.S. Patent Application Publication Nos. 2003/0115640, 2003/0033630 or 2002/0088027. Microalgal or plants can be efficiently transformed with an expression cassette containing a nucleic acid sequence as described herein by any one of a number of methods including *Agrobacterium*-mediated gene transfer, ballistic bombardment or electroporation. The *Agrobacterium* used can be *Agrobacterium tumefaciens* or *Agrobacterium rhizogenes*. Stable microalgae or plant transformants can be isolated by transforming the microalgae or plant cells with both the nucleic acid sequence of interest and a gene that confers resistance to a selection agent, followed by culturing the transformed cells in a medium containing the selection agent. See, for example, U.S. Pat. No. 6,040,498.

The stably transformed microalgae or plants utilized in these methods should exhibit normal morphology and be fertile by sexual reproduction and/or able to reproduce vegetatively (i.e., asexual reproduction), for example, with clonal propagation. Preferably, transformed microalgae or plants of the present invention contain a single copy of the transferred nucleic acid comprising a polynucleotide encoding an NDV HN polypeptide, or fragment or variant thereof, and the transferred nucleic acid has no notable rearrangements therein. It is recognized that the transformed microalgae of the invention may contain the transferred nucleic acid present in low copy numbers (i.e., no more than twelve copies, no more than eight copies, no more than five copies, alternatively, no more than three copies, as a further alternative, fewer than three copies of the nucleic acid per transformed cell).

Transformed plants or algae expressing an NDV HN polypeptide, or fragment or variant thereof, can be cultured under suitable conditions for expressing the NDV HN polypeptide, or fragment or variant thereof. The NDV HN polypeptide, or fragment or variant thereof, can then be harvested from the microalgae, the culture medium, or the microalgae and the culture medium, and, where desired, purified using any conventional isolation and purification method known in the art, including chromatography, electrophoresis, dialysis, solvent-solvent extraction, and the like. The NDV HN polypeptide, or fragment or variant thereof, can then be formulated as a vaccine for therapeutic applications, as described elsewhere herein.

Methods of Preparing an NDV Polypeptide

As described fully herein, in an embodiment, a method of producing a recombinant NDV HN polypeptide comprises: (a) culturing microalgal or duckweed plants within a microalgal or duckweed culture medium, wherein the microalgal or duckweed plants are stably transformed to express the NDV polypeptide, and wherein the NDV polypeptide is expressed from a nucleotide sequence comprising a coding sequence for said recombinant NDV polypeptide and an operably linked coding sequence for a signal peptide that directs secretion of the NDV polypeptide into the culture medium; and (b) collecting the NDV polypeptide from said culture medium. The term collecting includes but is not limited to harvesting from the culture medium or purifying.

After production of the recombinant polypeptide in microalgae or plants, any method available in the art may be used for protein purification. The various steps include freeing the protein from the nonprotein or algae or plant material, followed by the purification of the protein of interest from other proteins. The recombinant protein may be a secreted protein that is isolated from the culture medium following its production by the cell and may comprise a signal peptide. Said signal peptide may be cleaved following secretion, to produce a mature protein product. Depending on the vector and host system used for production, resultant recombinant NDV polypeptides of the present invention may either remain within the recombinant cell or be secreted into the fermentation medium or be secreted into a space between two cellular membranes; or be retained on the outer surface of a cell membrane. Initial steps in the purification process include centrifugation, filtration or a combination thereof. After the initial centrifugation at low speed, the low speed supernatant may be used for pharmaceutical composition or vaccine preparation. The low speed supernatant may undergo further purification using various method described below. Proteins secreted within the extracellular space of tissues can be obtained using vacuum or centrifugal extraction. Minimal processing could also involve preparation of crude products. Other methods include maceration and extraction in order to permit the direct use of the extract.

Recombinant proteins produced by the method of the present invention may be purified using a variety of standard protein purification techniques, such as, but not limited to, centrifugation, filtration, affinity chromatography, ion exchange chromatography, eletrophoresis, hydrophobic interaction chromatography, gel filtration chromatography, reverse phase chromatography, concanavalin A chromatography, chromatofocusing and differential solubilization. Methods to purify the protein of interest may exploit differences in protein size, physio-chemical properties, and binding affinity. Such methods include chromatography, including procainamide affinity, size exclusion, high pressure liquid, reversed-phase, and anion-exchange chromatography, affinity tags, etc. In particular, immobilized Ni-ion affinity chromatography can be used to purify the expressed protein. See, Favacho et al. (2006) Protein expression and purification 46:196-203. See also, Zhou et al. (2007) The Protein J 26:29-37; Wang et al. (2006) Vaccine 15:2176-2185; and WO/2009/076778. Protectants may be used in the purification process such as osmotica, antioxidants, phenolic oxidation inhibitors, protease inhibitors, and the like.

Methods of Use and Article of Manufacture

The present invention includes the following method embodiments. In an embodiment, a method of vaccinating an animal comprising administering a composition comprising NDV antigenic polypeptide(s) or fragment or variant thereof and a pharmaceutical or veterinarily acceptable carrier, excipient, or vehicle to an animal is disclosed. In one aspect of this embodiment, the animal is an avian, an equine, a canine, a feline or a porcine.

In yet another embodiment, the vaccine or composition may be administered to one-day-old or older chickens.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

In the present invention a recombinant viral vector is used to express an NDV coding sequence or fragments thereof encoding an antigenic NDV polypeptide or fragment or variant thereof. Specifically, the viral vector can express an NDV sequence, more specifically an NDV HN gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TRO-VAC; see e.g., U.S. Pat. Nos. 5,505,941, 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The NDV polypeptide, antigen, epitope or immunogen may be an NDV HN. For example, the TROVAC vector comprising the NDV HN or F may be vectors as described in U.S. Pat. No. 7,144,578 and US 2008/0188640, the ILTV vector comprising the NDV antigens including HN and F may be vectors as described in U.S. Pat. Nos. 6,306,400 and 6,153,199. The NDV polypeptide or antigen of the invention to be expressed in a viral vector is inserted under the control of a specific poxvirus promoter, e.g., the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In another aspect of the prime-boost protocol or regime of the invention, a composition comprising an NDV antigen of the invention is administered followed by the administration of a recombinant viral vector or a plasmid vector that contains and expresses an NDV antigen and/or variants or fragments thereof in vivo. Likewise, a prime-boost protocol may comprise the administration of a recombinant viral vector or a plasmid vector followed by the administration of a recombinant NDV antigen of the invention. It is further noted that both the primary and the secondary administrations may comprise the recombinant NDV antigen of the invention. Thus, the recombinant NDV antigen of the invention may be administered in any order with a viral vector or alternatively may be used alone as both the primary and secondary compositions.

In yet another aspect of the prime-boost protocol of the invention, a composition comprising an NDV antigen of the invention is administered followed by the administration of an inactivated viral composition or vaccine comprising the NDV antigen. Likewise, a prime-boost protocol may comprise the administration of an inactivated viral composition or vaccine followed by the administration of a recombinant NDV antigen of the invention. It is further noted that both the primary and the secondary administrations may comprise the recombinant antigenic polypeptide of the invention. The antigenic polypeptides of the invention may be administered in any order with an inactivated viral composition or vaccine or alternatively may be used alone as both the primary and secondary compositions.

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of avian compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The compositions comprising the recombinant antigenic polypeptides of the invention used in the prime-boost protocols are contained in a pharmaceutically or veterinary acceptable vehicle, diluent or excipient. The protocols of the invention protect the animal from NDV and/or prevent disease progression in an infected animal.

The various administrations are preferably carried out 1 to 6 weeks apart. According to one embodiment, an annual booster is also envisioned. The animals are at least one-day-old at the time of the first administration.

The efficacy of the vaccines may be tested about 2 to 4 weeks after the last immunization by challenging animals, such as avian, with a virulent strain of NDV. Both homologous and heterologous strains are used for challenge to test the efficacy of the vaccine. The animal may be challenged by spray, intra-nasally, intra-ocularly, intra-tracheally, and/or orally. The challenge viral may be about $10^{5-8}$ $EID_{50}$ in a volume depending upon the route of administration. For example, if the administration is by spray, a virus suspension is aerosolized to generate about 1 to 100 μm droplets, if the administration is intra-nasal, intra-tracheal or oral, the volume of the challenge virus is about 0.5 ml, 1-2 ml, and 5-10 ml, respectively. Animals may be observed daily for 14 days following challenge for clinical signs, for example, dehydration and pasty vents. In addition, the groups of animals may be euthanized and evaluated for pathological findings of pulmonary and pleural hemorrhage, tracheitis, bronchitis, bronchiolitis, and bronchopneumonia. Orophayngeal swabs may be collected from all animals post challenge for virus isolation. The presence or absence of viral antigens in respiratory tissues may be evaluated by quantitative real time reverse transcriptase polymerase chain reaction (qRRT-PCR). Blood samples may be collected before and post-challenge and may be analyzed for the presence of NDV-specific antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the subject matter disclosed herein provides a vaccination regime and detection method for differentiation between infected and vaccinated animals (DIVA).

A strategy that allows "differentiation of infected from vaccinated animals" (DIVA), has been put forward as a possible solution for the eventual eradication of virus without involving mass culling of birds and the consequent economic damage, especially in developing countries (Food and Agriculture Organization of the United (FAO) (2004). FAO, OIE & WHO Technical consultation on the Control of NDV. Animal health special report). This strategy has the benefits of vaccination (less virus in the environment) with the ability to identify infected flocks which still allows the implementation of other control measures, including stamping out. At the flock level, a simple approach is to regularly monitor sentinel birds left unvaccinated in each vaccinated flock, but this may cause some management problems, particularly in identifying the sentinels in large flocks. As an alternative, testing for field exposure may be performed on the vaccinated birds. Alternatively the use of vaccines that contains only NDV HN subunit (protein) would allow classical AGID and NP- or matrix-based ELISAs to be used to detect infection in vaccinated birds.

It is disclosed herein that the use of the vaccine or composition of the present invention allows the detection of NDV infection in a vaccinated animal using available diagnosis test aiming to detect antibody response against NDV proteins other than HA such as agar gel immunodiffusion or NP-based ELISA. It is disclosed herein that the use of the vaccine or composition of the present invention allows the detection of the infection in animals by differentiating between infected and vaccinated animals (DIVA). A method is disclosed herein for diagnosing the infection of NDV in an animal using NP-based immunogenic detection method, such as, NP-based ELISA. In one embodiment, the subject matter disclosed herein is directed to a method of diagnosing NDV infection in an animal, comprising: a) contacting a solid substrate comprising a nucleoprotein (NP) with a sample obtained from the animal; b) contacting the solid substrate with a monoclonal antibody (MAb) against the NP; and c) detecting binding of the MAb to the sample captured by the NP on the solid substrate, wherein the percentage inhibition of test sample relative to the negative control indicates that the subject is infected with NDV, thereby diagnosing NDV infection in the subject.

Another embodiment of the invention is a kit for performing a method of eliciting or inducing an immunological or protective response against NDV in an animal comprising a recombinant NDV HN immunological composition or vaccine and instructions for performing the method of delivery in an effective amount for eliciting an immune response in the animal.

In an embodiment, the subject matter disclosed herein is directed to a kit for performing a method of eliciting or inducing an immune response which may comprise any one of the recombinant NDV immunological compositions or vaccines, or inactivated NDV immunological compositions or vaccines, recombinant NDV viral compositions or vaccines, and instructions for performing the method.

Another embodiment of the invention is a kit for performing a method of inducing an immunological or protective response against NDV in an animal comprising a composition or vaccine comprising an NDV antigen of the invention and a recombinant NDV viral immunological composition or vaccine, and instructions for performing the method of delivery in an effective amount for eliciting an immune response in the animal.

Another embodiment of the invention is a kit for performing a method of inducing an immunological or protective response against NDV in an animal comprising a composition or vaccine comprising an NDV antigen of the invention and an inactivated NDV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

In one embodiment, the invention provides for the administration of a therapeutically effective amount of a vaccine or composition for the delivery and expression of an NDV HN antigen or epitope in a target cell. Determination of the therapeutically effective amount is routine experimentation for one of ordinary skill in the art. In one embodiment, the vaccine or composition comprises a recombinant NDV HN polypeptide, antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector or recombinant proteins; advantageously, the carrier, vehicle or excipient may facilitate transfection and/or improve preservation of the vector or protein. Doses and dose volumes are herein discussed in the general description and can also be determined by the skilled artisan from this disclosure read in conjunction with the knowledge in the art, without any undue experimentation.

The cationic lipids containing a quaternary ammonium salt which are, but not exclusively suitable for plasmids, those having the following formula:

$$R_1-O-CH_2-CH-CH_2-\overset{\overset{CH_3}{|+}}{\underset{\underset{CH_3}{|}}{N}}-R_2-X$$
$$\phantom{R_1-O-CH_2-}\underset{OR_1}{|}$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1:about 1, e.g., 1:1.

In another embodiment, pharmaceutically or veterinarily acceptable carrier, excipient, vehicle, or adjuvant may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. The water-in-oil emulsion may comprise 75% oil phase containing mineral oil and 4% SPAN 80® and 25% aqueous phase containing 0.4% TWEEN 80®. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). The WOW triple emulsion may comprise 60% oil phase containing mineral oil and 6% SPAN 80® and 40% aqueous phase containing 1.6% TWEEN 80®. Examples of other suitable emulsions are described in U.S. Pat. No. 7,371,395.

The immunological compositions and vaccines according to the invention may comprise or consist essentially of one or more pharmaceutically or veterinarily acceptable carriers, excipients, vehicles, or adjuvants. Suitable carriers or adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

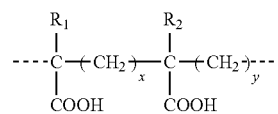

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to avians).

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant microalgal or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Construction of Vectors for the NDV HN Gene and Transformation

The vector pAB0018 (ATCC deposit no. PTA9616) was digested with BamHI and NdeI resulting in two fragments of 838 bp and 9879 bp. The larger fragment was fractionated by standard electrophoretic techniques in an agar gel, and purified using commercial DNA purification kits. This 9879 bp fragment was ligated to a codon-optimized NDV HN gene (SEQ ID NO:1) which had also been previously digested with BamHI and NdeI. The ligation was then used to transform commercially supplied strains of competent E. coli DH5-α cells (Invitrogen, Carlsbad, Calif., USA) using the manufacturer's protocols. These plasmids were then screened by restriction digests or PCR to confirm that the ligation generated the expected plasmid structures. One such plasmid vector resulting from this procedure was verified by Sanger sequencing and designated pCL0081. The specific nucleic acid sequence of NDV HN gene has been optimized for expression in Schizochytrium sp. Additionally, the vector pCL0081 contained a selection marker cassette conferring resistance to Schizochytrium transformants grown in the presence of sulfometuron methy, a promoter from the Schizochytrium elongation factor-1 gene (EF1) to drive expression of the HN transgene, and following the HN transgene, and the OrfC terminator (also known as the PFA3 terminator).

Schizochytrium sp. (ATCC 20888) was used as a host for transformation with the vector pCL0081 using electroporation method. Cells were grown in M50-20 media on a shaker at 200 rpm for 48 hrs at 29° C. The cells were diluted at 1:100 into fresh media and grown overnight. The cells were centrifuged and resuspended in 1 M mannitol, 10 mM CaCl2 (pH 5.5) to a final concentration of 2 $OD_{600}$ units. 5 mL of cells were mixed with 0.25 mg/mL Protease XIV (Sigma Chemical) and incubated on a shaker for 4 hrs. The cells were washed twice with 10% ice cold glycerol and resuspended in 500 uL of cold 10% glycerol. 90 uL was aliquoted into a prechilled 0.2 cm gap electro-cuvettes (Biorad 165-2086). 10 ul of DNA (1-5 ug) was added to the cuvette and mixed gently and held on ice. Cells were electroporated at 200 ohms (resistance), 25 uF, 250V (0.1 cm gap) 500V (0.2 cm gap). 0.5 mL of media was added immediately to the cuvette. The cells were then transferred to 4.5 mL of M50-20 media and incubated for 2-3 hrs at 100 rpm on a shaker. The cells were centrifuged and resuspended in 0.5 mL of media and plated onto 2-5 M2B plates with appropriate selection (if needed) and incubated at 29° C.

Example 2 HA Analysis of Algae Transformants

Cryostocks of transgenic strains of Schizochytrium (transformed with pCL0081) were grown in M50-20 (described in US 2008/0022422) to confluency, then propagated in 50 mL baffled shake flasks at 27° C., 200 rpm for 48 hours in a medium containing (per liter) 13.62 g $Na_2SO_4$, 0.72 g $K_2SO_4$, 0.56 g KCl, 2.27 g $MgSO_4.7H_2O$, 3 g $(NH_4)_2SO_4$, 0.19 g $CaCl_2.2H_2O$, 3 g MSG monohydrate, 21.4 g MES, and 0.4 g $KH_2PO_4$. The volume was brought to 900 mL with deionized $H_2O$ and the pH was adjusted to 6 before autoclaving for 35 min. Filter-sterilized glucose (50 g/L), vitamins (2 mL/L) and trace metals (2 mL/L) were then added to the medium and the volume was adjusted to one liter. The vitamin solution contained 0.16 g/L vitamin B12, 9.75 g/L thiamine, 3.33 g/L Ca-pentothenate. The trace metal solution (pH 2.5) contained 1.00 g/L citric acid, 5.15 g/L $FeSO_4.7H_2O$, 1.55 g/L $MnCl_2.4H_2O$, 1.55 g/L $ZnSO_4.7H_2O$, 0.02 g/L $CoCl_2.6H_2O$, 0.02 g/L $Na_2MoO_4.2H_2O$, 1.035 g/L $CuSO_4.5H_2O$, 1.035 g/L $NiSO_4.6H_2O$. All reagents were available commercially.

Schizochytrium cultures were transferred to 50 mL conical tubes and centrifuged at 3000 g for 15 min. This low-speed supernatant was used, as is, for hemagglutination activity assay. A portion of the low-speed supernatant was further centrifugated at 100,000 g for one hour. The resulting pellet, insoluble fraction containing the HN protein, was resuspended in phosphate buffer saline (PBS) and used for peptide sequence analysis as well as glycosylation analysis.

The expression of the HN protein by *Schizochytrium* was first evaluated by an activity assay. The functional HN protein displays an hemagglutination activity which was readily detected by a standard hemagglutination activity assay. Briefly, 50 uL of doubling dilutions of low speed supernatant in PBS were prepared in a 96-well microtiter plate. Equal volume of an approximate 1% solution of turkey red blood cells (Fitzgerald Industries, Acton, Mass., USA) in PBS was then added to each well followed by incubation at room temperature for 30 min. The degree of agglutination was then analyzed visually. The hemagglutination activity unit (HAU) is defined as the highest dilution of low-speed supernatant that causes visible hemagglutination in the well. Typical activity was found to be in the order of 512 HAU in transgenic strain "CL0081-23" (FIG. 3B). PBS or the wild-type strain of *Schizochytrium* sp. ATCC 20888, grown and prepared in the same manner as the transgenic strains, was used as a negative control and did not show any hemagglutination activity. An NDV Hemagglutinin (HA) recombinant protein was used as a positive control. Sample titer was scored at the highest dilution before the defined button was observed. HA activity was detected in raw supernatant (FIG. 3A). HAU in concentrated supernatant sample is 3200 HAU/50 ul. The hemagglutination activity was found to be stable through multiple rounds of freeze/thaw.

Example 3 Expression Analysis of Algae Transformants

The expression of the HN protein was also verified by immunoblot analysis following standard immunoblotting procedure. The proteins were separated by sodium dodecyl sulfate-polyacrylamide gel electrophoresis (SDS-PAGE) on a 4-12% bis-tris gel (Invitrogen). The proteins were then stained with Coomassie blue (SimplyBlue Safe Stain, Invitrogen) or transferred onto polyvinylidene fluoride membrane and probed for the presence of HN protein with anti-NDV antiserum from chicken in 1:1000 dilution (Charles River laboratories, Wilmington, Mass., USA) followed by anti-chicken secondary antibody coupled to alkaline phosphatase in 1:5000 dilution (AP-AffiniPure Goat Anti-Chicken #103-055-155, Jackson ImmunoResearch Laboratories, Inc., West Grove, Pa., USA). Membrane was then treated with 5-bromo-4-chloro-3-indoyl-phosphate/nitroblue tetrazolium solution (BCIP/NBT) according to the manufacturer's instructions (KPL, Gaithersburg, Md.). An example is presented in FIG. 4 for the transgenic strain "CL0081-23". Coomassie blue-stained gels and corresponding anti-NDV immunoblots are presented in panels B and C. The recombinant HN protein was detected in the low-speed supernatant (panel B) and in the insoluble fraction (panel C). The negative control (−Ctrl) was the wild-type strain of *Schizochytrium* sp. ATCC 20888 or the transgenic strain "AB0018".

Example 4 Glycosylation Analysis

The presence of glycans on the HN protein was first evaluated by enzymatic treatment. The insoluble fraction of the transgenic strain "CL0081-23" was resuspended in PBS and digested with EndoH or PNGase F according to manufacturer's instructions (New England Biolabs, Ipswich, Mass., USA). Removal of glycans was then identified by the expected shift in mobility when separating the proteins on 12% SDS-PAGE stained with Coomassie blue, periodic acid, or immunobloted with anti-NDV antiserum (FIG. 5, panel A). The negative control (−Ctrl) of immunoblotting was the transgenic strain "AB0018". The negative control for the enzymatic treatment was the transgenic strain "CL0081-23" incubated without enzymes (non-treated NT). Second, the glycosylation profile of the HN protein produced in *Schizochytrium* was analyzed by matrix-assisted laser-desorption ionization time-of-flight mass spectrometry and NanoSpray ionization-Linear Ion trap Mass spectrometry (Complex Carbohydrate Research Center, Georgia). Coomassie blue-stained gel slices of the proteins of interest were cut into smaller pieces (~1 $mm^3$) and destained alternately with 40 mM Ammonium bicarbonate (AmBic) and 100% acetonitrile until the color turned clear. Destained gel was reswelled in 10 mM DTT in 40 mM Ambic at 55° C. for 1 hr. The DTT solution was exchanged with 55 mM Iodoacetamide (IAM) and incubated in the dark for 45 min. Incubation was followed by washing alternately with 40 mM AmBic and 100% acetonitrile twice. Dehydrated gel was reswelled with trypsin solution (trypsin in 40 mM Ambic) on ice for 45 min initially, and protein digestion was carried out at 37° C. overnight. The supernatant was transferred into another tube. Peptides and the glycopeptides were extracted from the gel in series with 20% acetonitrile in 5% formic acid, 50% acetonitrile in 5% formic acid and then 80% acetonitrile in 5% formic acid. The sample solutions were dried and combined into one tube. Extracted tryptic digest was passed through a C18 sep-pak cartridge and washed with 5% acetic acid to remove contaminants (salts, SDS, etc.). Peptides and glycopeptides were eluted in series with 20% iso-propanol in 5% acetic acid, 40% iso-propanol in 5% acetic acid and 100% iso-propanol and dried in a speed vacuum concentrator. The dried samples were combined and then reconstituted with 50 mM sodium phosphate buffer (pH 7.5) and heated at 100° C. for 5 min to inactivate trypsin. The tryptic digest was incubated with PNGase F at 37° C. overnight to release N-glycans. After digestion, the sample was passed through a C18 sep-pak cartridge and the carbohydrate fraction was eluted with 5% acetic acid and dried by lyophilization. Released N-linked oligosaccharides were permethylated based on the method of Anumula and Taylor (Anumula and Taylor, 1992) and profiled by mass spectrometry. Mass spectrometric analysis was performed following the method developed at the Complex Carbohydrates Research Center (Aoki K, Perlman M, Lim J M, Cantu R, Wells L, Tiemeyer M. J Biol. Chem. 2007 Mar. 23; 282(12): 9127-42.). Mass analysis was determined by using NSI-LTQ/$MS_n$. Briefly, permethylated glycans were dissolved in 1 mM NaOH in 50% methanol and infused directly into the instrument (LTQ, Thermo Finnigan) at a constant flow rate of 0.4 μL/min. The MS analysis was performed in the positive ion mode. For total ion mapping, automated MS/MS analysis (at 35 collision energy), m/z range from 500 to 2000 was scanned in successive 2.8 mass unit windows that overlapped the preceding window by 2 mass units. Total ion mapping was performed to examine the presence of fragment ions indicative of glycans. All MS/MS data from m/z 500 through m/z 2000 were taken and then the raw data were analyzed manually. The chromatogram and table of species obtained by NSI-total ion mapping are shown in FIG. 5 (panels B and C). This chromatogram was processed by the scan filter, neutral loss of m/z 139, which is the one of characteristic neutral loss of high-mannose type glycans. Total ion mapping revealed that this sample contains a series of high-mannose type glycans with long mannose chain.

Example 5 Peptide Analysis of NDV HN

The insoluble fraction was separated by SDS-PAGE and stained with Coomassie blue or transferred to PVDF and immunoblotted with anti-NDV antiserum from chicken, as described above. The band corresponding to the cross-reaction in immunoblot was excised from the coomassie stained gel and submitted for peptide sequence analysis. The procedure consisted washing/destaining the bands of interest in 50% ethanol, 5% acetic acid. The gel pieces were then dehydrated in acetonitrile, dried in a Speed-vac, and digested with trypsin by adding 5 µL of 10 ng/µL trypsin in 50 mM ammonium bicarbonate and incubating overnight digestion at room temperature. The peptides that were formed were extracted from the polyacrylamide in two aliquots of 30 µL 50% acetonitrile with 5% formic acid. These extracts were combined and evaporated to <10 µL in Speed-vac and then resuspended in 1% acetic acid to make up a final volume of approximately 30 µL for LC-MS analysis. The LC-MS system was a Finnigan LTQ linear ion trap mass spectrometer system. The HPLC column was a self-packed 9 cm×75 µm id Phenomenex Jupiter C18 reversed-phase capillary chromatography column. Then µL volumes of the extract were injected and the peptides eluted from the column by an acetonitrile/0.1% formic acid gradient at a flow rate of 0.25 µL/min were introduced into the source of the mass spectrometer on-line. The microelectrospray ion source was operated at 2.5 kV. The digest was analyzed using a selective reaction (SRM) experiments in which the mass spectrometer fragments a series of m/z ratios over the entire course of the LC experiment. The fragmentation pattern of the peptides of interest was then used to produce chromatograms. The peak areas for each peptide was determined and normalized to an internal standard. The internal standards used in this analysis are proteins that have an unchanging abundance between the samples being studied. The final comparison between the two systems is determined by comparing the normalized peak ratios for each protein. The collision induced dissociation spectra were then searched against the ncbi database. The HN protein was identified by a total of 32 peptides covering 68% of the protein sequence. The results with the specific peptides that were sequenced are shown in FIG. 11.

Example 6 Vaccination of Chickens

Challenge studies were conducted in specific pathogen free (SPF) chickens vaccinated at 3 to 4 weeks of age with *Schizochytrium* expressed NDV HN protein in an adjuvant. Twelve chickens were assigned to each vaccine group. A Group vaccinated with *Schizochytrium* wild type material in the same adjuvant was included as a negative control group. Three groups of chickens were tested with one shot scheme at three dosage levels (100 HAU, 1000 HAU, and 10000 HAU). The water-in-oil emulsions of the *Schizochytrium* culture medium was given by the intramuscular route in the leg (0.5 ml per site×2). On day 27, blood samples were collected for hemagglutination inhibition test, and chickens were then challenged intramuscularly with Newcastle Disease Virus GB Texas strain at $10^{4.0}$ $EID_{50}$ per chicken (FIG. 12). The chickens were observed daily to ensure health status of the chickens being challenged. After challenge, the chickens were observed daily for fourteen days for severe clinical signs of NDV, such as but not limited to, extreme nervousness, respiratory distress, nervous signs or death. The mortality data shown in FIG. 12 indicate that vaccination with plant derived NDV HN elicits increased protection of 33% at a dose level of 100 HAU, and increased protection of 100% at dose levels of 1000 HAU and 9333 HAU over control.

Example 7 Expression, Characterization, Immunogenicity and Efficacy of NDV HN Protein Produced in Duckweed

*Lemna minor* protein expression system was used to express NDV HN polypeptide (SEQ ID NO:17, NDV strain YZCQ/Liaoning/08). The *L. minor* optimized HN gene (SEQ ID NO:22 and 23) was cloned into a modified *A. tumefaciens* binary vector (Gasdaska, J., et al., Bioprocessing J. 3, 50-56, 2003). Several vector constructs were made. The constructs contain Super Promoter, 5' leader from *Lemna gibba* RBCS SSU1, and the Nopaline synthase (Nos) terminator. Construct MerH01 contains codon-optimized NDV HN gene with its native signal sequence (signal anchor as shown in the plasmid maps). Construct MerH02 contains codon-optimized NDV HN gene with its native signal sequence and KDEL ER retention sequence. Construct MerH03 contains codon-optimized NDV HN gene (encoding mature HN protein) with the native NDV HN signal sequence replaced with alpha amylase signal sequence. Construct MerH04 contains codon-optimized NDV HN gene with its native signal sequence replaced with alpha amylase signal sequence, and KDEL ER retention sequence. The plasmid maps of the four constructs are shown in FIG. 7.3. The constructs were transformed to *A. tumefaciens* C58Z707 (Hepburn, A. G. et al., J. Gen. Microbiol. 131, 2961-2969, 1985). Using the *A. tumefaciens* C58Z707 transformed with plant transformation vector constructs, transgenic plants representing individual clonal lines were generated from rapidly growing *L. minor* nodules as described in Yamamoto, Y. et al., In Vitro Cell. Dev. Biol. 37, 349-353 (2001).

After the transgenic lines are generated, they are screened for expression of NDV HN in the media and the tissue. The plants are grown for two weeks in small research vessels and the resulting media and tissue are collected for analysis. For the tissue analysis, frozen tissue is homogenized, centrifuged and the supernatant is removed for standard hemagglutination assay. The highest lines from the initial screening are being scaled up to provide approximately 1 kg of biomass for further characterization, such as hemagglutination assay, hemagglutination inhibition assay (HI), SDS-PAGE, Western Blot, and immunolocalization.

Crude plant extract is prepared from transgenic *Lemna* line for evaluation of immunogenicity and efficacy in specific pathogen free (SPF) chickens at 3-4 weeks of age. Twelve chickens are assigned to each vaccine group vaccinated with the composition comprising the recombinant NDV HN polypeptide and an adjuvant. A group vaccinated with *Lemna* wild type material in the same adjuvant is included as a negative control. Other groups of chickens are tested with one shot scheme at different dosage levels. On day 21, blood samples are collected for hemagglutination inhibition test, and chickens are then challenged with different Newcastle Disease Virus strains. After the challenge, the chickens are observed daily for fourteen days for severe clinical signs of NDV, such as but not limited to, extreme nervousness, respiratory distress, nervous signs or death. The composition containing the recombinant NDV HN polypeptide shows efficacy in treating, protecting, and preventing NDV infection and disease.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A subunit vaccine comprising a recombinant Newcastle Disease Virus (NDV) Hemagglutinin-Neuraminidase (HN) antigenic polypeptide purified from microalgae and a pharmaceutically or veterinarily acceptable adjuvant, wherein the NDV HN antigenic polypeptide (i) has the sequence as set forth in SEQ ID NO: 3 and (ii) was expressed and glycosylated in the microalgae, wherein the pharmaceutically or veterinarily acceptable adjuvant is a water-in-oil emulsion, and wherein the subunit vaccine does not have other NDV polypeptides or antigens.

2. The subunit vaccine of claim 1, wherein the NDV HN antigenic polypeptide is partially purified.

3. The subunit vaccine of claim 1, wherein the NDV HN antigenic polypeptide is substantially purified.

4. The subunit vaccine of claim 1, wherein the NDV HN antigenic polypeptide was encoded by a polynucleotide having the sequence as set forth in SEQ ID NO: 1 or 2.

5. A method of vaccinating an animal susceptible to NDV comprising administering to the animal the subunit vaccine according to claim 1.

6. A method of vaccinating an animal susceptible to NDV according to a prime-boost regimen comprising: administering to the animal a prime-vaccine, and then administering to the animal a boost-vaccine, wherein at least one of the prime-vaccine and the boost-vaccine is the subunit vaccine according to claim 1.

7. The method of claim 6, wherein the prime-vaccine is the subunit vaccine according to claim 1, wherein the boost-vaccine comprises a recombinant viral vector in a pharmaceutically or veterinary acceptable vehicle or excipient, wherein the recombinant viral vector contains a polynucleotide that expresses, in vivo, a NDV HN polypeptide, variant, or fragment thereof, and wherein the method protects the animal from NDV infection and/or prevents disease progression in the animal.

8. The method of claim 6, wherein the prime-vaccine comprises a recombinant viral vector in a pharmaceutically or veterinary acceptable vehicle or excipient, wherein the recombinant viral vector contains a polynucleotide that expresses, in vivo, a NDV HN polypeptide, a variant, or fragment thereof, wherein the boost-vaccine is the subunit vaccine according to claim 1, and wherein the method protects the animal from NDV infection and/or prevents disease progression in the animal.

9. The method of claim 6, wherein the prime-vaccine is the subunit vaccine according to claim 1, and wherein the boost-vaccine comprises inactivated NDV, an NDV antigen, or a combination thereof.

10. The method of claim 6, wherein the prime-vaccine comprises inactivated NDV, an NDV antigen, or a combination thereof, and wherein the boost-vaccine is the subunit vaccine according to claim 1.

11. The subunit vaccine of claim 1, wherein the subunit vaccine is capable of eliciting an immune response in a host.

12. The method of claim 5, wherein the animal is avian, equine, canine, feline, or porcine.

* * * * *

SEQUENCE LISTING

<160> NUMBER OF SEQ ID NOS: 28

<210> SEQ ID NO 1
<211> LENGTH: 1716
<212> TYPE: DNA
<213> ORGANISM: artificial sequence
<220> FEATURE:
<223> OTHER INFORMATION: NDV HN codon-optimized DNA

<400> SEQUENCE: 1

```
atggaccgtg tcgtctcccg cgtggtcctc gagaacgagg agcgtgaggc caagaacacc     60
tggcgccttg tctttcgtgt cgccgtcctc tcccttattg tcatgaccct cgccatctcc    120
gtcgccgccc tcgtctacag catggaggct agcacccccca acgatctcgc cggaatctcg    180
actgttatct cccgcgccga ggaccgcgtc acctccctcc tcaactccaa ccaggatgtc    240
gttgatcgcg tctacaagca ggtcgccctc gagtcccctc tcgccctcct taacaccgag    300
agcatcatta tgaacgccat tacctccctc agctaccaga ttaacggcgc cgccaactcg    360
tccggctgcg gcgcccccgt ccatgaccct gattacatcg gcggcgtcgg caaggagctc    420
atcgtcgacg acactagcga tgccacgtcc ttctacccta gcgcctacca ggagcacctc    480
aacttcatcc ctgcccccac taccggctcc ggctgcaccc gcattcccag cttcgacatg    540
tccgccactc actactgcta cacccataac gtcatccttt cgggttgccg cgaccactcc    600
cacagccacc agtacctcgc cctcggagtt cttcgtacgt ccgccaccgg ccgcgtcttt    660
ttttccaccc tccgcagcat caacctcgac gatacccaga accgcaagag ctgctcggtc    720
tccgccaccc cgctcggctg cgacatgctc tgctccaagg tcaccgagac ggaggaggag    780
gattacaagt ccgttacccc cacttcgatg gtccacggcc gccttggctt cgacggccag    840
taccacgaga aggacctcga cgtcaccgtt ctctttaagg actgggttgc caactacccc    900
ggcgtcggcg gcggctccct catcgatgac cgcgtctggt ttcctgtcta cggtggtctc    960
aagcctaaca gcccctccga taccgcccag gagggtaagt acgtgatcta caagcgctac   1020
aacaacacct gccctgacga gcaggattac caggtccgca tggccaagtc ctcgtacaag   1080
cccggtcgtt tcggcggcaa gcgcgtccag caggccattc tctcgatcaa ggtctcgacc   1140
agcctcggag aggaccccgt gctcaccgtt ccccctaaca ccgtcaccct tatgggcgcc   1200
gagggccgca tcctcaccgt cggtacctcc cacttcctct accagcgcgg ctcgagctac   1260
ttttcccctg cccttcttta ccccatgact gttcgcaaca agactgctac cctccacagc   1320
ccctacacct ttaacgcctt cacgcgcccc ggaagcgtcc cctgccaggc gagcgcccgc   1380
tgccctaact cctgcattac cggcgtctac accgaccctt accctgtcgt ctttcaccgc   1440
aaccataccc ttcgcggcgt cttcggtact atgcttgata acgagcaggc ccgcctcaac   1500
cccgtctccg ccattttcga ctacacttcc cgctcccgta tcacccgcgt ctcctccacc   1560
tccaccaagg ccgcctacac cacctccacc tgctttaagg ttgtcaagac taacaaggtc   1620
tactgcctct ccatcgccga gattagcaac accctcttcg gagagttccg cattgtcccc   1680
ctgctcgtcg agatcctcaa ggacgatcgc gtttaa                             1716
```

<210> SEQ ID NO 2
<211> LENGTH: 1716

```
<212> TYPE: DNA
<213> ORGANISM: artificial sequence
<220> FEATURE:
<223> OTHER INFORMATION: NDV HN wild type DNA

<400> SEQUENCE: 2
atggatcgtg tagttagcag agtcgtacta gaaaacgaag aaagagaagc aaagaataca     60
tggcgcctgg ttttccgggt cgcagtccta tctctaatag taatgacatt agctatctct    120
gtagccgccc tggtatacag catggaggct agcacgccga acgaccttgc gggtatatcg    180
acggtgatct ccagggcaga ggatagggtt acatctttac tcaattcaaa tcaagatgtg    240
gtagataggg tatataaaca ggtggccctt gagtccccgc tggcgttgtt gaatactgag    300
tctataatta tgaatgcaat aacttctctt tcctatcaaa ttaatggggc tgcaaatagt    360
agtgggtgtg gggcacctgt tcatgacccg gattatattg gggggtagg taaagagctc    420 atagtagatg acacgagtga tgccacttca ttctatcctt cagcatatca agaacacctg    480
aactttatcc cggcgcccac cacaggttca ggctgcactc ggataccctc attcgacatg    540
agcgctaccc actattgtta tactcacaat gtgatattat ctggctgcag agatcactca    600
cactcacatc agtatttggc actaggtgtg cttcggacat ctgcaacagg gagggtattc    660
ttttctactc tgcgttccat caatttagat gacacccaaa atcggaagtc ttgcagtgtg    720
agtgcaactc ctttaggttg tgatatgctg tgctctaaag tcacagagac tgaggaggag    780
gattataagt cagttacccc cacatcaatg gtgcatggaa ggttagggtt tgacggtcag    840
taccatgaga aggacttaga cgtcacagtc ttatttaagg attgggttgc aaattacccg    900
ggagtgggag gagggtctct tattgacgac cgtgtatggt tcccagttta tggagggcta    960
aaacccaatt cacctagcga cactgcacaa gaagggaaat atgtaatata caagcgctat   1020
aataacacat gccccgatga acaagattac caagttcgga tggctaaatc ctcgtataag   1080
cctggacggt ttggtgggaa gcgcgtacag caagccatcc tatctatcaa agtatcaaca   1140
tctttgggcg aggacccggt gctgactgta ccgccaaata cagttacact catgggggcc   1200
gagggcagaa tcctcacagt aggaacatct catttcttgt accagcgagg gtcttcatac   1260
ttttctcccg ccttactata ccctatgaca gtgcgcaaca aaacagccac tcttcatagt   1320
ccttatacat ttaatgcgtt cactcggccg ggtagtgtcc cttgccaggc atcagcaagg   1380
tgccctaact catgtatcac tggagtctat actgatccgt accctgtagt cttccatagg   1440
aatcacacct tgcgaggggt gttcgggaca atgcttgata atgaacaagc aaggctcaat   1500
cccgtatctg caatatttga ctacacatct cgcagtcgca taacccgggt aagttcgacc   1560
agcaccaagg cagcatacac gacatcgaca tgttttaaag ttgtcaagac taataaagtg   1620
tattgtctta gcattgcaga aatatccaat actctatttg gggaattcag gatcgttcct   1680
ttactggtcg agattctcaa agatgatagg gtttaa                              1716

<210> SEQ ID NO 3
<211> LENGTH: 571
<212> TYPE: PRT
<213> ORGANISM: artificial sequence
<220> FEATURE:
<223> OTHER INFORMATION: NDV HN protein (ABS84265)

<400> SEQUENCE: 3

Met Asp Arg Val Val Ser Arg Val Val Leu Glu Asn Glu Glu Arg Glu
1               5                   10                  15

Ala Lys Asn Thr Trp Arg Leu Val Phe Arg Val Ala Val Leu Ser Leu
```

```
            20                  25                  30
Ile Val Met Thr Leu Ala Ile Ser Val Ala Ala Leu Val Tyr Ser Met
                35                  40                  45
Glu Ala Ser Thr Pro Asn Asp Leu Ala Gly Ile Ser Thr Val Ile Ser
            50                  55                  60
Arg Ala Glu Asp Arg Val Thr Ser Leu Leu Asn Ser Asn Gln Asp Val
65                  70                  75                  80
Val Asp Arg Val Tyr Lys Gln Val Ala Leu Glu Ser Pro Leu Ala Leu
                85                  90                  95
Leu Asn Thr Glu Ser Ile Ile Met Asn Ala Ile Thr Ser Leu Ser Tyr
            100                 105                 110
Gln Ile Asn Gly Ala Ala Asn Ser Ser Gly Cys Gly Ala Pro Val His
            115                 120                 125
Asp Pro Asp Tyr Ile Gly Gly Val Gly Lys Glu Leu Ile Val Asp Asp
            130                 135                 140
Thr Ser Asp Ala Thr Ser Phe Tyr Pro Ser Ala Tyr Gln Glu His Leu
145                 150                 155                 160
Asn Phe Ile Pro Ala Pro Thr Thr Gly Ser Gly Cys Thr Arg Ile Pro
            165                 170                 175
Ser Phe Asp Met Ser Ala Thr His Tyr Cys Tyr Thr His Asn Val Ile
            180                 185                 190
Leu Ser Gly Cys Arg Asp His Ser His Ser His Gln Tyr Leu Ala Leu
            195                 200                 205
Gly Val Leu Arg Thr Ser Ala Thr Gly Arg Val Phe Phe Ser Thr Leu
            210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Val Thr Glu
                245                 250                 255
Thr Glu Glu Asp Tyr Lys Ser Val Thr Pro Thr Ser Met Val His
            260                 265                 270
Gly Arg Leu Gly Phe Asp Gly Gln Tyr His Glu Lys Asp Leu Asp Val
            275                 280                 285
Thr Val Leu Phe Lys Asp Trp Val Ala Asn Tyr Pro Gly Val Gly Gly
            290                 295                 300
Gly Ser Leu Ile Asp Asp Arg Val Trp Phe Pro Val Tyr Gly Gly Leu
305                 310                 315                 320
Lys Pro Asn Ser Pro Ser Asp Thr Ala Gln Glu Gly Lys Tyr Val Ile
                325                 330                 335
Tyr Lys Arg Tyr Asn Asn Thr Cys Pro Asp Glu Gln Asp Tyr Gln Val
            340                 345                 350
Arg Met Ala Lys Ser Ser Tyr Lys Pro Gly Arg Phe Gly Gly Lys Arg
            355                 360                 365
Val Gln Gln Ala Ile Leu Ser Ile Lys Val Ser Thr Ser Leu Gly Glu
            370                 375                 380
Asp Pro Val Leu Thr Val Pro Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Arg
            420                 425                 430
Asn Lys Thr Ala Thr Leu His Ser Pro Tyr Thr Phe Asn Ala Phe Thr
            435                 440                 445
```

```
Arg Pro Gly Ser Val Pro Cys Gln Ala Ser Ala Arg Cys Pro Asn Ser
        450                 455                 460
Cys Ile Thr Gly Val Tyr Thr Asp Pro Tyr Pro Val Val Phe His Arg
465                 470                 475                 480
Asn His Thr Leu Arg Gly Val Phe Gly Thr Met Leu Asp Asn Glu Gln
                485                 490                 495
Ala Arg Leu Asn Pro Val Ser Ala Ile Phe Asp Tyr Thr Ser Arg Ser
            500                 505                 510
Arg Ile Thr Arg Val Ser Ser Thr Ser Lys Ala Ala Tyr Thr Thr
        515                 520                 525
Ser Thr Cys Phe Lys Val Val Lys Thr Asn Lys Val Tyr Cys Leu Ser
    530                 535                 540
Ile Ala Glu Ile Ser Asn Thr Leu Phe Gly Glu Phe Arg Ile Val Pro
545                 550                 555                 560
Leu Leu Val Glu Ile Leu Lys Asp Asp Arg Val
                565                 570

<210> SEQ ID NO 4
<211> LENGTH: 1915
<212> TYPE: DNA
<213> ORGANISM: artificial sequence
<220> FEATURE:
<223> OTHER INFORMATION: NDV HN DNa (M21409)

<400> SEQUENCE: 4
gtcctcagtc atggaccgcg cagttagcca agttgcgtta gagaatgatg aaagagaggc      60
aaaaaataca tggcgcttga tattccggat tgcaatctta ctcttaacag tagtgacctt     120
agctacatct gtagcctccc ttgtatatag catgggggct agcacaccta gcgaccttgt     180
aggcataccg accaggattt ccagggcaga agaaaagatt acatctgcac ttggttccaa     240
tcaagatgta gtagatagga tatataagca agtggccctt gagtctccgt ggcattgtt      300
aaacactgag actacaatta tgaacgcaat aacatctctc tcttatcaga ttaatggagc     360
tgcgaacaac agcgggtggg gggcacctat ccatgaccca gattttatcg ggggatagg      420
caaagaactc attgtagatg atgctagtga tgtcacatca ttctatccct ctgcatttca     480
agaacatcat aattttatcc cggcgcctac tacaggatca ggttgcattc ggataccttc     540
atttgacatg agtgctaccc cattactgcta cactcataat ataatatcgt ctggatgcag     600
agatcactca cactcatatc agtatttagc acttggtgtg ctccggactt ctgcaacagg     660
gaggatattc ttttctactc tgcgttccat caatctggat gacacccaga tcggaagtc      720
ttgcagtgtg agtgcaactc ccttaggttg tgatatgctg tgctcgaaag tcacggagac     780
agaggaagaa gattataact cagctgtccc tacgctgatg gtacatggga ggttagggtt     840
cgacggccaa taccacgaaa aggacctaga cgtcacaaca ttatttgagg actgggtggc     900
caactaccca ggagtagggg gtggatcttt tattgacagc gcgtatggt tctcagtcta      960
cggagggctg aaacccaatt cacccagtga cactgtacag gaagagaaat atgtaatata    1020
caagcgatac aatgacacat gcccagatga gcaagactac cagatccgaa tggccaagtc    1080
ttcgtataag cccgggcggt ttggtgggaa acgcatacag caggctatct tatctatcaa    1140
ggtgtcaaca tctttgggcg aagacccagt actgactgta ccgcccaaca cagtcacact    1200
catgggggcc gaaggcagaa ttctcacagt agggacatct catttcttgt atcagcgagg    1260
gtcatcatac ttctctcccg cgttattata tcctatgaca gtcagcaaca aaacagccac    1320
```

```
tcttcatagt ccctatacat tcaatgcctt cactcggcca ggtagtatcc cttgccaggc    1380
ttcagcaaga tgccccaact cgtgtgttac tggagtctat acagatccat atccctaat     1440 cttctatagg aaccacacct tgcgaggggt attcgggaca atgcttgatg gtgaacaagc    1500
aagacttaat cctgcgtctg cagtattcga tagcacatcc cgcagtcgca taacccgagt    1560
gagttcaagc agcaccaaag cagcatacac aacatcaact tgttttaaag ttgtcaagac    1620
caataagacc tattgtctca gcattgctga aatatctaat actctcttcg gagaattcag    1680
aatcgtcccg ttactagttg agatcctcaa aaatgatggg gttagagaag ccaggtctgg    1740
ttagttgagt caactatgaa agagctggaa agatggcatt gtatcaccta tcttccgcga    1800
caccaagaat caaactgaat gccggtgcga gctcgaattc catgtcgcca gttgaccaca    1860
atcagccagt gctcatgcga tcagatcaag tcttgtcaat agtccctcga ttaag         1915
```

<210> SEQ ID NO 5
<211> LENGTH: 577
<212> TYPE: PRT
<213> ORGANISM: artificial seuence
<220> FEATURE:
<223> OTHER INFORMATION: NDV HN protein (P12553)

<400> SEQUENCE: 5

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Leu Leu
            20                  25                  30

Thr Val Val Thr Leu Ala Thr Ser Val Ala Ser Leu Val Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Ala Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Phe Ile Gly Gly Ile Gly Lys Glu Leu Ile Val Asp Asp
    130                 135                 140

Ala Ser Asp Val Thr Ser Phe Tyr Pro Ser Ala Phe Gln Glu His
145                 150                 155                 160

Asn Phe Ile Pro Ala Pro Thr Thr Gly Ser Gly Cys Ile Arg Ile Pro
                165                 170                 175

Ser Phe Asp Met Ser Ala Thr His Tyr Cys Tyr Thr His Asn Ile Ile
            180                 185                 190

Ser Ser Gly Cys Arg Asp His Ser His Ser Tyr Gln Tyr Leu Ala Leu
        195                 200                 205

Gly Val Leu Arg Thr Ser Ala Thr Gly Arg Ile Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Leu Met Val His
```

-continued

```
                260             265             270
Gly Arg Leu Gly Phe Asp Gly Gln Tyr His Glu Lys Asp Leu Asp Val
            275                 280                 285
Thr Thr Leu Phe Glu Asp Trp Val Ala Asn Tyr Pro Gly Val Gly Gly
            290                 295                 300
Gly Ser Phe Ile Asp Ser Arg Val Trp Phe Ser Val Tyr Gly Gly Leu
305                 310                 315                 320
Lys Pro Asn Ser Pro Ser Asp Thr Val Gln Glu Glu Lys Tyr Val Ile
                325                 330                 335
Tyr Lys Arg Tyr Asn Asp Thr Cys Pro Asp Glu Gln Asp Tyr Gln Ile
                340                 345                 350
Arg Met Ala Lys Ser Ser Tyr Lys Pro Gly Arg Phe Gly Gly Lys Arg
            355                 360                 365
Ile Gln Gln Ala Ile Leu Ser Ile Lys Val Ser Thr Ser Leu Gly Glu
            370                 375                 380
Asp Pro Val Leu Thr Val Pro Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Ser
                420                 425                 430
Asn Lys Thr Ala Thr Leu His Ser Pro Tyr Thr Phe Asn Ala Phe Thr
            435                 440                 445
Arg Pro Gly Ser Ile Pro Cys Gln Ala Ser Ala Arg Cys Pro Asn Ser
            450                 455                 460
Cys Val Thr Gly Val Tyr Thr Asp Pro Tyr Pro Leu Ile Phe Tyr Arg
465                 470                 475                 480
Asn His Thr Leu Arg Gly Val Phe Gly Thr Met Leu Asp Gly Glu Gln
                485                 490                 495
Ala Arg Leu Asn Pro Ala Ser Ala Val Phe Asp Ser Thr Ser Arg Ser
            500                 505                 510
Arg Ile Thr Arg Val Ser Ser Ser Thr Lys Ala Ala Tyr Thr Thr
            515                 520                 525
Ser Thr Cys Phe Lys Val Val Lys Thr Asn Lys Thr Tyr Cys Leu Ser
            530                 535                 540
Ile Ala Glu Ile Ser Asn Thr Leu Phe Gly Glu Phe Arg Ile Val Pro
545                 550                 555                 560
Leu Leu Val Glu Ile Leu Lys Asn Asp Gly Val Arg Glu Ala Arg Ser
                565                 570                 575
Gly
```

<210> SEQ ID NO 6
<211> LENGTH: 2002
<212> TYPE: DNA
<213> ORGANISM: artificial sequence
<220> FEATURE:
<223> OTHER INFORMATION: NDV HN DNA (M24709)

<400> SEQUENCE: 6

```
acgggtagaa cggtaagaga ggccgcccct caattgcgag ccaggcttca caacctccgt    60
tctaccgctt caccgacaac agtcctcaat catggaccgc gccgttagcc aagttgcgtt   120
agagaatgat gaaagagagg caaaaaatac atgcgcttg atattccgga ttgcaatctt   180
attcttaaca gtagtgacct tggctatatc tgtagcctcc cttttatata gcatgggggc   240
```

```
tagcacacct agcgatcttg taggcatacc gactaggatt tccagggcag aagaaaagat    300
tacatctaca cttggttcca atcaagatgt agtagatagg atatataagc aagtggccct    360
tgagtctccg ttggcattgt taaaaactga gaccacaatt atgaacgcaa taacatctct    420
ctcttatcag attaatggag ctgcaaacaa cagcgggtgg ggggcaccta tccatgaccc    480
agattatata gggggatag gcaaagaact cattgtagat gatgctagtg atgtcacatc    540
attctatccc tctgcatttc aagaacatct gaatttatc ccggcgccta ctacaggatc    600
aggttgcact cgaatacctt catttgacat gagtgctacc cattactgct acacccataa    660
tgtaatattg tctggatgca gagatcactc acattcatat cagtatttag cacttggtgt    720
gctccggaca tctgcaacag ggagggtatt cttttctact ctgcgttcca tcaacctgga    780
cgacacccaa aatcggaagt cttgcagtgt gagtgcaact ccctgggtt gtgatatgct    840 gtgctcgaaa gtcacggaga cagaggaaga agattataac tcagctgtcc ctacgcggat    900
ggcacatggg aggttagggt tcgacggcca ataccacgaa aaggacctag atgtcacaac    960
attattcggg gactgggtgg ccaactaccc aggagtaggg ggtggatctt ttattgacgg   1020
ccgcgtatgg ttctcagtct acggaggggct gaaacccaat tcacccagtg acactgtaca   1080
ggaagggaaa tatgtgatat acaagcgata caatgacaca tgcccagatg agcaagacta   1140
ccagattcga atggccaagt cttcgtataa gcctggacgg ttggtgggaa acgcatcca   1200 gcaggctatc ttatctatca aggtgtcaac atccttaggc gaagacccgg tactgactgt   1260
accgcccaac acagtcacac tcatggggggc cgaaggcaga attctcacag tagggacatc   1320
tcatttcttg tatcaacgag ggtcatcata cttctctccc cgcgttattat atcctatgac   1380 agtcagcaac aaaacagcca ctcttcatag tccttataca ttcaatgcct tcactcggcc   1440
aggtagtatc ccttgccagg cttcagcaag atgccccaac ccgtgtgtta ctggagtcta   1500
tacagatcca tatcccctaa tcttctatag aaaccacacc ttgcgagggg tattcgggac   1560
aatgcttgat ggtgtacaag caagacttaa tcctacgtct gcagtattcg atagcacatc   1620
ccgcagtcgc ataactcgag tgagttcaag cagcaccaaa gcagcataca acatcaac   1680 ttgtttttaaa gtggtcaaga ccaataagac ctattgtctc agcattgctg aaatatctaa   1740
tactctcttc ggagaattca gaatcgtccc gttactagtt gagatcctca agatgacgg   1800 ggttagagaa gccaggtctg gctagttgag tcaattataa aggagttgga agatggcat   1860 tgtatcacct atcttctgcg acatcaagaa tcaaaccgaa tgccggcgcg tgctcgaatt   1920
ccatgttgcc agttgaccac aatcagccag tgctcatgcg atcagattaa gccttgtcaa   1980
tagtctcttg attaagaaaa aa                                            2002
```

<210> SEQ ID NO 7
<211> LENGTH: 577
<212> TYPE: PRT
<213> ORGANISM: artificial sequence
<220> FEATURE:
<223> OTHER INFORMATION: NDV HN protein (AAA46659)

<400> SEQUENCE: 7

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

-continued

```
Gly Ala Ser Thr Pro Ser Asp Leu Val Gly Ile Pro Thr Arg Ile Ser
    50                  55                  60
Arg Ala Glu Glu Lys Ile Thr Ser Thr Leu Gly Ser Asn Gln Asp Val
 65                  70                  75                  80
Val Asp Arg Ile Tyr Lys Gln Val Ala Leu Glu Ser Pro Leu Ala Leu
                 85                  90                  95
Leu Lys Thr Glu Thr Thr Ile Met Asn Ala Ile Thr Ser Leu Ser Tyr
            100                 105                 110
Gln Ile Asn Gly Ala Ala Asn Asn Ser Gly Trp Gly Ala Pro Ile His
            115                 120                 125
Asp Pro Asp Tyr Ile Gly Gly Ile Gly Lys Glu Leu Ile Val Asp Asp
130                 135                 140
Ala Ser Asp Val Thr Ser Phe Tyr Pro Ser Ala Phe Gln Glu His Leu
145                 150                 155                 160
Asn Phe Ile Pro Ala Pro Thr Thr Gly Ser Gly Cys Thr Arg Ile Pro
                165                 170                 175
Ser Phe Asp Met Ser Ala Thr His Tyr Cys Tyr Thr His Asn Val Ile
                180                 185                 190
Leu Ser Gly Cys Arg Asp His Ser His Ser Tyr Gln Tyr Leu Ala Leu
            195                 200                 205
Gly Val Leu Arg Thr Ser Ala Thr Gly Arg Val Phe Phe Ser Thr Leu
        210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Val Thr Glu
                245                 250                 255
Thr Glu Glu Glu Asp Tyr Asn Ser Ala Val Pro Thr Arg Met Ala His
            260                 265                 270
Gly Arg Leu Gly Phe Asp Gly Gln Tyr His Glu Lys Asp Leu Asp Val
        275                 280                 285
Thr Thr Leu Phe Gly Asp Trp Val Ala Asn Tyr Pro Gly Val Gly Gly
    290                 295                 300
Gly Ser Phe Ile Asp Gly Arg Val Trp Phe Ser Val Tyr Gly Gly Leu
305                 310                 315                 320
Lys Pro Asn Ser Pro Ser Asp Thr Val Gln Glu Gly Lys Tyr Val Ile
                325                 330                 335
Tyr Lys Arg Tyr Asn Asp Thr Cys Pro Asp Glu Gln Asp Tyr Gln Ile
            340                 345                 350
Arg Met Ala Lys Ser Ser Tyr Lys Pro Gly Arg Phe Gly Gly Lys Arg
        355                 360                 365
Ile Gln Gln Ala Ile Leu Ser Ile Lys Val Ser Thr Ser Leu Gly Glu
    370                 375                 380
Asp Pro Val Leu Thr Val Pro Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Ser
            420                 425                 430
Asn Lys Thr Ala Thr Leu His Ser Pro Tyr Thr Phe Asn Ala Phe Thr
        435                 440                 445
Arg Pro Gly Ser Ile Pro Cys Gln Ala Ser Ala Arg Cys Pro Asn Pro
450                 455                 460
Cys Val Thr Gly Val Tyr Thr Asp Pro Tyr Pro Leu Ile Phe Tyr Arg
```

```
            465                 470                475                 480
Asn His Thr Leu Arg Gly Val Phe Gly Thr Met Leu Asp Gly Val Gln
                    485                 490                 495

Ala Arg Leu Asn Pro Thr Ser Ala Val Phe Asp Ser Thr Ser Arg Ser
                500                 505                 510

Arg Ile Thr Arg Val Ser Ser Ser Thr Lys Ala Ala Tyr Thr Thr
            515                 520                 525

Ser Thr Cys Phe Lys Val Val Lys Thr Asn Lys Thr Tyr Cys Leu Ser
        530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly

<210> SEQ ID NO 8
<211> LENGTH: 1716
<212> TYPE: DNA
<213> ORGANISM: artificial sequence
<220> FEATURE:
<223> OTHER INFORMATION: NDV HN protein (AY288999)

<400> SEQUENCE: 8
atggatcgtg tagttagcag agttgtacta gagaacgaag aaagagaagc aaagaatact      60
tggcgcctgg ttttccggat cgcagtccta tctctaatag taatgacatt agctatctct     120
gtagccgccc tggtatacag catggaggct agcacaccga acgaccttgc gggcatatcg     180
acggtgatct ccagggcaga ggatagggtt acatctttac tcaattcaaa tcaagatgtg     240
gtagataggg tatataaaca ggtggccctt gagtccccgc tggcgttgtt gaatactgag     300
tctataatta tgaatgcaat aacttctctt cctatcaaa ttaatggggc tgcaaatagt     360
agtgggtgtg gggcacctgt tcatgacccg gattatattg gggggtagg taaagagctc     420 atagtagatg acacaagtga tgccacttca ttctatcctt cagcatatca gaacacctg     480 aactttatcc ggcgcccac cacaggatca ggctgcactc ggatacctc attcgacatg     540 agcgctaccc actattgtta tactcacaat gtgatattat ctggctgcag agatcactca     600
cactcacatc agtatttggc actaggtgtg cttcggacat ctgcaacagg agggtattc     660 ttttctactc tgcgttccat caatttagat gacacccaaa atcggaagtc ttgcagtgtg     720
agtgcaactt ctttaggttg tgatatgctg tgctctaaag tcacagagac tgaggaggag     780
gattataagt cagttacccc cacatcaatg gtgcatggaa ggttagggtt tgacggtcag     840
taccatgaga aggacttaga cgtcacagtc ttatttaagg attgggttgc aaattacccg     900
ggagtgggag gagggtctct tattgacgac cgtgtatggt tcccagttta cggcgggcta     960
aaacccaatt cgcctagcga cactgcacaa gaagggaaat atgtaatata caagcgctat    1020
aataacacat gccccgatga acaagattac caagttcgga tggctaagtc ctcgtataag    1080
cctggacggt ttggtgggaa cgcgtacag caagccatcc tatctatcaa agtatcaaca    1140
tctttgggcg aggacccggt gctgactgta ccgccaaata cagttacact catgggggcc    1200
gaaggcagaa tcctcacagt aggaacatct catttcttgt accagcgagg gtcttcatac    1260
ttttctcctg ccttactata ccctatgaca gtgcgcaaca aaacagccac tcttcatagt    1320
ccttatacat ttaatgcgtt cactcggcca ggtagtgtcc cttgccaggc atcagcaagg    1380
tgccctaact catgtatcac tggagtctat actgatccgt accctgtagt cttccatagg    1440
```

```
aatcacacct tgcgaggggt gttcgggaca atgcttgata atgaacaagc aaggctcaat    1500
cccgtatctg caatatttga ctacacatct cgcagtcgca taacccgggt aagttcgatc    1560
agcaccaagg cagcatacac gacatcgaca tgttttaaag ttgtcaagac caataaagtg    1620
tattgtctta gcattgcaga aatatccaat actctatttg gggaattcag gatcgttcct    1680
ttactggtcg agattctcaa ggatgatagg gtttaa                              1716
```

<210> SEQ ID NO 9
<211> LENGTH: 571
<212> TYPE: PRT
<213> ORGANISM: artificial sequence
<220> FEATURE:
<223> OTHER INFORMATION: NDV H -continued

```
305                 310                 315                 320

Lys Pro Asn Ser Pro Ser Asp Thr Ala Gln Glu Gly Lys Tyr Val Ile
                325                 330                 335

Tyr Lys Arg Tyr Asn Asn Thr Cys Pro Asp Glu Gln Asp Tyr Gln Val
            340                 345                 350

Arg Met Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Arg
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Ile Thr Gly Val Tyr Thr Asp Pro Tyr Pro Val Val Phe His Arg
465                 470                 475                 480

Asn His Thr Leu Arg Gly Val Phe Gly Thr Met Leu Asp Asn Glu Gln
                485                 490                 495

Ala Arg Leu Asn Pro Val Ser Ala Ile Phe Asp Tyr Thr Ser Arg Ser
            500                 505                 510

Arg Ile Thr Arg Val Ser Ser Ile Ser Thr Lys Ala Ala Tyr Thr Thr
        515                 520                 525

Ser Thr Cys Phe Lys Val Val Lys Thr Asn Lys Val Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570

<210> SEQ ID NO 10
<211> LENGTH: 14
<212> TYPE: PRT
<213> ORGANISM: artificial sequence
<220> FEATURE:
<223> OTHER INFORMATION: NDV HN linear epitope region 1

<400> SEQUENCE: 10

Pro Asp Glu Gln Asp Tyr Gln Ile Arg Met Ala Lys Ser Ser
1               5                   10

<210> SEQ ID NO 11
<211> LENGTH: 14
<212> TYPE: PRT
<213> ORGANISM: artificial sequence
<220> FEATURE:
<223> OTHER INFORMATION: NDV HN linear epitope region 2

<400> SEQUENCE: 11

Pro Asp Glu Gln Asp Tyr Gln Val Arg Met Ala Lys Ser Ser
1               5                   10

<210> SEQ ID NO 12
<211> LENGTH: 78
```
<212> TYPE: DNA
<213> ORGANISM: artificial sequence
<220> FEATURE:
<223> OTHER INFORMATION: NDV HN signal sequence

<400> SEQUENCE: 12
atggaccgtg tcgtctcccg cgtggtcctc gagaacgagg agcgtgaggc caagaacacc 60
tggcgccttg tctttcgt 78

<210> SEQ ID NO 13
<211> LENGTH: 26
<212> TYPE: PRT
<213> ORGANISM: artificial sequence
<220> FEATURE:
<223> OTHER INFORMATION: NDV HN signal peptide

<400> SEQUENCE: 13

Met Asp Arg Val Val Ser Arg Val Val Leu Glu Asn Glu Glu Arg Glu
1 5 10 15

Ala Lys Asn Thr Trp Arg Leu Val Phe Arg
20 25

<210> SEQ ID NO 14
<211> LENGTH: 1638
<212> TYPE: DNA
<213> ORGANISM: artificial sequence
<220> FEATURE:
<223> OTHER INFORMATION: NDV HN DNA without signal seq

<400> SEQUENCE: 14
gtcgccgtcc tctcccttat tgtcatgacc ctcgccatct ccgtcgccgc cctcgtctac 60
agcatggagg ctagcacccc caacgatctc gccggaatct cgactgttat ctcccgcgcc 120
gaggaccgcg tcacctccct cctcaactcc aaccaggatg tcgttgatcg cgtctacaag 180
caggtcgccc tcgagtcccc tctcgccctc cttaacaccg agagcatcat tatgaacgcc 240
attacctccc tcagctacca gattaacggc gccgccaact cgtccggctg cggcgccccc 300
gtccatgacc ctgattacat cggcggcgtc ggcaaggagc tcatcgtcga cgacactagc 360
gatgccacgt ccttctaccc tagcgcctac caggagcacc tcaacttcat ccctgccccc 420
actaccggct ccggctgcac ccgcattccc agcttcgaca tgtccgccac tcactactgc 480
tacacccata acgtcatcct ttcgggttgc cgcgaccact cccacagcca ccagtacctc 540
gccctcggag ttcttcgtac gtccgccacc ggccgcgtct ttttttccac cctccgcagc 600
atcaacctcg acgataccca gaaccgcaag agctgctcgg tctccgccac cccgctcggc 660
tgcgacatgc tctgctccaa ggtcaccgag acggaggagg aggattacaa gtccgttacc 720
cccacttcga tggtccacgg ccgccttggc ttcgacggcc agtaccacga gaaggacctc 780
gacgtcaccg ttctctttaa ggactgggtt gccaactacc ccggcgtcgg cggcggctcc 840
ctcatcgatg accgcgtctg gtttcctgtc tacggtggtc tcaagcctaa cagcccctcc 900
gataccgccc aggagggtaa gtacgtgatc tacaagcgct acaacaacac ctgccctgac 960
gagcaggatt accaggtccg catggccaag tcctcgtaca agcccggtcg tttcggcggc 1020
aagcgcgtcc agcaggccat tctctcgatc aaggtctcga ccagcctcgg agaggacccc 1080
gtgctcaccg ttccccctaa caccgtcacc cttatgggcg ccgagggccg catcctcacc 1140
gtcggtacct cccacttcct ctaccagcgc ggctcgagct acttttcccc tgcccttctt 1200
taccccatga ctgttcgcaa caagactgct accctccaca gcccctacac ctttaacgcc 1260

```
ttcacgcgcc ccggaagcgt cccctgccag gcgagcgccc gctgccctaa ctcctgcatt   1320
accggcgtct acaccgaccc ttaccctgtc gtctttcacc gcaaccatac ccttcgcggc   1380
gtcttcggta ctatgcttga taacgagcag gcccgcctca accccgtctc cgccattttc   1440
gactacactt cccgctcccg tatcacccgc gtctcctcca cctccaccaa ggccgcctac   1500
accacctcca cctgctttaa ggttgtcaag actaacaagg tctactgcct ctccatcgcc   1560
gagattagca acaccctctt cggagagttc cgcattgtcc ccctgctcgt cgagatcctc   1620
aaggacgatc gcgtttaa                                                 1638

<210> SEQ ID NO 15
<211> LENGTH: 545
<212> TYPE: PRT
<213> ORGANISM: artificial sequence
<220> FEATURE:
<223> OTHER INFORMATION: NDV HN mature protein (without signal peptide)

<400> SEQUENCE: 15

Val Ala Val Leu Ser Leu Ile Val Met Thr Leu Ala Ile Ser Val Ala
1               5                   10                  15

Ala Leu Val Tyr Ser Met Glu Ala Ser Thr Pro Asn Asp Leu Ala Gly
            20                  25                  30

Ile Ser Thr Val Ile Ser Arg Ala Glu Asp Arg Val Thr Ser Leu Leu
        35                  40                  45

Asn Ser Asn Gln Asp Val Val Asp Arg Val Tyr Lys Gln Val Ala Leu
    50                  55                  60

Glu Ser Pro Leu Ala Leu Leu Asn Thr Glu Ser Ile Ile Met Asn Ala
65                  70                  75                  80

Ile Thr Ser Leu Ser Tyr Gln Ile Asn Gly Ala Ala Asn Ser Ser Gly
                85                  90                  95

Cys Gly Ala Pro Val His Asp Pro Asp Tyr Ile Gly Gly Val Gly Lys
            100                 105                 110

Glu Leu Ile Val Asp Asp Thr Ser Asp Ala Thr Ser Phe Tyr Pro Ser
        115                 120                 125

Ala Tyr Gln Glu His Leu Asn Phe Ile Pro Ala Pro Thr Thr Gly Ser
    130                 135                 140

Gly Cys Thr Arg Ile Pro Ser Phe Asp Met Ser Ala Thr His Tyr Cys
145                 150                 155                 160

Tyr Thr His Asn Val Ile Leu Ser Gly Cys Arg Asp His Ser His Ser
                165                 170                 175

His Gln Tyr Leu Ala Leu Gly Val Leu Arg Thr Ser Ala Thr Gly Arg
            180                 185                 190

Val Phe Phe Ser Thr Leu Arg Ser Ile Asn Leu Asp Asp Thr Gln Asn
        195                 200                 205

Arg Lys Ser Cys Ser Val Ser Ala Thr Pro Leu Gly Cys Asp Met Leu
    210                 215                 220

Cys Ser Lys Val Thr Glu Thr Glu Glu Glu Asp Tyr Lys Ser Val Thr
225                 230                 235                 240

Pro Thr Ser Met Val His Gly Arg Leu Gly Phe Asp Gly Gln Tyr His
                245                 250                 255

Glu Lys Asp Leu Asp Val Thr Val Leu Phe Lys Asp Trp Val Ala Asn
            260                 265                 270

Tyr Pro Gly Val Gly Gly Gly Ser Leu Ile Asp Asp Arg Val Trp Phe
        275                 280                 285

Pro Val Tyr Gly Gly Leu Lys Pro Asn Ser Pro Ser Asp Thr Ala Gln
```

```
                290                 295                 300
Glu Gly Lys Tyr Val Ile Tyr Lys Arg Tyr Asn Asn Thr Cys Pro Asp
305                 310                 315                 320

Glu Gln Asp Tyr Gln Val Arg Met Ala Lys Ser Ser Tyr Lys Pro Gly
            325                 330                 335

Arg Phe Gly Gly Lys Arg Val Gln Gln Ala Ile Leu Ser Ile Lys Val
                340                 345                 350

Ser Thr Ser Leu Gly Glu Asp Pro Val Leu Thr Val Pro Pro Asn Thr
        355                 360                 365

Val Thr Leu Met Gly Ala Glu Gly Arg Ile Leu Thr Val Gly Thr Ser
    370                 375                 380

His Phe Leu Tyr Gln Arg Gly Ser Ser Tyr Phe Ser Pro Ala Leu Leu
385                 390                 395                 400

Tyr Pro Met Thr Val Arg Asn Lys Thr Ala Thr Leu His Ser Pro Tyr
            405                 410                 415

Thr Phe Asn Ala Phe Thr Arg Pro Gly Ser Val Pro Cys Gln Ala Ser
                420                 425                 430

Ala Arg Cys Pro Asn Ser Cys Ile Thr Gly Val Tyr Thr Asp Pro Tyr
        435                 440                 445

Pro Val Val Phe His Arg Asn His Thr Leu Arg Gly Val Phe Gly Thr
    450                 455                 460

Met Leu Asp Asn Glu Gln Ala Arg Leu Asn Pro Val Ser Ala Ile Phe
465                 470                 475                 480

Asp Tyr Thr Ser Arg Ser Arg Ile Thr Arg Val Ser Ser Thr Ser Thr
            485                 490                 495

Lys Ala Ala Tyr Thr Thr Ser Thr Cys Phe Lys Val Val Lys Thr Asn
                500                 505                 510

Lys Val Tyr Cys Leu Ser Ile Ala Glu Ile Ser Asn Thr Leu Phe Gly
        515                 520                 525

Glu Phe Arg Ile Val Pro Leu Leu Val Glu Ile Leu Lys Asp Asp Arg
    530                 535                 540

Val
545

<210> SEQ ID NO 16
<211> LENGTH: 1713
<212> TYPE: DNA
<213> ORGANISM: artificial sequence
<220> FEATURE:
<223> OTHER INFORMATION: NDV HN DNA (FJ608369)

<400> SEQUENCE: 16
atgggacgcg cggttaacag agtcgcgctg gagaatgagg aaagagaagc aaagaacaca        60
tggcgcctgg ttttccggat cgcagtctta cttttaatgg taatgactct agctatctcc      120
gcagctgccc tggcatacag tgcggggggcc agtacgccgc acgacctcgc aggcatatcg      180
actgtgatct ctaagacaga ggataaggtt acgtctttac tcagttcgag tcaagatgtg      240
atagatagga tatacaagca ggtggctctt gaatccccac tggcgctact aaacactgaa      300
tctatgatta tgaatgcaat aacctctctt tcttatcaaa ttaacggggc tgcgaacaat      360
agcggatgtg gggcgcctgt tcatgaccca gattatatcg gggggatagg caaagaactc      420
atagtggacg acatcagtga tgtcacatca ttttatcctt ctgcatatca agaaacttg       480 aatttcatcc cggcgcctac tacaggatcc ggttgcactc ggatacccte atttgacatg      540 agcaccaccc attattgtta tactcacaat gtgatactat ccggttgcag agatcactca      600
```

```
cactcacatc aatacttagc acttggtgtg cttcggacat ctgcaacagg gagggtattc      660
ttttctactc tgcgctccat caatttagat gacacccaaa atcggaagtc ctgcagtgtg      720
agtgcaaccc ctttaggttg tgatatgctg tgctctaagg tcacagggac tgaagaggag      780
gattacaagt cagttgcccc cacaccaatg gtgcacggaa ggctagggtt tgacggtcaa      840
taccatgaga aggacttaga caccacggtc ttatttaagg attgggtggc aaattaccca      900
ggagtgggag gagggtcttt tattgacaac cgtgtatggt tcccagttta cggagggctc      960
aaacccaatt cacccagtga cactgcacaa gaagggaaat atgtaatata taagcgccat     1020
aacaacacat gccccgataa acaagattac caaattcgga tggctaagtc ttcatataaa     1080
cccgggcgat ttggtggaaa gcgcgtacag caagccatct tatccatcaa agtgtcaaca     1140
tccttgggta aggacccggt gctgactatt ccacctaata caatcacact catgggagcc     1200
gaaggcagaa tcctcacagt agggacatct cacttcttgt accaacgagg gtcttcatat     1260
ttctcccctg ccttattata tcccatgaca gtaaataaca aaacggctac actccatagt     1320
ccttatacgt ttaatgctttt cactcggcca ggtagtgccc cttgccaggc atcagcaaga     1380
tgccccaact catgcatcac tggagtctat actgatccat atcccttaat cttccatagg     1440
aatcatactc tacgagggg t cttcgggacg atgcttgatg atgaacaagc gagacttaac     1500
cccgtatctg cagtattcga caacatatcc cgcagtcgtg tcacccgggt gagttcaagc     1560
agcaccaagg cagcatacac aacatcgaca tgttttaaag ttgtcaagac caataaagct     1620
tattgtctta gtattgcaga aatatccaat accctattcg gggaatttag gatcgttccc     1680
ttattagttg agatcctcaa ggatgataga gtt                                  1713
```

<210> SEQ ID NO 17
<211> LENGTH: 571
<212> TYPE: PRT
<213> ORGANISM: artificial sequence
<220> FEATURE:
<223> OTHER INFORMATION: NDV HN protein (ACM67348)

<400> SEQUENCE: 17

```
Met Gly Arg Ala Val Asn Arg Val Ala Leu Glu Asn Glu Glu Arg Glu
1               5                   10                  15

Ala Lys Asn Thr Trp Arg Leu Val Phe Arg Ile Ala Val Leu Leu Leu
            20                  25                  30

Met Val Met Thr Leu Ala Ile Ser Ala Ala Ala Leu Ala Tyr Ser Ala
        35                  40                  45

Gly Ala Ser Thr Pro His Asp Leu Ala Gly Ile Ser Thr Val Ile Ser
    50                  55                  60

Lys Thr Glu Asp Lys Val Thr Ser Leu Leu Ser Ser Ser Gln Asp Val
65                  70                  75                  80

Ile Asp Arg Ile Tyr Lys Gln Val Ala Leu Glu Ser Pro Leu Ala Leu
                85                  90                  95

Leu Asn Thr Glu Ser Met Ile Met Asn Ala Ile Thr Ser Leu Ser Tyr
            100                 105                 110

Gln Ile Asn Gly Ala Ala Asn Asn Ser Gly Cys Gly Ala Pro Val His
        115                 120                 125

Asp Pro Asp Tyr Ile Gly Gly Ile Gly Lys Glu Leu Ile Val Asp Asp
    130                 135                 140

Ile Ser Asp Val Thr Ser Phe Tyr Pro Ser Ala Tyr Gln Glu His Leu
145                 150                 155                 160
```

```
Asn Phe Ile Pro Ala Pro Thr Thr Gly Ser Gly Cys Thr Arg Ile Pro
                165                 170                 175

Ser Phe Asp Met Ser Thr Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Gly
                245                 250                 255

Thr Glu Glu Glu Asp Tyr Lys Ser Val Ala Pro Thr Pro Met Val His
            260                 265                 270

Gly Arg Leu Gly Phe Asp Gly Gln Tyr His Glu Lys Asp Leu Asp Thr
        275                 280                 285

Thr Val Leu Phe Lys Asp Trp Val Ala Asn Tyr Pro Gly Val Gly Gly
    290                 295                 300

Gly Ser Phe Ile Asp Asn Arg Val Trp Phe Pro Val Tyr Gly Gly Leu
305                 310                 315                 320

Lys Pro Asn Ser Pro Ser Asp Thr Ala Gln Glu Gly Lys Tyr Val Ile
                325                 330                 335

Tyr Lys Arg His Asn Asn Thr Cys Pro Asp Lys Gln Asp Tyr Gln Ile
            340                 345                 350

Arg Met Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Lys
    370                 375                 380

Asp Pro Val Leu Thr Ile Pro Pro Asn Thr Ile Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Asn
            420                 425                 430

Asn Lys Thr Ala Thr Leu His Ser Pro Tyr Thr Phe Asn Ala Phe Thr
        435                 440                 445

Arg Pro Gly Ser Ala Pro Cys Gln Ala Ser Ala Arg Cys Pro Asn Ser
    450                 455                 460

Cys Ile Thr Gly Val Tyr Thr Asp Pro Tyr Pro Leu Ile Phe His Arg
465                 470                 475                 480

Asn His Thr Leu Arg Gly Val Phe Gly Thr Met Leu Asp Asp Glu Gln
                485                 490                 495

Ala Arg Leu Asn Pro Val Ser Ala Val Phe Asp Asn Ile Ser Arg Ser
            500                 505                 510

Arg Val Thr Arg Val Ser Ser Ser Thr Lys Ala Ala Tyr Thr Thr Thr
        515                 520                 525

Ser Thr Cys Phe Lys Val Val Lys Thr Asn Lys Ala Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570
```

<210> SEQ ID NO 18
<211> LENGTH: 1716
<212> TYPE: DNA
<213> ORGANISM: artificial sequence
<220> FEATURE:
<223> OTHER INFORMATION: NDV HN DNA (strain ZJ1)

<400> SEQUENCE: 18

```
atggaccgcg cggttaacag agtcgtgctg gagaatgagg aaagagaagc aaagaacaca      60
tggcgcctgg ttttccggat cgcagtctta cttttaatgg taatgactct agctatctcc     120
gcagctgccc tggcatacag tacggggggcc agtacgccgc acgacctcgc aggcatatcg    180
actgtgatct ccaagacaga agataaggtt acatctttac tcagtttgag tcaagatgtg     240
atagataaga tatacaagca ggtggctctt aatccccgc tggcgctact aaacactgaa      300
tctataatta tgaatgcaat aacctctctt tcttatcaaa ttaacggggc tgcgaacaat     360
agcggatgtg gggcgcctgt tcatgaccca gattatatcg gggggatagg caaagaactc     420
atagtggacg acatcagtga tgtcacatca ttttatcctt ctgcatatca agaacacttg     480
aatttcatcc cggcgcctac tacaggatcc ggttgcactc ggataccctc atttgacatg     540
agcaccaccc attattgtta tactcacaat gtgatactat ccggttgcag agatcactca     600
cactcacatc aatacttagc acttggtgtg cttcggacat ctgcaacagg agggtattc     660
tttctactc tgcgctccac caatttagat gacacccaaa atcggaagtc ctgcagtgtg     720
agtgcaaccc ctttaggttg tgatatgctg tgctctaagg tcacagagac tgaagaggag     780
gattacaagt cagttgcccc cacatcaatg gtgcacggaa ggctagggtt tgacggtcaa     840
taccatgaga aggacttaga caccacggtc ttatttaagg attgggtggc aaattaccca     900
ggagcgggag gagggtcttt tattgacgac cgtgtatggt tcccagttta cggagggctc     960
aaacccaatt cacccagtga cactgcacaa gaagggaaat atgtaataata caagcgccat    1020
aacaacacat gccctgatga acaagattac caaattcgga tggctaagtc ttcatataaa    1080
cccgggcgat ttggtggaaa gcgcgtacag caagccatcc tatccatcaa agtgtcaaca   1140
tccttgggta aggacccggt gctgactatt ccacctaata caatcacact catgggagcc   1200
gaaggcagaa tcctcacagt agggacatct cacttcttgt accaacgagg gtcttcatat   1260
ttctcccctg ccttattata tcccatgaca gtaaataaca aaacggctac actccatagt   1320
ccttatacgt ttaatgcttt cactcggcca ggtagtgtcc cttgccaggc atcagcaaga   1380
tgcccccaact catgcatcac tggggtctat actgatccat atccttaat cttccatagg   1440
aatcatactc tacgaggggt cttcgggacg atgcttgatg atgaacaagc agacttaac   1500
cccgtatctg cagtattcga caacatatct cgcagtcgtg tcacccgggt gagttcaagc   1560
agcaccaagg cagcatacac gacatcgaca tgttttaaag ttgtcaagac caataaaact   1620
tattgtctta gtattgcaga aatatccaat accctattcg gggaatttag gatcgttccc   1680
ttattagttg agatcctcaa ggatgataga gtttaa                             1716
```

<210> SEQ ID NO 19
<211> LENGTH: 571
<212> TYPE: PRT
<213> ORGANISM: artificial sequence
<220> FEATURE:
<223> OTHER INFORMATION: NDV HN protein (AAL18936)

<400> SEQUENCE: 19

```
Met Asp Arg Ala Val Asn Arg Val Val Leu Glu Asn Glu Glu Arg Glu
1               5                   10                  15
```

-continued

```
Ala Lys Asn Thr Trp Arg Leu Val Phe Arg Ile Ala Val Leu Leu Leu
         20                  25                  30

Met Val Met Thr Leu Ala Ile Ser Ala Ala Ala Leu Ala Tyr Ser Thr
         35                  40                  45

Gly Ala Ser Thr Pro His Asp Leu Ala Gly Ile Ser Thr Val Ile Ser
 50                      55                  60

Lys Thr Glu Asp Lys Val Thr Ser Leu Leu Ser Leu Ser Gln Asp Val
 65                  70                  75                  80

Ile Asp Lys Ile Tyr Lys Gln Val Ala Leu Glu Ser Pro Leu Ala Leu
             85                  90                  95

Leu Asn Thr Glu Ser Ile Ile Met Asn Ala Ile Thr Ser Leu Ser Tyr
             100                 105                 110

Gln Ile Asn Gly Ala Ala Asn Asn Ser Gly Cys Gly Ala Pro Val His
             115                 120                 125

Asp Pro Asp Tyr Ile Gly Gly Ile Gly Lys Glu Leu Ile Val Asp Asp
130                 135                 140

Ile Ser Asp Val Thr Ser Phe Tyr Pro Ser Ala Tyr Gln Glu His Leu
145                 150                 155                 160

Asn Phe Ile Pro Ala Pro Thr Thr Gly Ser Gly Cys Thr Arg Ile Pro
                 165                 170                 175

Ser Phe Asp Met Ser Thr Thr His Tyr Cys Tyr Thr His Asn Val Ile
                 180                 185                 190

Leu Ser Gly Cys Arg Asp His Ser His Ser His Gln Tyr Leu Ala Leu
             195                 200                 205

Gly Val Leu Arg Thr Ser Ala Thr Gly Arg Val Phe Phe Ser Thr Leu
             210                 215                 220

Arg Ser Thr Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                 245                 250                 255

Thr Glu Glu Glu Asp Tyr Lys Ser Val Ala Pro Thr Ser Met Val His
             260                 265                 270

Gly Arg Leu Gly Phe Asp Gly Gln Tyr His Glu Lys Asp Leu Asp Thr
             275                 280                 285

Thr Val Leu Phe Lys Asp Trp Val Ala Asn Tyr Pro Gly Ala Gly Gly
         290                 295                 300

Gly Ser Phe Ile Asp Asp Arg Val Trp Phe Pro Val Tyr Gly Gly Leu
305                 310                 315                 320

Lys Pro Asn Ser Pro Ser Asp Thr Ala Gln Glu Gly Lys Tyr Val Ile
                 325                 330                 335

Tyr Lys Arg His Asn Asn Thr Cys Pro Asp Glu Gln Asp Tyr Gln Ile
             340                 345                 350

Arg Met Ala Lys Ser Ser Tyr Lys Pro Gly Arg Phe Gly Gly Lys Arg
             355                 360                 365

Val Gln Gln Ala Ile Leu Ser Ile Lys Val Ser Thr Ser Leu Gly Lys
             370                 375                 380

Asp Pro Val Leu Thr Ile Pro Pro Asn Thr Ile Thr Leu Met Gly Ala
385                 390                 395                 400

Glu Gly Arg Ile Leu Thr Val Gly Thr Ser His Phe Leu Tyr Gln Arg
                 405                 410                 415

Gly Ser Ser Tyr Phe Ser Pro Ala Leu Leu Tyr Pro Met Thr Val Asn
             420                 425                 430
```

```
Asn Lys Thr Ala Thr Leu His Ser Pro Tyr Thr Phe Asn Ala Phe Thr
            435                 440                 445

Arg Pro Gly Ser Val Pro Cys Gln Ala Ser Ala Arg Cys Pro Asn Ser
450                 455                 460

Cys Ile Thr Gly Val Tyr Thr Asp Pro Tyr Pro Leu Ile Phe His Arg
465                 470                 475                 480

Asn His Thr Leu Arg Gly Val Phe Gly Thr Met Leu Asp Asp Glu Gln
                485                 490                 495

Ala Arg Leu Asn Pro Val Ser Ala Val Phe Asp Asn Ile Ser Arg Ser
                500                 505                 510

Arg Val Thr Arg Val Ser Ser Ser Thr Lys Ala Ala Tyr Thr Thr
            515                 520                 525

Ser Thr Cys Phe Lys Val Val Lys Thr Asn Lys Thr Tyr Cys Leu Ser
            530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570

<210> SEQ ID NO 20
<211> LENGTH: 525
<212> TYPE: PRT
<213> ORGANISM: artificial sequence
<220> FEATURE:
<223> OTHER INFORMATION: NDV HN mature protein sequence (without signal
      pepetide of ACM67348)

<400> SEQUENCE: 20

Ser Ala Gly Ala Ser Thr Pro His Asp Leu Ala Gly Ile Ser Thr Val
1               5                   10                  15

Ile Ser Lys Thr Glu Asp Lys Val Thr Ser Leu Leu Ser Ser Ser Gln
                20                  25                  30

Asp Val Ile Asp Arg Ile Tyr Lys Gln Val Ala Leu Glu Ser Pro Leu
            35                  40                  45

Ala Leu Leu Asn Thr Glu Ser Met Ile Met Asn Ala Ile Thr Ser Leu
50                  55                  60

Ser Tyr Gln Ile Asn Gly Ala Ala Asn Asn Ser Gly Cys Gly Ala Pro
65                  70                  75                  80

Val His Asp Pro Asp Tyr Ile Gly Gly Ile Gly Lys Glu Leu Ile Val
                85                  90                  95

Asp Asp Ile Ser Asp Val Thr Ser Phe Tyr Pro Ser Ala Tyr Gln Glu
            100                 105                 110

His Leu Asn Phe Ile Pro Ala Pro Thr Thr Gly Ser Gly Cys Thr Arg
        115                 120                 125

Ile Pro Ser Phe Asp Met Ser Thr Thr His Tyr Cys Tyr Thr His Asn
130                 135                 140

Val Ile Leu Ser Gly Cys Arg Asp His Ser His Ser His Gln Tyr Leu
145                 150                 155                 160

Ala Leu Gly Val Leu Arg Thr Ser Ala Thr Gly Arg Val Phe Phe Ser
                165                 170                 175

Thr Leu Arg Ser Ile Asn Leu Asp Asp Thr Gln Asn Arg Lys Ser Cys
            180                 185                 190

Ser Val Ser Ala Thr Pro Leu Gly Cys Asp Met Leu Cys Ser Lys Val
        195                 200                 205

Thr Gly Thr Glu Glu Glu Asp Tyr Lys Ser Val Ala Pro Thr Pro Met
210                 215                 220
```

Val His Gly Arg Leu Gly Phe Asp Gly Gln Tyr His Glu Lys Asp Leu
225                 230                 235                 240

Asp Thr Thr Val Leu Phe Lys Asp Trp Val Ala Asn Tyr Pro Gly Val
            245                 250                 255

Gly Gly Gly Ser Phe Ile Asp Asn Arg Val Trp Phe Pro Val Tyr Gly
        260                 265                 270

Gly Leu Lys Pro Asn Ser Pro Ser Asp Thr Ala Gln Glu Gly Lys Tyr
    275                 280                 285

Val Ile Tyr Lys Arg His Asn Asn Thr Cys Pro Asp Lys Gln Asp Tyr
290                 295                 300

Gln Ile Arg Met Ala Lys Ser Ser Tyr Lys Pro Gly Arg Phe Gly Gly
305                 310                 315                 320

Lys Arg Val Gln Gln Ala Ile Leu Ser Ile Lys Val Ser Thr Ser Leu
            325                 330                 335

Gly Lys Asp Pro Val Leu Thr Ile Pro Pro Asn Thr Ile Thr Leu Met
        340                 345                 350

Gly Ala Glu Gly Arg Ile Leu Thr Val Gly Thr Ser His Phe Leu Tyr
    355                 360                 365

Gln Arg Gly Ser Ser Tyr Phe Ser Pro Ala Leu Leu Tyr Pro Met Thr
370                 375                 380

Val Asn Asn Lys Thr Ala Thr Leu His Ser Pro Tyr Thr Phe Asn Ala
385                 390                 395                 400

Phe Thr Arg Pro Gly Ser Ala Pro Cys Gln Ala Ser Ala Arg Cys Pro
            405                 410                 415

Asn Ser Cys Ile Thr Gly Val Tyr Thr Asp Pro Tyr Pro Leu Ile Phe
        420                 425                 430

His Arg Asn His Thr Leu Arg Gly Val Phe Gly Thr Met Leu Asp Asp
    435                 440                 445

Glu Gln Ala Arg Leu Asn Pro Val Ser Ala Val Phe Asp Asn Ile Ser
450                 455                 460

Arg Ser Arg Val Thr Arg Val Ser Ser Ser Thr Lys Ala Ala Tyr
465                 470                 475                 480

Thr Thr Ser Thr Cys Phe Lys Val Val Lys Thr Asn Lys Ala Tyr Cys
            485                 490                 495

Leu Ser Ile Ala Glu Ile Ser Asn Thr Leu Phe Gly Glu Phe Arg Ile
        500                 505                 510

Val Pro Leu Leu Val Glu Ile Leu Lys Asp Asp Arg Val
    515                 520                 525

<210> SEQ ID NO 21
<211> LENGTH: 46
<212> TYPE: PRT
<213> ORGANISM: artificial sequence
<220> FEATURE:
<223> OTHER INFORMATION: NDV HN signal peptide (of ACM67348)

<400> SEQUENCE: 21

Met Gly Arg Ala Val Asn Arg Val Ala Leu Glu Asn Glu Glu Arg Glu
1               5                   10                  15

Ala Lys Asn Thr Trp Arg Leu Val Phe Arg Ile Ala Val Leu Leu Leu
            20                  25                  30

Met Val Met Thr Leu Ala Ile Ser Ala Ala Ala Leu Ala Tyr
        35                  40                  45

<210> SEQ ID NO 22

<211> LENGTH: 1713
<212> TYPE: DNA
<213> ORGANISM: artificial sequence
<220> FEATURE:
<223> OTHER INFORMATION: NDV HN codon-optimized (duckweed-preferred) DNA
(for ACM67348)

<400> SEQUENCE: 22
atgggccggg ccgtcaaccg cgtggcgttg gagaacgagg agcgggaggc caagaacacc 60
tggaggctcg tgttccgcat cgccgtgctc ctgctcatgg tcatgaccct ggcgatctcg 120
gccgcggccc tggcctactc cgccggtgcg agcaccccgc acgacctggc cgggatcagc 180
accgtcatct cgaagaccga ggacaaggtg acgtccctgc tcagctcgtc ccaggacgtt 240
atcgaccgca tctacaagca agtcgccttg gagagccctc tggccctgct caacacggag 300
agcatgatca tgaacgcgat cacctccctg agctaccaga tcaacggggc cgcgaacaat 360
tccgggtgcg gcgcccccgt gcacgaccct gactacatcg gcgggatcgg caaggaactc 420
atcgttgacg acatcagcga cgtgacgtcg ttctacccct ccgcctacca ggagcacctc 480
aacttcatcc ccgccccgac cacggggagc ggctgcaccc ggatcccgtc cttcgacatg 540
tccaccacgc actattgcta cacccacaac gtgatcctgt cggggtgccg cgaccacagc 600
cactcgcacc agtacctggc gctgggcgtc ctcaggacct ccgcgaccgg ccgcgtgttc 660
ttctccactc tccgctccat caacctggac gatacgcaga accgcaagtc ctgcagcgtg 720
tccgccacgc ccctcggctg cgacatgctc tgctccaagg tgaccggcac cgaggaggag 780
gactacaagt ccgtggcccc caccccgatg gtgcacgggc ggctcggctt cgatggtcag 840
taccacgaga aggacctgga cacgaccgtg ctcttcaagg actgggtggc gaactacccc 900
ggtgtggggg gcggtagctt catcgacaac agagtctggt tccccgtgta cgggggcctg 960
aagcccaact ccccctccga cacggcccag gaggggaagt acgtcatcta caagcggcac 1020
aacaacacct gcccggacaa gcaggactat cagatccgga tggccaaaag ctcctacaag 1080
cccggccgct tcgggggcaa gagagtccag caggcgatcc tctccatcaa ggtgagcacg 1140
agcctcggca aggacccggt cctgaccatc cccccgaaca ccatcaccct catgggcgcc 1200
gaggggagaa tcctcactgt cggcacctcc cacttcctgt accagcgggg cagctcgtac 1260
ttcagcccgg cgctcctgta cccgatgacc gtcaacaaca agaccgccac gctgcactcg 1320
ccctacacct tcaacgcctt cacccgcccc ggcagcgccc cgtgccaggc ctccgcccgc 1380
tgcccgaact cgtgcatcac cggggtctac accgaccctt acccgctgat cttccaccgc 1440
aaccacacgc tcaggggggt gttcgggacc atgctcgacg acgagcaggc tcgcctgaac 1500
cccgtcagcg ccgtcttcga caacatctcc cgcagccgcg tcacgagagt ctcctcgtcc 1560
tcgacgaagg ccgcgtacac cacgtccacc tgcttcaagg tggttaagac caacaaagcc 1620
tactgcctct ccatcgctga gatctccaac accctcttcg gcgagttccg gatcgtgccc 1680
ctcttggtgg agatcctgaa ggacgaccgc gtg 1713

<210> SEQ ID NO 23
<211> LENGTH: 1575
<212> TYPE: DNA
<213> ORGANISM: artificial sequence
<220> FEATURE:
<223> OTHER INFORMATION: NDV HN codon-optimized (duckweed) encoding
mature protein (ACM67348)

<400> SEQUENCE: 23
tccgccggtg cgagcacccc gcacgacctg gccgggatca gcaccgtcat ctcgaagacc 60

```
gaggacaagg tgacgtccct gctcagctcg tcccaggacg ttatcgaccg catctacaag    120
caagtcgcct tggagagccc tctggccctg ctcaacacgg agagcatgat catgaacgcg    180
atcacctccc tgagctacca gatcaacggg gccgcgaaca attccgggtg cggcgccccc    240
gtgcacgacc ctgactacat cggcgggatc ggcaaggaac tcatcgttga cgacatcagc    300
gacgtgacgt cgttctaccc ctccgcctac caggagcacc tcaacttcat ccccgccccg    360
accacgggga gcggctgcac ccggatcccg tccttcgaca tgtccaccac gcactattgc    420
tacacccaca acgtgatcct gtcggggtgc cgcgaccaca gccactcgca ccagtacctg    480
gcgctgggcg tcctcaggac ctccgcgacc ggccgcgtgt tcttctccac tctccgctcc    540
atcaacctgg acgatacgca gaaccgcaag tcctgcagcg tgtccgccac gccctcggc    600 tgcgacatgc tctgctccaa ggtgaccgga accgaggagg aggactacaa gtccgtggcc    660
cccaccccga tggtgcacgg gcggctcggc ttcgatggtc agtaccacga aggacctg    720 gacacgaccg tgctcttcaa ggactgggtg gcgaactacc ccgtgtgggg gggcggtagc    780
ttcatcgaca acagagtctg gttccccgtg tacgggggcc tgaagcccaa ctcccccctcc    840 gacacggccc aggaggggaa gtacgtcatc tacaagcggc acaacaacac ctgcccggac    900
aagcaggact atcagatccg gatggccaaa agctcctaca gcccggccg cttcggggc    960 aagagagtcc agcaggcgat cctctccatc aaggtgagca cgagcctcgg caaggacccg    1020
gtcctgacca tccccccgaa caccatcacc ctcatgggcg ccgaggggag aatcctcact    1080
gtcggcacct cccacttcct gtaccagcgg ggcagctcgt acttcagccc ggcgctcctg    1140
tacccgatga ccgtcaacaa caagaccgcc acgctgcact cgccctacac cttcaacgcc    1200
ttcacccgcc ccggcagcgc cccgtgccag gcctccgccc gctgcccgaa ctcgtgcatc    1260
accggggtct acaccgaccc ttaccgctg atcttccacc gcaaccacac gctcagggg    1320 gtgttcggga ccatgctcga cgacgagcag gctcgcctga ccccgtcag cgccgtcttc    1380 gacaacatct cccgcagccg cgtcacgaga gtctcctcgt cctcgacgaa ggccgcgtac    1440
accacgtcca cctgcttcaa ggtggttaag accaacaaag cctactgcct ctccatcgct    1500
gagatctcca cacccctctt cggcgagttc cggatcgtgc ccctcttggt ggagatcctg    1560
aaggacgacc gcgtg                                                    1575
```

<210> SEQ ID NO 24
<211> LENGTH: 4
<212> TYPE: PRT
<213> ORGANISM: artificial sequence
<220> FEATURE:
<223> OTHER INFORMATION: ER retention seq

<400> SEQUENCE: 24

Lys Asp Glu Leu
1

<210> SEQ ID NO 25
<211> LENGTH: 93
<212> TYPE: DNA
<213> ORGANISM: artificial sequence
<220> FEATURE:
<223> OTHER INFORMATION: alpha amylase signal seq

<400> SEQUENCE: 25

```
atgcaggtcc tgaacacgat ggtcaacaag cacttcctct ccctgtccgt cctcatcgtc    60
ctcctcgggc tgagcagcaa cctcaccgcc ggc                                 93
```

```
<210> SEQ ID NO 26
<211> LENGTH: 31
<212> TYPE: PRT
<213> ORGANISM: artificial sequence
<220> FEATURE:
<223> OTHER INFORMATION: alpha amylase signal peptide

<400> SEQUENCE: 26

Met Gln Val Leu Asn Thr Met Val Asn Lys His Phe Leu Ser Leu Ser
1               5                   10                  15

Val Leu Ile Val Leu Leu Gly Leu Ser Ser Asn Leu Thr Ala Gly
            20                  25                  30

<210> SEQ ID NO 27
<211> LENGTH: 138
<212> TYPE: DNA
<213> ORGANISM: artificial sequence
<220> FEATURE:
<223> OTHER INFORMATION: NDV HN signal sequence codon-optimized
      (duckweed)

<400> SEQUENCE: 27
atgggccggg ccgtcaaccg cgtggcgttg gagaacgagg agcgggaggc caagaacacc        60
tggaggctcg tgttccgcat cgccgtgctc ctgctcatgg tcatgaccct ggcgatctcg       120
gccgcggccc tggcctac                                                    138

<210> SEQ ID NO 28
<211> LENGTH: 14
<212> TYPE: PRT
<213> ORGANISM: artificial sequence
<220> FEATURE:
<223> OTHER INFORMATION: NDV HN linear epitope region 3

<400> SEQUENCE: 28

Pro Asp Lys Gln Asp Tyr Gln Ile Arg Met Ala Lys Ser Ser
1               5                   10
```